(12) United States Patent
Livet et al.

(10) Patent No.: US 12,281,319 B2
(45) Date of Patent: Apr. 22, 2025

(54) MOLECULAR TOOLS AND METHODS FOR TRANSGENE INTEGRATION AND THEIR TRANSPOSITION DEPENDENT EXPRESSION

(71) Applicants: SORBONNE UNIVERSITE, Paris (FR); INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR)

(72) Inventors: Jean Livet, Paris (FR); Takuma Kumamoto, Courbevoie (FR); Raphaëlle Barry-Martinet, La Crau (FR); Samuel Tozer, Paris (FR); Franck Maurinot, Issy-les-Moulineaux (FR); Karine Loulier-Le Franc, Paris (FR); Mickaël Le, Maisons Alfort (FR); Stéphane Nedelec, Montrouge (FR); Michel Cohen-Tannoudji, Montrouge (FR)

(73) Assignees: SORBONNE UNIVERSITE, Paris (FR); INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 1042 days.

(21) Appl. No.: 17/055,942

(22) PCT Filed: May 17, 2019

(86) PCT No.: PCT/EP2019/062877
§ 371 (c)(1),
(2) Date: Nov. 16, 2020

(87) PCT Pub. No.: WO2019/219947
PCT Pub. Date: Nov. 21, 2019

(65) Prior Publication Data
US 2021/0214747 A1 Jul. 15, 2021

(30) Foreign Application Priority Data
May 18, 2018 (EP) .................................... 18305623

(51) Int. Cl.
C12N 15/85 (2006.01)
C12N 9/12 (2006.01)
C12N 15/90 (2006.01)

(52) U.S. Cl.
CPC ........... *C12N 15/85* (2013.01); *C12N 9/1241* (2013.01); *C12N 15/907* (2013.01); *C12N 2800/90* (2013.01); *C12N 2830/001* (2013.01); *C12Y 207/07* (2013.01)

(58) Field of Classification Search
CPC .. C12N 15/85; C12N 9/1241; C12N 2800/90; C12N 2830/001; C12N 15/907; C12Y 207/07
See application file for complete search history.

(56) References Cited

U.S. PATENT DOCUMENTS

| | | | |
|---|---|---|---|
| 6,686,196 B2* | 2/2004 | Lieber | C12N 15/86 435/456 |
| 2015/0152406 A1* | 6/2015 | Grawunder | C12N 15/1055 506/17 |
| 2015/0291977 A1* | 10/2015 | Minshull | A61K 31/7105 435/320.1 |
| 2018/0265890 A1* | 9/2018 | Qian | C12N 5/16 |

FOREIGN PATENT DOCUMENTS

| | | |
|---|---|---|
| CN | 103014064 A | 4/2013 |
| CN | 104087613 B | 8/2017 |
| EP | 3 219 800 A1 | 9/2017 |
| WO | 2008/027384 A1 | 3/2008 |
| WO | 2017/054647 A1 | 4/2017 |

OTHER PUBLICATIONS

Chen et al (Pogostick: A New Versatile piggyBac Vector for Inducible Gene Over-Expression and Down-Regulation in Emerging Model Systems, PLoS ONE, vol. 6, Apr. 2011, pp. 1-8). (Year: 2011).*
Urschtiz et al. PNAS vol. 107, pp. 8117-8122 (Year: 2010).*
Ford, addgene Blog, "Plasmids 101: Restriction Cloning", Feb. 18, 2016, retrieved from the Internet: <URL: blog.addgene.org/plasmid-101-restriction-cloning>. (Year: 2016).*
International Preliminary Report on Patentability, mailed Nov. 24, 2020, issued in corresponding International Patent Application No. PCT/EP2019/062877, filed May 17, 2019, 8 pages.
Colella, P., et al., "Emerging Issues in AAV-Mediated In Vivo Gene Therapy," Molecular Therapy: Methods & Clinical Development Review 8:87-104, Dec. 2017.
Geurts, A.M., et al., "Gene Transfer into Genomes of Human Cells by the Sleeping Beauty Transposon System," Molecular Therapy: The Journal of the American Society of Gene Therapy 8(1):108-117, Jul. 2003.
International Search Report mailed Jun. 13, 2019, issued in International Patent Application No. PCT/EP2019/062877, filed May 17, 2019, 5 pages.

(Continued)

*Primary Examiner* — Brian Whiteman
*Assistant Examiner* — Stephanie L Sullivan
(74) *Attorney, Agent, or Firm* — Christensen O'Connor Johnson Kindness PLLC

(57) ABSTRACT

The disclosure is directed at providing molecular tools and methods for transgenes integration in the genome of host cells, in particular tools and method enabling a transposition-dependent expression of the transgene, thereby facilitating identification and selection of effectively transformed hosts.

8 Claims, 40 Drawing Sheets
Specification includes a Sequence Listing.

(56) References Cited

OTHER PUBLICATIONS

"PrecisionX (TM) HR Targeting Vectors," System Biosciences, 2014, <https://www.systembio.com/wp-content/uploads/PrecisionX_donor_vector_user20manual-WEB-1.pdf> [retrieved Oct. 10, 2018], pp. 1-66.
Written Opinion mailed Jun. 13, 2019, issued in International Patent Application No. PCT/EP2019/062877, filed May 17, 2019, 7 pages.

* cited by examiner

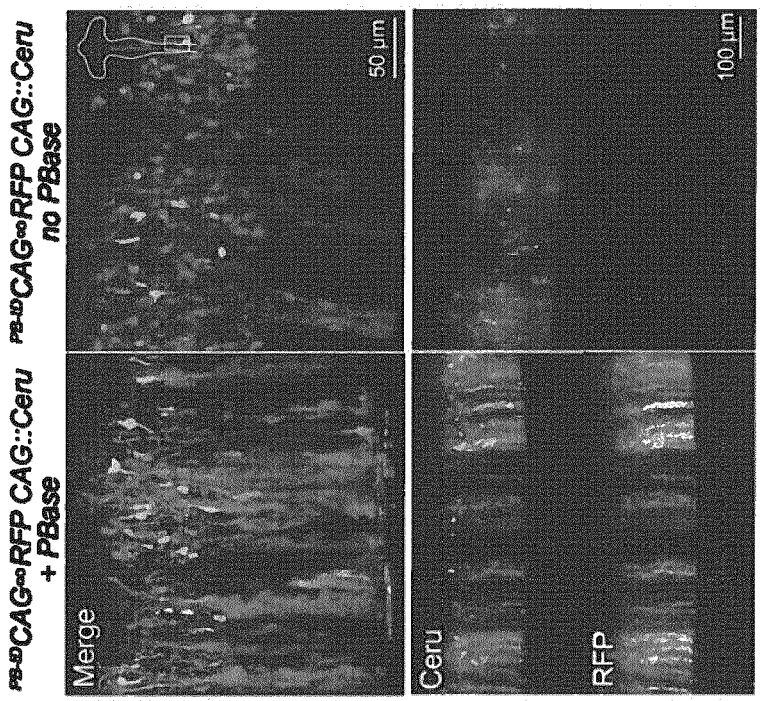
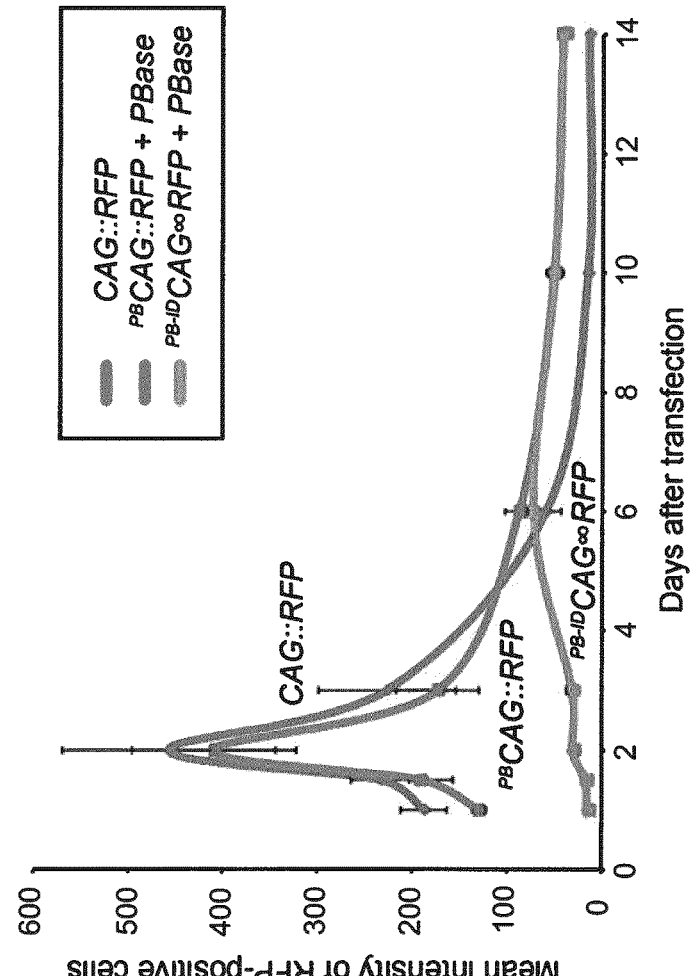
Figure 1C and D

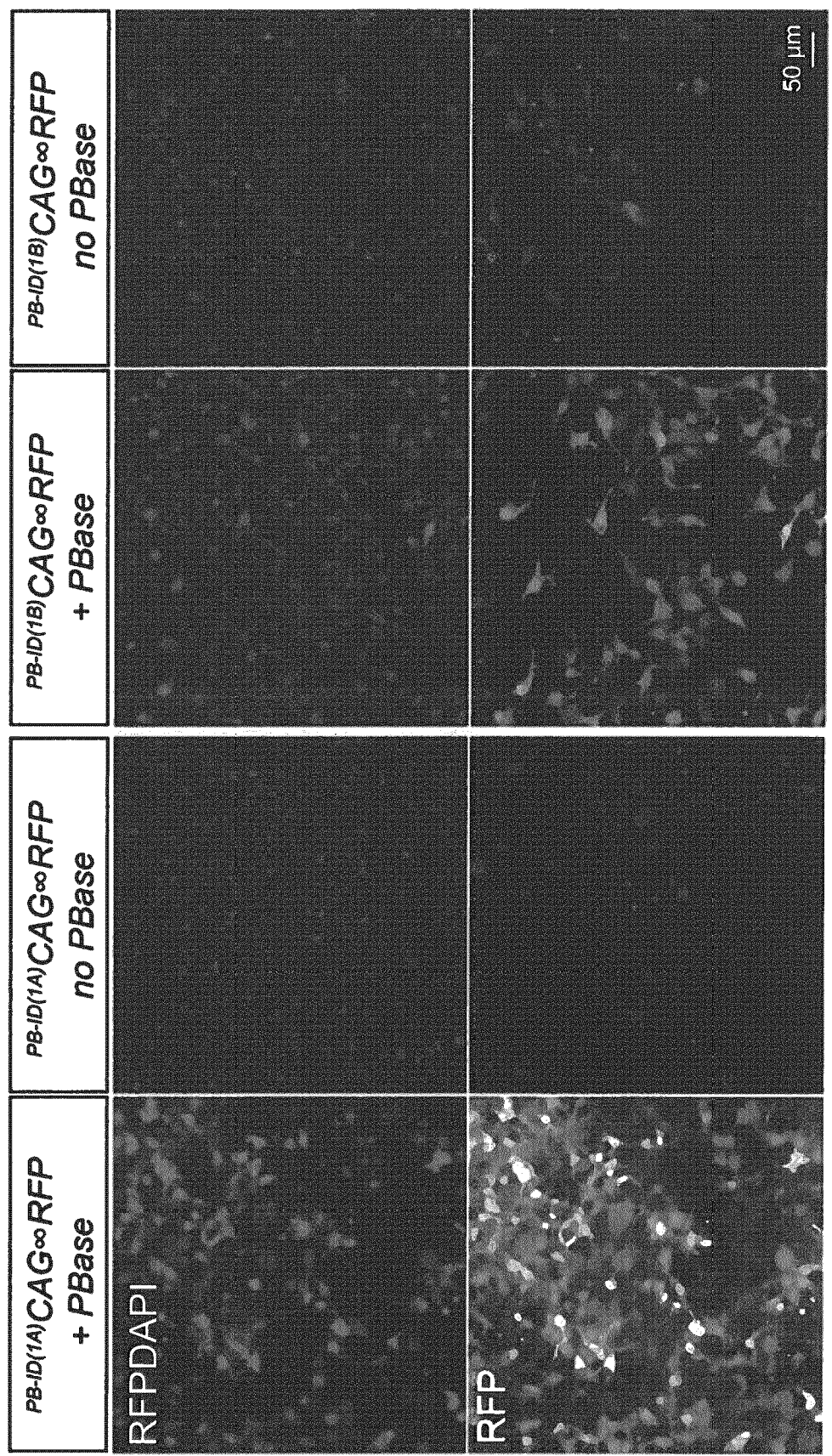
Figure 2B1

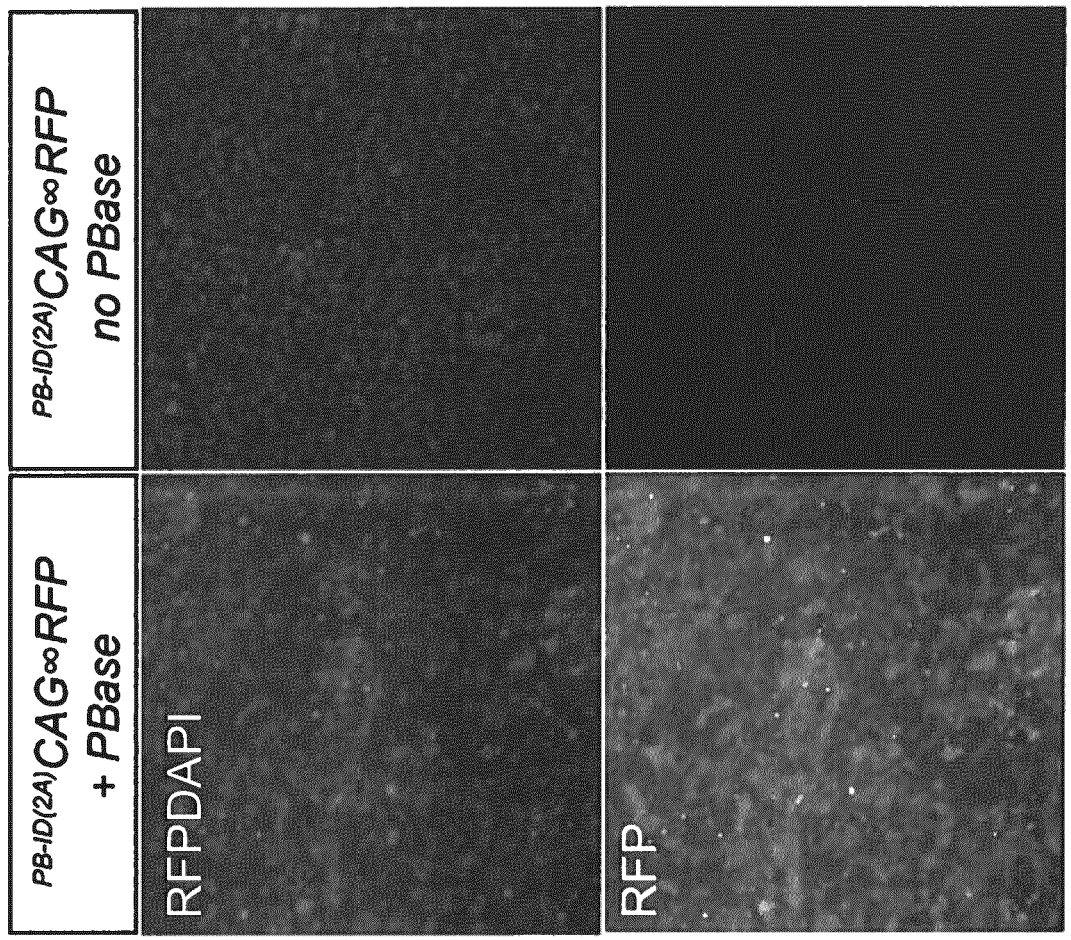
Figure 2B2

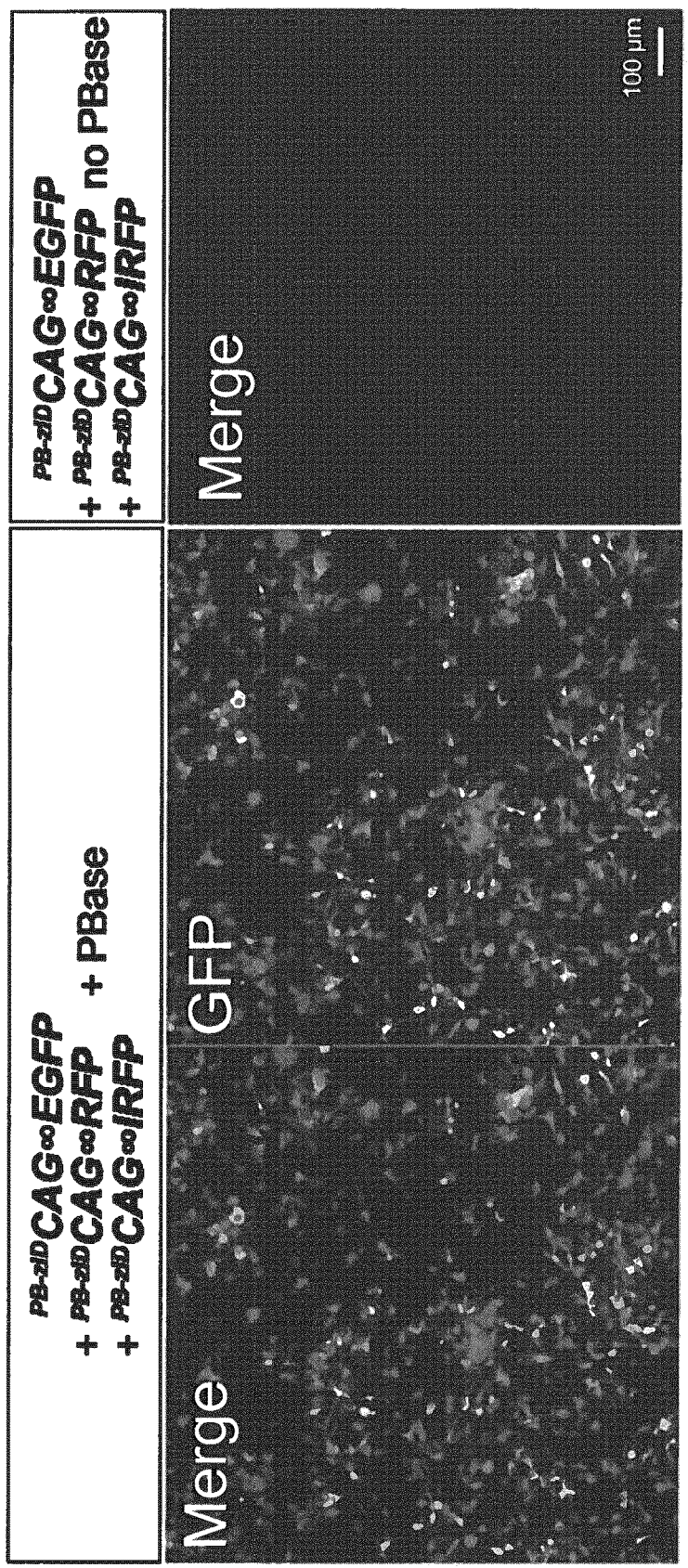
Figure 4B1

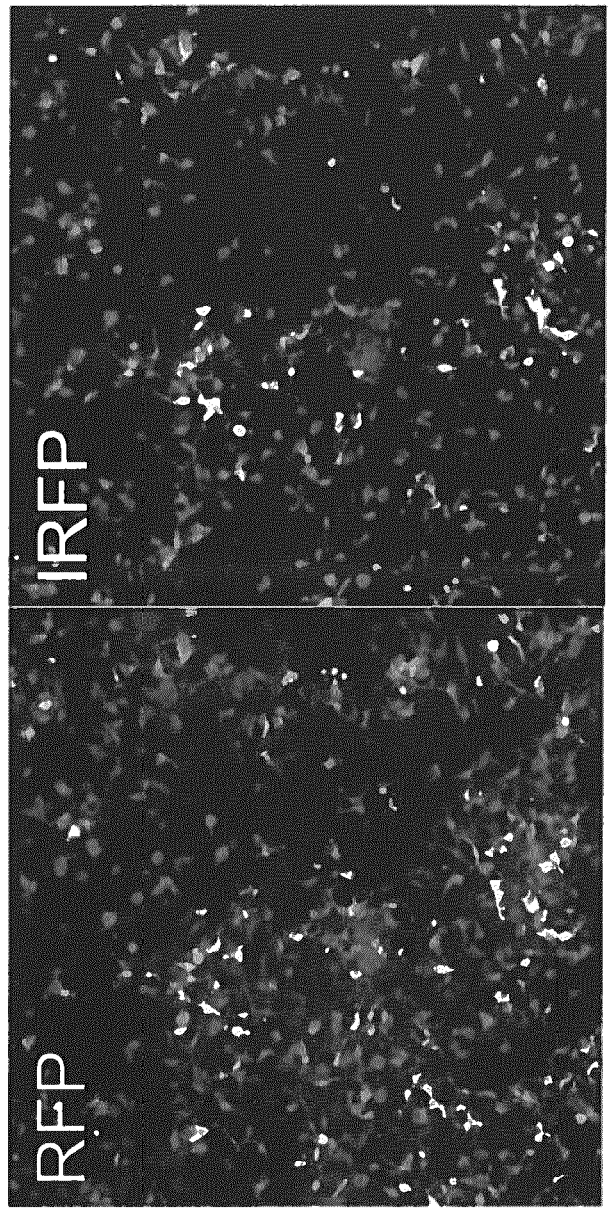
Figure 4B2

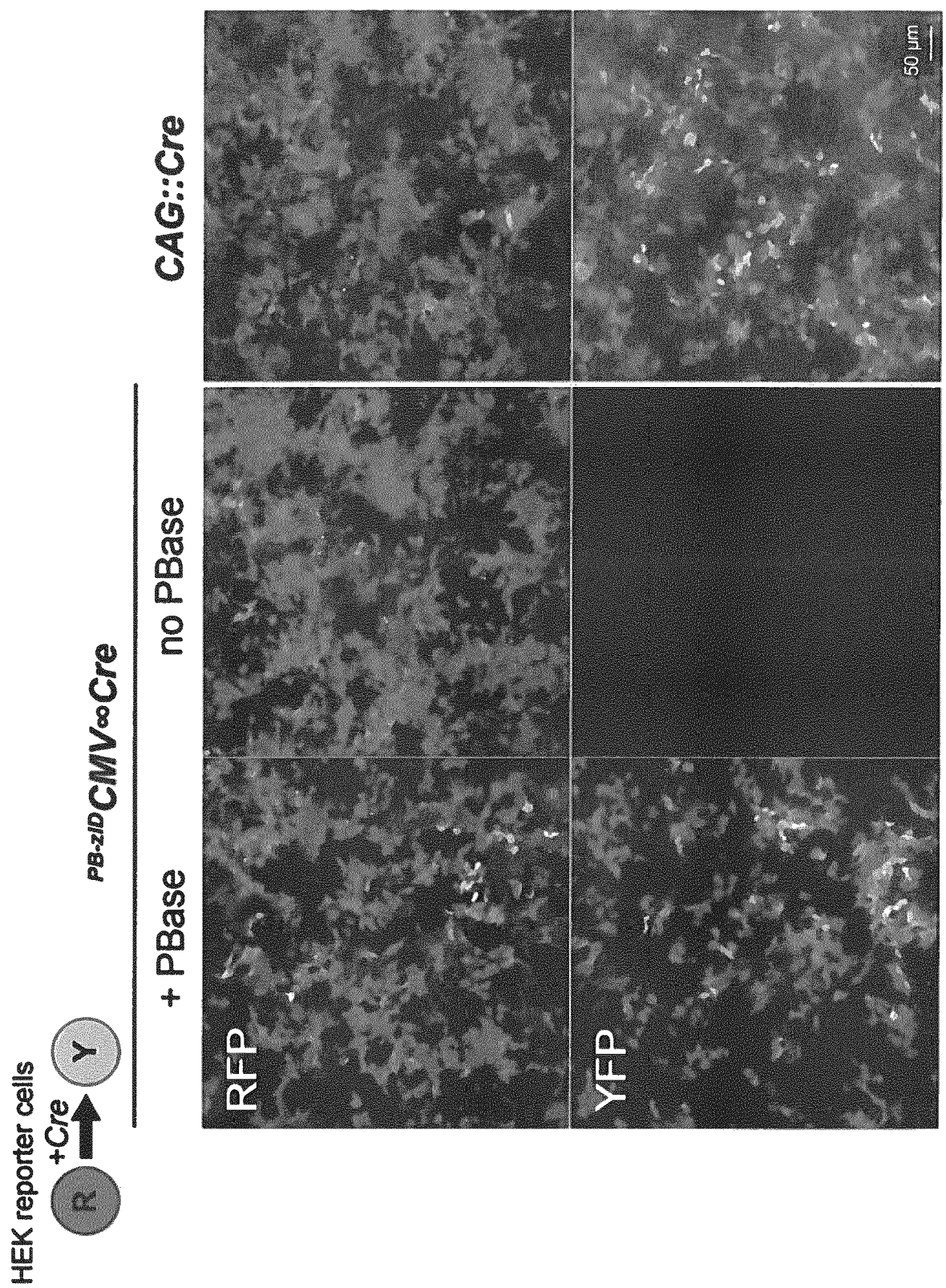
Figure 5B1

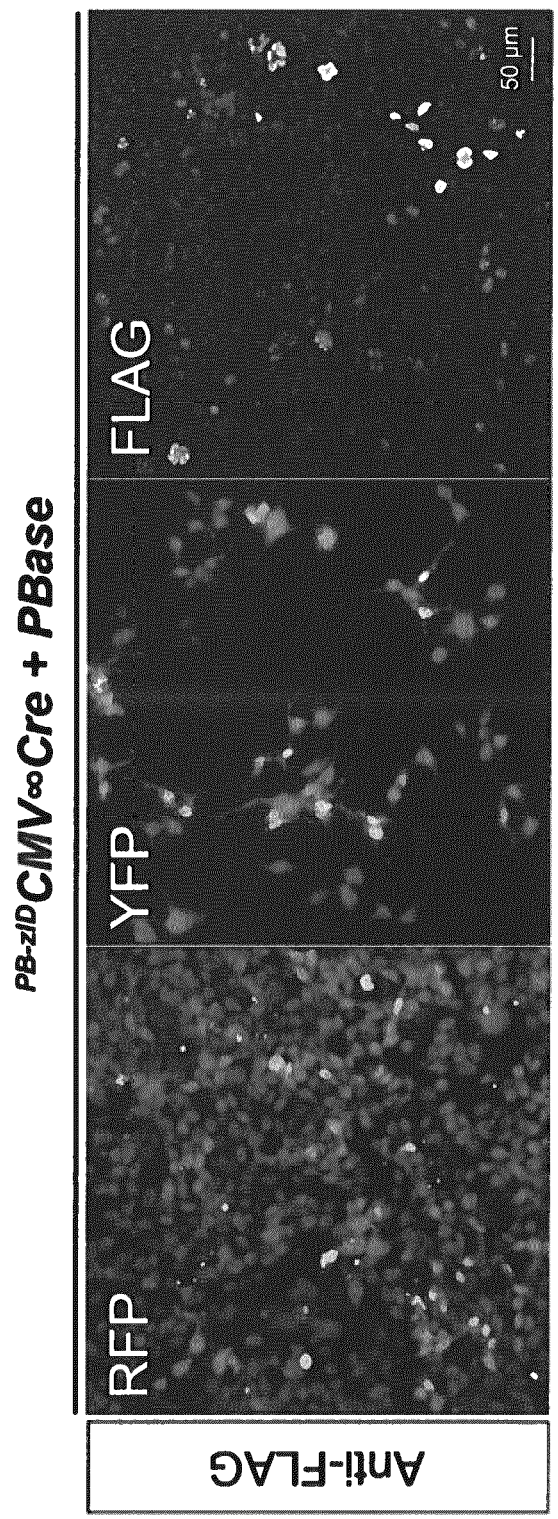
Figure 5B2

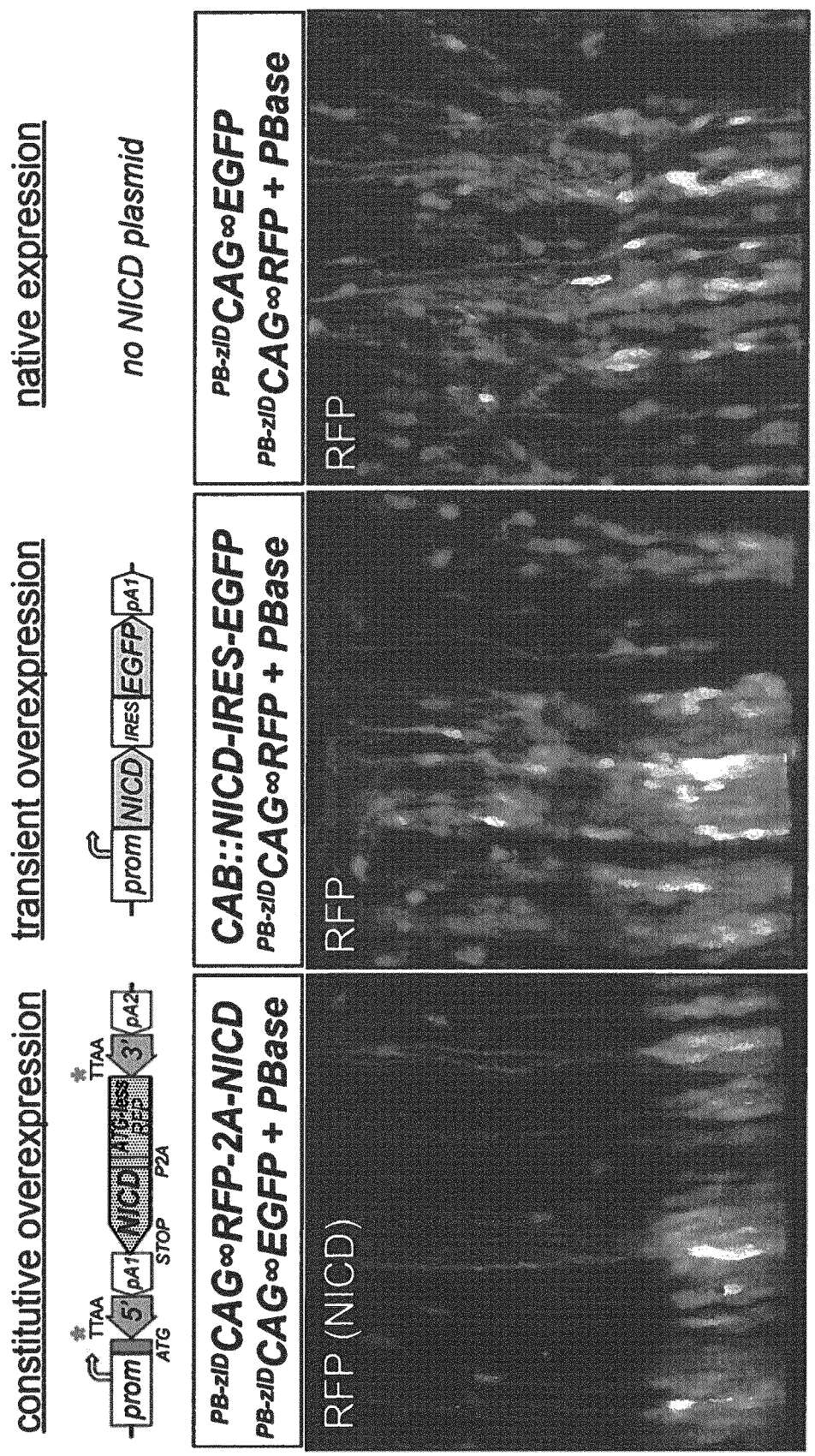
Figure 7A1

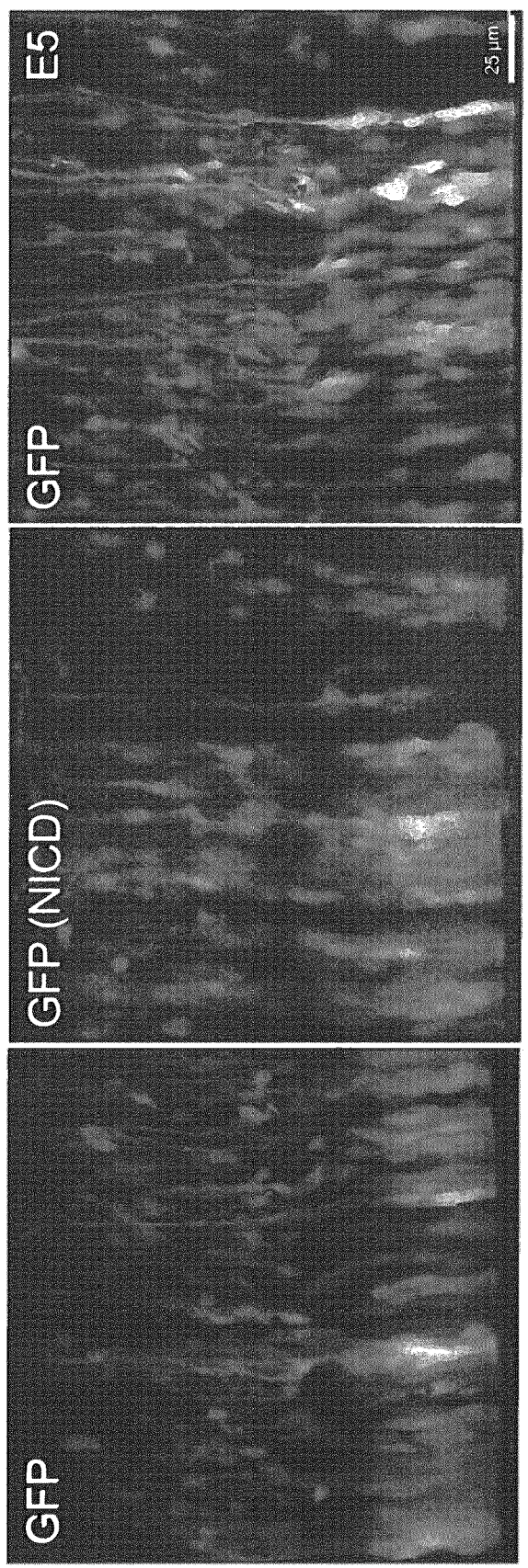
Figure 7A2

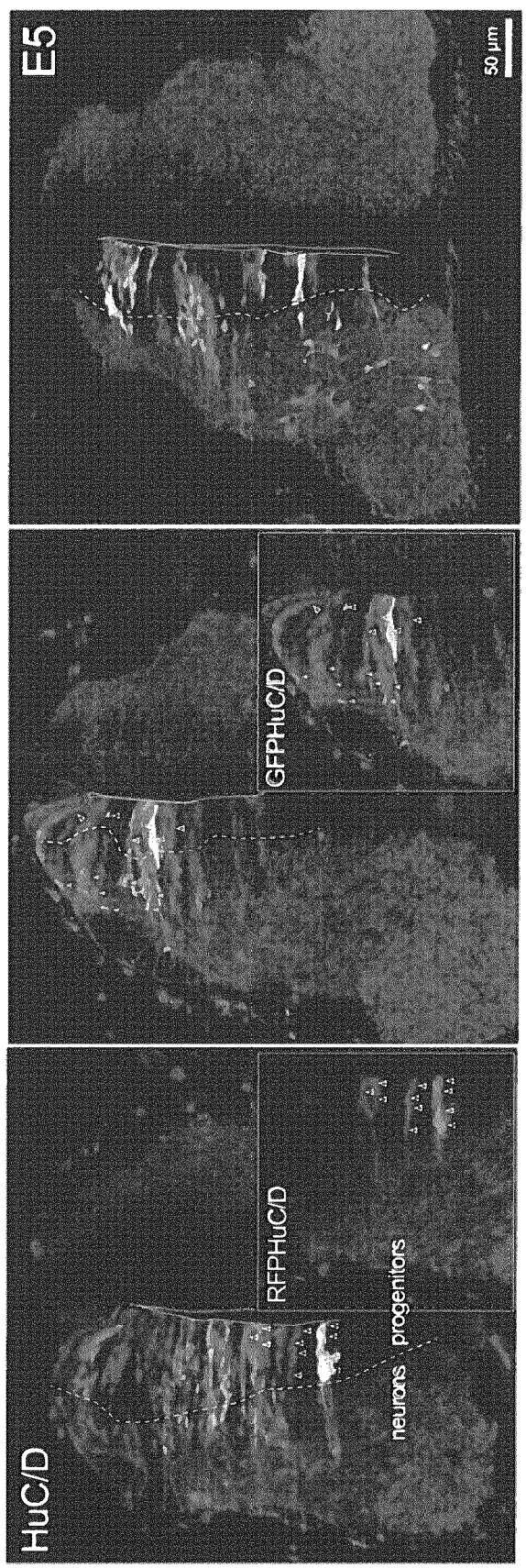
Figure 7A3

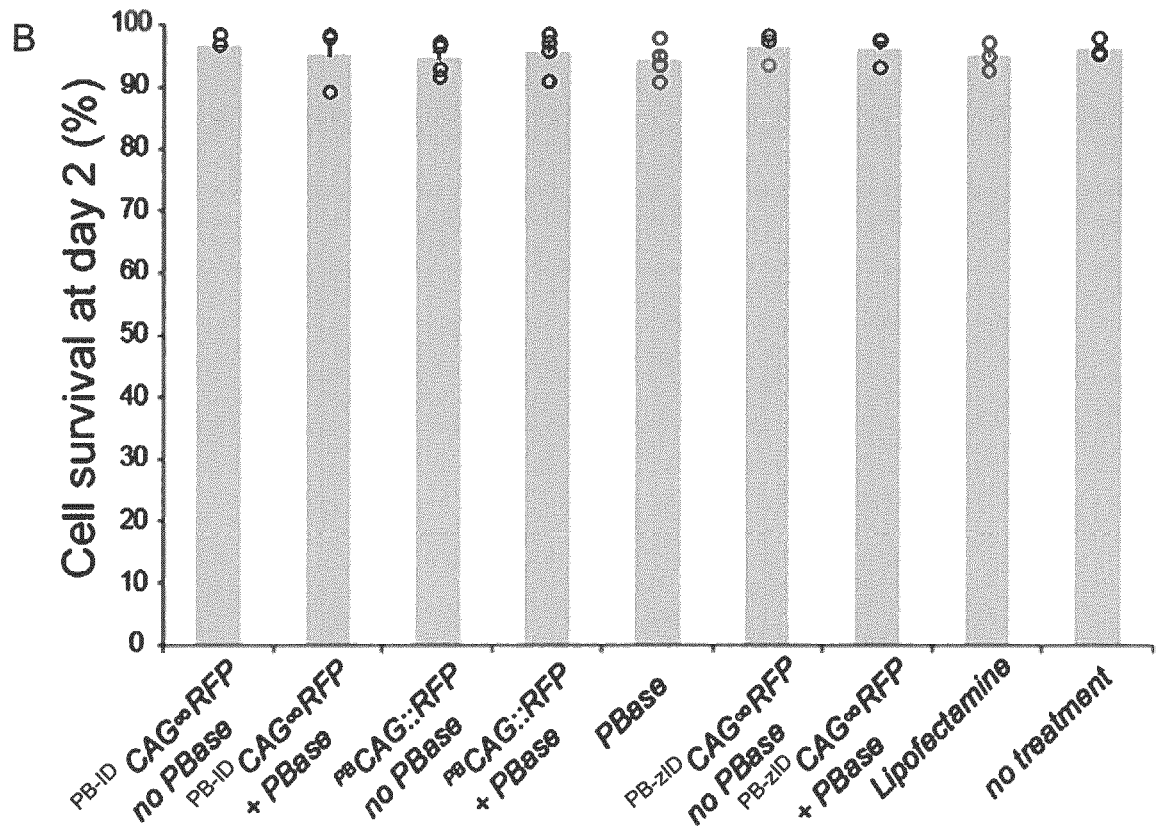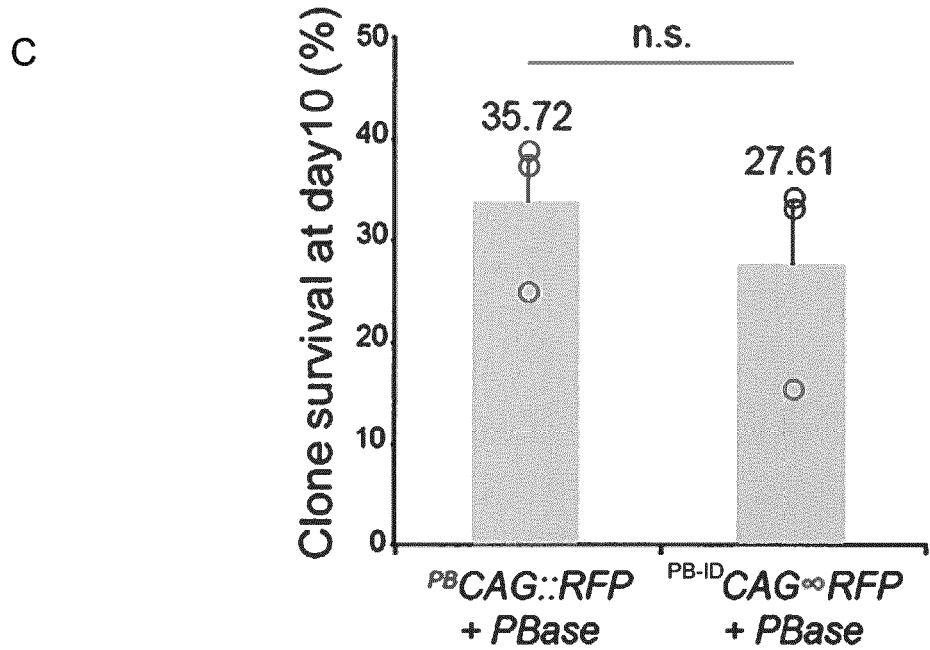

SEQ ID NO: 13 – Sequence of PB-CAG::RFP (part 1: from nucleotide 1 to nucleotide 3000)

```
   1 TCAATCTAAA GTATATATGA GTAAACTTGG TCTGACAGTT ACCAATGCTT AATCAGTGAG
  61 GCACCTATCT CAGCGATCTG TCTATTTCGT TCATCCATAG TTGCCTGACT CCCCGTCGTG
 121 TAGATAACTA CGATACGGGA GGGCTTACCA TCTGGCCCCA GTGCTGCAAT GATACCGCGA
 181 GACCCACGCT CACCGGCTCC AGATTTATCA GCAATAAACC AGCCAGCCGG AAGGGCCGAG
 241 CGCAGAAGTG GTCCTGCAAC TTTATCCGCC TCCATCCAGT CTATTAATTG TTGCCGGGAA
 301 GCTAGAGTAA GTAGTTCGCC AGTTAATAGT TTGCGCAACG TTGTTGCCAT TGCTACAGGC
 361 ATCGTGGTGT CACGCTCGTC GTTTGGTATG GCTTCATTCA GCTCCGGTTC CCAACGATCA
 421 AGGCGAGTTA CATGATCCCC CATGTTGTGC AAAAAAGCGG TTAGCTCCTT CGGTCCTCCG
 481 ATCGTTGTCA GAAGTAAGTT GGCCGCAGTG TTATCACTCA TGGTTATGGC AGCACTGCAT
 541 AATTCTCTTA CTGTCATGCC ATCCGTAAGA TGCTTTTCTG TGACTGGTGA GTACTCAACC
 601 AAGTCATTCT GAGAATAGTG TATGCGGCGA CCGAGTTGCT CTTGCCCGGC GTCAATACGG
 661 GATAATACCG CGCCACATAG CAGAACTTTA AAAGTGCTCA TCATTGGAAA ACGTTCTTCG
 721 GGGCGAAAAC TCTCAAGGAT CTTACCGCTG TTGAGATCCA GTTCGATGTA ACCCACTCGT
 781 GCACCCAACT GATCTTCAGC ATCTTTTACT TTCACCAGCG TTTCTGGGTG AGCAAAAACA
 841 GGAAGGCAAA ATGCCGCAAA AAAGGGAATA AGGGCGACAC GGAAATGTTG AATACTCATA
 901 CTCTTCCTTT TTCAATATTA TTGAAGCATT TATCAGGGTT ATTGTCTCAT GAGCGGATAC
 961 ATATTTGAAT GTATTTAGAA AAATAAACAA ATAGGGGTTC CGCGCACATT TCCCCGAAAA
1021 GTGCCACCTG ACGTCCCAAT GATATCATTT AAATATCGAT TTAACCCTAG AAAGATAGTC
1081 TGCGTAAAAT TGACGCATGC ATAGCGCTAT TAATGTCGAC ACTAGTTCAG GTCGACATTG
1141 ATTATTGACT AGTTATTAAT AGTAATCAAT TACGGGGTCA TTAGTTCATA GCCCATATAT
1201 GGAGTTCCGC GTTACATAAC TTACGGTAAA TGGCCCGCCT GGCTGACCGC CCAACGACCC
1261 CCGCCCATTG ACGTCAATAA TGACGTATGT TCCCATAGTA ACGCCAATAG GGACTTTCCA
1321 TTGACGTCAA TGGGTGGACT ATTTACGGTA AACTGCCCAC TTGGCAGTAC ATCAAGTGTA
1381 TCATATGCCA AGTACGCCCC CTATTGACGT CAATGACGGT AAATGGCCCG CCTGGCATTA
1441 TGCCCAGTAC ATGACCTTAT GGGACTTTCC TACTTGGCAG TACATCTACG TATTAGTCAT
1501 CGCTATTACC ATGGGTCGAG GTGAGCCCCA CGTTCTGCTT CACTCTCCCC ATCTCCCCCC
1561 CCTCCCCACC CCCAATTTTG TATTTATTTA TTTTTTAATT ATTTTGTGCA GCGATGGGGG
1621 CGGGGGGGGG GGGGCGCGC GCCAGGCGGG GCGGGCGGG GCGAGGGGCG GGGCGGGGCG
1681 AGGCGGAGAG GTGCGGCGGC AGCCAATCAG AGCGGCGCGC TCCGAAAGTT TCCTTTTATG
1741 GCGAGGCGGC GGCGGCGGCG GCCCTATAAA AAGCGAAGCG CGCGGCGGGC GGGAGTCGCT
1801 GCGTTGCCTT CGCCCCGTGC CCCGCTCCGC GCCGCCTCGC GCCGCCCGCC CCGGCTCTGA
1861 CTGACCGCGT TACTCCCACA GGTGAGCGGG CGGGACGGCC CTTCTCCTCC GGGCTGTAAT
1921 TAGCGCTTGG TTTAATGACG GCTCGTTTCT TTTCTGTGGC TGCGTGAAAG CCTTAAAGGG
1981 CTCCGGGAGG GCCCTTTGTG CGGGGGGAG CGGCTCGGGG GGTGCGTGCG TGTGTGTGTG
2041 CGTGGGGAGC GCCGCGTGCG GCCCGCGCTG CCCGGCGGCT GTGAGCGCTG CGGGCGCGGC
2101 GCGGGGCTTT GTGCGCTCCG CGTGTGCGCG AGGGGAGCGC GGCCGGGGC GGTGCCCCGC
2161 GGTGCGGGGG GCTGCGAGG GGAACAAAGG CTGCGTGCGG GGTGTGTGCG TGGGGGGTG
2221 AGCAGGGGGT GTGGGCGCGG CGGTCGGGCT GTAACCCCCC CCTGCACCCC CCTCCCCGAG
2281 TTGCTGAGCA CGGCCCGGCT TCGGGTGCGG GGCTCCGTGC GGGGCGTGGC GCGGGGCTCG
2341 CCGTGCCGGG CGGGGGGTGG CGGCAGGTGG GGGTGCCGGG CGGGGCGGGG CCGCCTCGGG
2401 CCGGGGAGGG CTCGGGGGAG GGGCGCGGCG GCCCCGGAGC GCCGGCGGCT GTCGAGGCGC
2461 GGCGAGCCGC AGCCATTGCC TTTTATGGTA ATCGTGCGAG AGGGCGCAGG GACTTCCTTT
2521 GTCCCAAATC TGGCGGAGCC GAAATCTGGG AGGCGCCGCC GCACCCCTC TAGCGGGCGC
2581 GGGCGAAGCG GTGCGGCGCC GGCAGGAAGG AAATGGGCGG GAGGGCCTT CGTGCGTCGC
2641 CGCGCCGCCG TCCCCTTCTC CATCTCCAGC CTCGGGGCTG CCGCAGGGGG ACGGCTGCCT
2701 TCGGGGGGA CGGGGCAGGG CGGGGTTCGG CTTCTGGCGT GTGACCGGCG GCTCTAGAGC
2761 CTCTGCTAAC CATGTTCATG CCTTCTTCTT TTTCCTACAG CTCCTGGGCA ACGTGCTGGT
2821 TGTTGTGCTG TCTCATCATT TTGGCAAAGA ATTCATGGCC TCCTCCGAGG ACGTCATCAA
2881 GGAGTTCATG CGCTTCAAGG TGCGCATGGA GGGCTCCGTG AACGGCCACG AGTTCGAGAT
2941 CGAGGGCGAG GGCGAGGGCC GCCCCTACGA GGGCACCCAG ACCGCAAGC TGAAGGTGAC
```

Figure 14B1

SEQ ID NO: 13 – Sequence of PB-CAG::RFP (part 2: from nucleotide 3001 to nucleotide 4661)

```
3001 CAAGGGCGGC CCCCTGCCCT TCGCCTGGGA CATCCTGTCC CCTCAGTTCC AGTACGGCTC
3061 CAAGGCCTAC GTGAAGCACC CCGCCGACAT CCCCGACTAC TTGAAGCTGT CCTTCCCCGA
3121 GGGCTTCAAG TGGGAGCGCG TGATGAACTT CGAGGACGGC GGCGTGGTGA CCGTGACCCA
3181 GGACTCCTCC CTGCAGGACG GCGAGTTCAT CTACAAGGTG AAGCTGCGCG GCACCAACTT
3241 CCCCTCCGAC GGCCCCGTAA TGCAGAAGAA GACCATGGGC TGGGAGGCCT CCACCGAGCG
3301 GATGTACCCC GAGGACGGCG CCCTGAAGGG CGAGATCAAG ATGAGGCTGA AGCTGAAGGA
3361 CGGCGGCCAC TACGACGCCG AGGTCAAGAC CACCTACATG GCCAAGAAGC CCGTGCAGCT
3421 GCCCGGCGCC TACAAGACCG ACATCAAGCT GGACATCACC TCCCACAACG AGGACTACAC
3481 CATCGTGGAA CAGTACGAGC GCGCCGAGGG CCGCCACTCC ACCGGCGCCT AACTGCAGAT
3541 CTGCGGCCGC TACGTATCGA CTTTAGTGCC TTCTAGTTGC CAGCCATCTG TTGTTTGCCC
3601 CTCCCCCGTG CCTTCCTTGA CCCTGGAAGG TGCCACTCTC ACTGTCCTTT CCTAATAAAA
3661 TGAGGAAATT GCATCGCATT GTCTGAGTAG GTGTCATTCT ATTCTGGGGG GTGGGGTGGG
3721 GCAGGACAGC AAGGGGGAGG ATTGGGAAGA CAATAGCAGG CATGCTGGGG GTTTAAACCT
3781 TAAG**CATGCG TCAATTTTAC GCATGATTAT CTTTAACGTA CGTCACAATA TGATTATCTT
3841 TCTAGGGTTA A**ACGCGTATT TAAATCGATA TCGGAAAGAA CATGTGAGCA AAAGGCCAGC
3901 AAAAGGCCAG GAACCGTAAA AAGGCCGCGT TGCTGGCGTT TTTCCATAGG CTCCGCCCCC
3961 CTGACGAGCA TCACAAAAAT CGACGCTCAA GTCAGAGGTG GCGAAACCCG ACAGGACTAT
4021 AAAGATACCA GGCGTTTCCC CCTGGAAGCT CCCTCGTGCG CTCTCCTGTT CCGACCCTGC
4081 CGCTTACCGG ATACCTGTCC GCCTTTCTCC CTTCGGGAAG CGTGGCGCTT TCTCATAGCT
4141 CACGCTGTAG GTATCTCAGT TCGGTGTAGG TCGTTCGCTC CAAGCTGGGC TGTGTGCACG
4201 AACCCCCCGT TCAGCCCGAC CGCTGCGCCT TATCCGGTAA CTATCGTCTT GAGTCCAACC
4261 CGGTAAGACA CGACTTATCG CCACTGGCAG CAGCCACTGG TAACAGGATT AGCAGAGCGA
4321 GGTATGTAGG CGGTGCTACA GAGTTCTTGA AGTGGTGGCC TAACTACGGC TACACTAGAA
4381 GAACAGTATT TGGTATCTGC GCTCTGCTGA AGCCAGTTAC CTTCGGAAAA AGAGTTGGTA
4441 GCTCTTGATC CGGCAAACAA ACCACCGCTG GTAGCGGTGG TTTTTTTGTT TGCAAGCAGC
4501 AGATTACGCG CAGAAAAAAA GGATCTCAAG AAGATCCTTT GATCTTTTCT ACGGGGTCTG
4561 ACGCTCAGTG AACGAAAAC TCACGTTAAG GGATTTTGGT CATGAGATTA TCAAAAAGGA
4621 TCTTCACCTA GATCCTTTTA AATTAAAAAT GAAGTTTTAA A
```

Figure 14B2

SEQ ID NO: 14 – Sequence of PB-IDCAG∞RFP (part 1: from nucleotide 1 to nucleotide 3000)

```
   1 GGCGCGCGCC AGGCGGGGCG GGCGGGGCG AGGGGCGGGG CGGGGCGAGG CGGAGAGGTG
  61 CGGCGGCAGC CAATCAGAGC GGCGCGCTCC GAAAGTTTCC TTTTATGGCG AGGCGGCGGC
 121 GGCGGCGGCC CTATAAAAAG CGAAGCGCGC GGCGGGCGGG AGTCGCTGCG TTGCCTTCGC
 181 CCCGTGCCCC GCTCCGCGCC GCCTCGCGCC GCCCGCCCCG GCTCTGACTG ACCGCGTTAC
 241 TCCCACAGGT GAGCGGGCGG GACGGCCCTT CTCCTCCGGG CTGTAATTAG CGCTTGGTTT
 301 AATGACGGCT CGTTTCTTTT CTGTGGCTGC GTGAAAGCCT TAAAGGGCTC CGGGAGGGCC
 361 CTTTGTGCGG GGGGAGCGG CTCGGGGGGT GCGTGCGTGT GTGTGTGCGT GGGGAGCGCC
 421 GCGTGCGGCC CGCGCTGCCC GGCGGCTGTG AGCGCTGCGG GCGCGGCGCG GGCTTTGTG
 481 CGCTCCGCGT GTGCGCGAGG GGAGCGCGGC CGGGGCGGT GCCCGCGGT GCGGGGGGC
 541 TGCGAGGGGA ACAAAGGCTG CGTGCGGGGT GTGTGCGTGG GGGGTGAGC AGGGGGTGTG
 601 GGCGCGGCGG TCGGGCTGTA ACCCCCCCCT GCACCCCCCT CCCCGAGTTG CTGAGCACGG
 661 CCCGGCTTCG GGTGCGGGGC TCCGTGCGGG GCGTGGCGCG GGGCTCGCCG TGCCGGGCGG
 721 GGGGTGGCGG CAGGTGGGGG TGCCGGGCGG GGCGGGGCCG CCTCGGGCCG GGGAGGGCTC
 781 GGGGGAGGGG CGCGGCGGCC CCGGAGCGCC GGCGGCTGTC GAGGCGCGGC GAGCCGCAGC
 841 CATTGCCTTT TATGGTAATC GTGCGAGAGG GCGCAGGGAC TTCCTTTGTC CCAAATCTGG
 901 CGGAGCCGAA ATCTGGGAGG CGCCGCCGCA CCCCTCTAG CGGGCGCGGG CGAAGCGGTG
 961 CGGCGCCGGC AGGAAGGAAA TGGGCGGGGA GGGCCTTCGT GCGTCGCCGC GCCGCCGTCC
1021 CCTTCTCCAT CTCCAGCCTC GGGGCTGCCG CAGGGGGACG GCTGCCTTCG GGGGGGACGG
1081 GGCAGGGCGG GGTTCGGCTT CTGGCGTGTG ACCGGCGGCT CTAGAGCCTC TGCTAACCAT
1141 GTTCATGCCT TCTTCTTTTT CCTACAGCTC CTGGGCAACG TGCTGGTTGT TGTGCTGTCT
1201 CATCATTTTG GCAAGAATT CTCGCGATTA ACCCTAGAAA GATAGTCTGC GTAAAATTGA
1261 CGCATGCATC AATTGTAACT GCGGTTTAAA CTCCCCAGCA TGCCTGCTAT TGTCTTCCCA
1321 ATCCTCCCCC TTGCTGTCCT GCCCCACCCC ACCCCCCAGA ATAGAATGAC ACCTACTCAG
1381 ACAATGCGAT GCAATTTCCT CATTTTATTA GGAAAGGACA GTGAGAGTGG CACCTTCCAG
1441 GGTCAAGGAA GGCACGGGGG AGGGCAAAC AACAGATGGC TGGCAACTAG AAGGCACTAA
1501 AGTCGGATCC TCGACAATTG GATATCTTAG GCGCCGGTGG AGTGGCGGCC CTCGGCGCGC
1561 TCGTACTGTT CCACGATGGT GTAGTCCTCG TTGTGGGAGG TGATGTCCAG CTTGATGTCG
1621 GTCTTGTAGG CGCCGGGCAG CTGCACGGGC TTCTTGGCCA TGTAGGTGGT CTTGACCTCG
1681 GCGTCGTAGT GGCCGCCGTC CTTCAGCTTC AGCCTCATCT TGATCTCGCC CTTCAGGGCG
1741 CCGTCCTCGG GGTACATCCG CTCGGTGGAG GCCTCCCAGC CATGGTCTT CTTCTGCATT
1801 ACGGGGCCGT CGGAGGGAA GTTGGTGCCG CGCAGCTTCA CCTTGTAGAT GAACTCGCCG
1861 TCCTGCAGGG AGGAGTCCTG GGTCACGGTC ACCACGCCGC CGTCCTCGAA GTTCATCACG
1921 CGCTCCCACT TGAAGCCCTC GGGGAAGGAC AGCTTCAAGT AGTCGGGGAT GTCGGCGGGG
1981 TGCTTCACGT AGGCCTTGGA GCCGTACTGG AACTGAGGGG ACAGGATGTC CCAGGCGAAG
2041 GGCAGGGGGC CGCCCTTGGT CACCTTCAGC TTGGCGGTCT GGGTGCCCTC GTAGGGGCGG
2101 CCCTCGCCCT CGCCCTCGAT CTCGAACTCG TGGCCGTTCA CGGAGCCCTC CATGCGCACC
2161 TTGAAGCGCA TGAACTCCTT GATGACGTCC TCGGAGGAGG CCATGGTGGC GATATCGCTA
2221 GGCCCGGGCT AATCACTTAA TTAACCCTAG AAAGATAATC ATATTGTGAC GTACGTTAAA
2281 GATAATCATG CGTAAAATTG ACGCATGTCC GGAGCCGTAG ATATCGGAAA GAAAGCGGCC
2341 GCTGCAGGTC GAGGGATCTT CATAAGAGAA GAGGGACAGC TATGACTGGG AGTAGTCAGG
2401 AGAGGAGGAA AAATCTGGCT AGTAAAACAT GTAAGGAAAA TTTTAGGGAT GTTAAAGAAA
2461 AAAATAACAC AAAACAAAAT ATAAAAAAAA TCTAACCTCA AGTCAAGGCT TTTCTATGGA
2521 ATAAGGAATG GACAGCAGGG GGCTGTTTCA TATACTGATG ACCTCTTTAT AGCCACCTTT
2581 GTTCATGGCA GCCAGCATAT GGCATATGTT GCCAAACTCT AAACCAAATA CTCATTCTGA
2641 TGTTTTAAAT GATTTGCCCT CCCATATGTC CTTCCGAGTG AGAGACACAA AAAATTCCAA
2701 CACACTATTG CAATGAAAAT AAATTTCCTT TATTAGCCAG AAGTCAGATG CTCAAGGGGC
2761 TTCATGATGT CCCCATAATT TTTGGCAGAG GGAAAAGAT CTCAGTGGTA TTTGTGAGCC
2821 AGGGCATTGG CCACACCAGC CACCACCTTC TGATAGGCAG CCTGCACCTG AGGAGTGAAT
2881 TAGAAGCTTT GAGCAAAAGG CCAGCAAAAG GCCAGGAACC GTAAAAAGGC CGCGTTGCTG
2941 GCGTTTTTCC ATAGGCTCCG CCCCCCTGAC GAGCATCACA AAAATCGACG CTCAAGTCAG
```

Figure 15B1

SEQ ID NO: 14 – Sequence of PB-IDCAG∞RFP (part 2: from nucleotide 3001 to nucleotide 5223)

```
3001 AGGTGGCGAA ACCCGACAGG ACTATAAAGA TACCAGGCGT TTCCCCCTGG AAGCTCCCTC
3061 GTGCGCTCTC CTGTTCCGAC CCTGCCGCTT ACCGGATACC TGTCCGCCTT TCTCCCTTCG
3121 GGAAGCGTGG CGCTTTCTCA TAGCTCACGC TGTAGGTATC TCAGTTCGGT GTAGGTCGTT
3181 CGCTCCAAGC TGGGCTGTGT GCACGAACCC CCCGTTCAGC CCGACCGCTG CGCCTTATCC
3241 GGTAACTATC GTCTTGAGTC CAACCCGGTA AGACACGACT TATCGCCACT GGCAGCAGCC
3301 ACTGGTAACA GGATTAGCAG AGCGAGGTAT GTAGGCGGTG CTACAGAGTT CTTGAAGTGG
3361 TGGCCTAACT ACGGCTACAC TAGAAGAACA GTATTTGGTA TCTGCGCTCT GCTGAAGCCA
3421 GTTACCTTCG GAAAAAGAGT TGGTAGCTCT TGATCCGGCA AACAAACCAC CGCTGGTAGC
3481 GGTGGTTTTT TTGTTTGCAA GCAGCAGATT ACGCGCAGAA AAAAAGGATC TCAAGAAGAT
3541 CCTTTGATCT TTTCTACGGG GTCTGACGCT CAGTGGAACG AAAACTCACG TTAAGGGATT
3601 TTGGTCATGA GATTATCAAA AAGGATCTTC ACCTAGATCC TTTTAAATTA AAAATGAAGT
3661 TTTAAATCAA TCTAAAGTAT ATATGAGTAA ACTTGGTCTG ACAGTTACCA ATGCTTAATC
3721 AGTGAGGCAC CTATCTCAGC GATCTGTCTA TTTCGTTCAT CCATAGTTGC CTGACTCCCC
3781 GTCGTGTAGA TAACTACGAT ACGGGAGGGC TTACCATCTG GCCCCAGTGC TGCAATGATA
3841 CCGCGAGACC CACGCTCACC GGCTCCAGAT TTATCAGCAA TAAACCAGCC AGCCGGAAGG
3901 GCCGAGCGCA GAAGTGGTCC TGCAACTTTA TCCGCCTCCA TCCAGTCTAT TAATTGTTGC
3961 CGGGAAGCTA GAGTAAGTAG TTCGCCAGTT AATAGTTTGC GCAACGTTGT TGCCATTGCT
4021 ACAGGCATCG TGGTGTCACG CTCGTCGTTT GGTATGGCTT CATTCAGCTC CGGTTCCCAA
4081 CGATCAAGGC GAGTTACATG ATCCCCCATG TTGTGCAAAA AAGCGGTTAG CTCCTTCGGT
4141 CCTCCGATCG TTGTCAGAAG TAAGTTGGCC GCAGTGTTAT CACTCATGGT TATGGCAGCA
4201 CTGCATAATT CTCTTACTGT CATGCCATCC GTAAGATGCT TTTCTGTGAC TGGTGAGTAC
4261 TCAACCAAGT CATTCTGAGA ATAGTGTATG CGGCGACCGA GTTGCTCTTG CCCGGCGTCA
4321 ATACGGGATA ATACCGCGCC ACATAGCAGA ACTTTAAAAG TGCTCATCAT TGGAAAACGT
4381 TCTTCGGGGC GAAAACTCTC AAGGATCTTA CCGCTGTTGA GATCCAGTTC GATGTAACCC
4441 ACTCGTGCAC CCAACTGATC TTCAGCATCT TTTACTTTCA CCAGCGTTTC TGGGTGAGCA
4501 AAAACAGGAA GGCAAAATGC CGCAAAAAAG GGAATAAGGG CGACACGGAA ATGTTGAATA
4561 CTCATACTCT TCCTTTTTCA ATATTATTGA AGCATTTATC AGGGTTATTG TCTCATGAGC
4621 GGATACATAT TTGAATGTAT TTAGAAAAAT AAACAAATAG GGGTTCCGCG CACATTTCCC
4681 CGAAAAGTGC CACCTGACGT CCCAATGATA TCATTTAAAT GTCGACATTG ATTATTGACT
4741 AGTTATTAAT AGTAATCAAT TACGGGGTCA TTAGTTCATA GCCCATATAT GGAGTTCCGC
4801 GTTACATAAC TTACGGTAAA TGGCCCGCCT GGCTGACCGC CCAACGACCC CCGCCCATTG
4861 ACGTCAATAA TGACGTATGT TCCCATAGTA ACGCCAATAG GGACTTTCCA TTGACGTCAA
4921 TGGGTGGACT ATTTACGGTA AACTGCCCAC TTGGCAGTAC ATCAAGTGTA TCATATGCCA
4981 AGTACGCCCC CTATTGACGT CAATGACGGT AAATGGCCCG CCTGGCATTA TGCCCAGTAC
5041 ATGACCTTAT GGGACTTTCC TACTTGGCAG TACATCTACG TATTAGTCAT CGCTATTACC
5101 ATGGGTCGAG GTGAGCCCCA CGTTCTGCTT CACTCTCCCC ATCTCCCCCC CCTCCCCACC
5161 CCCAATTTTG TATTTATTTA TTTTTAATT ATTTTGTGCA GCGATGGGGG CGGGGGGGGG
5221 GGG
```

Figure 15B2

SEQ ID NO: 15 – Sequence of PBzID-CAG∞RFP (part 1: from nucleotide 1 to nucleotide 3000)

```
   1 CCACATAGCA GAACTTTAAA AGTGCTCATC ATTGGAAAAC GTTCTTCGGG GCGAAAACTC
  61 TCAAGGATCT TACCGCTGTT GAGATCCAGT TCGATGTAAC CCACTCGTGC ACCCAACTGA
 121 TCTTCAGCAT CTTTTACTTT CACCAGCGTT TCTGGGTGAG CAAAAACAGG AAGGCAAAAT
 181 GCCGCAAAAA AGGGAATAAG GGCGACACGG AAATGTTGAA TACTCATACT CTTCCTTTTT
 241 CAATATTATT GAAGCATTTA TCAGGGTTAT TGTCTCATGA GCGGATACAT ATTTGAATGT
 301 ATTTAGAAAA ATAAACAAAT AGGGGTTCCG CGCACATTTC CCCGAAAAGT GCCACCTGAC
 361 GTCCCAATGA TATCATTTAA ATGTCGACAT TGATTATTGA CTAGTTATTA ATAGTAATCA
 421 ATTACGGGGT CATTAGTTCA TAGCCCATAT ATGGAGTTCC GCGTTACATA ACTTACGGTA
 481 AATGGCCCGC CTGGCTGACC GCCCAACGAC CCCCGCCCAT TGACGTCAAT AATGACGTAT
 541 GTTCCCATAG TAACGCCAAT AGGGACTTTC CATTGACGTC AATGGGTGGA CTATTTACGG
 601 TAAACTGCCC ACTTGGCAGT ACATCAAGTG TATCATATGC CAAGTACGCC CCCTATTGAC
 661 GTCAATGACG GTAAATGGCC CGCCTGGCAT TATGCCCAGT ACATGACCTT ATGGGACTTT
 721 CCTACTTGGC AGTACATCTA CGTATTAGTC ATCGCTATTA CCATGGGTCG AGGTGAGCCC
 781 CACGTTCTGC TTCACTCTCC CCATCTCCCC CCCTCCCCA CCCCAATTT TGTATTTATT
 841 TATTTTTTAA TTATTTTGTG CAGCGATGGG GGCGGGGGG GGGGGGCGC GCGCCAGGCG
 901 GGGCGGGGCG GGGCGAGGGG CGGGGCGGGG CGAGGCGGAG AGTGCGGCG GCAGCCAATC
 961 AGAGCGGCGC GCTCCGAAAG TTTCCTTTTA TGGCGAGGCG GCGGCGGCGG CGGCCCTATA
1021 AAAAGCGAAG CGCGCGGCGG GCGGGAGTCG CTGCGTTGCC TTCGCCCCGT GCCCCGCTCC
1081 GCGCCGCCTC GCGCCGCCCG CCCCGGCTCT GACTGACCGC GTTACTCCCA CAGGTGAGCG
1141 GGCGGGACGG CCCTTCTCCT CCGGGCTGTA ATTAGCGCTT GGTTTAATGA CGGCTCGTTT
1201 CTTTTCTGTG GCTGCGTGAA AGCCTTAAAG GGCTCCGGGA GGGCCCTTTG TGCGGGGGGG
1261 AGCGGCTCGG GGGGTGCGTG CGTGTGTGTG TGCGTGGGGA GCGCCGCGTG CGGCCCGCGC
1321 TCCCCGGCGG CTGTGAGCGC TGCGGGCGCG GCGCGGGGCT TTGTCGCCTC CCCGTCTGCC
1381 CGAGGGGAGC GCGGCCGGGG GCGGTGCCCC GCGGTGCGGG GGGCTGCGA GGGGAACAAA
1441 GGCTGCGTGC GGGGTGTGTG CGTGGGGGGG TGAGCAGGGG GTGTGGGCGC GGCGGTCGGG
1501 CTGTAACCCC CCCCTGCACC CCCCTCCCCG AGTTGCTGAG CACGGCCCGG CTTCGGGTGC
1561 GGGGCTCCGT GCGGGGCGTG GCGCGGGGCT CGCCGTGCCG GGCGGGGGGT GGCGGCAGGT
1621 GGGGGTGCCG GCGGGGCGG GGCCGCCTCG GCCGGGGAG GGCTCGGGGG AGGGCGCGG
1681 CGGCCCCGGA GCGCCGGCGG CTGTCGAGGC GCGGCGAGCC GCAGCCATTG CCTTTATGG
1741 TAATCGTGCG ACAGGCCCA GGACTTCCT TTGTCCCAAA TCTGGCCCAG CCCAAATCTC
1801 GGAGGCGCCG CCGCACCCCC TCTAGCGGGC GCGGGCGAAG CGGTGCGGCG CCGGCAGGAA
1861 GGAAATGGGC GGGGAGGGCC TTCGTGCGTC GCCGCGCCGC CGTCCCCTTC TCCATCTCCA
1921 GCCTCGGGGC TGCCGCAGGG GGACGGCTGC CTTCGGGGG GACGGGGCAG GCGGGGTTC
1981 GGCTTCTGGC GTGTGACCGG CGGCTCTAGA GCCTCTGCTA ACCATGTTCA TGCCTTCTTC
2041 TTTTTCCTAC AGCTCCTGGG CAACGTGCTG GTTGTTGTGC TGTCTCATCA TTTTGGCAAA
2101 GCACGTGAGG ACCGGTGCCA CCATGGCCTC CTCCTTAAC CCTAGAAAGA TAGTCTGCGT
2161 AAAATTGACG CATGCATCAA TTGTAACTGC GGTTTAAACT CCCCAGCATG CCTGCTATTG
2221 TCTTCCCAAT CCTCCCCCTT GCTGTCCTGC CCCACCCCAC CCCCCAGAAT AGAATGACAC
2281 CTACTCAGAC AATGCGATGC AATTTCCTCA TTTTATTAGG AAAGGACAGT GAGAGTGGCA
2341 CCTTCCAGGG TCAAGGAAGG CACGGGGGAG GGGCAAACAA CAGATGGCTG GCAACTAGAA
2401 GGCACTAAAG TCGGAGAATT CATTCCCGGG GGAAAAAGAT CTTTAGGCGC CGGTGGAGTG
2461 GCGGCCCTCG GCGCGCTCGT ACTGTTCCAC GATGGTGTAG TCCTCGTTGT GGGAGGTGAT
2521 GTCCAGCTTG ATGTCGGTCT TGTAGGCGCC GGGCAGCTGC ACGGGCTTCT TGGCCATGTA
2581 GGTGGTCTTG ACCTCGGCGT CGTACTGGCC GCCGTCCTTC AGCTTCAGCC TCATCTTGAT
2641 CTCGCCCTTC AGGGCGCCGT CCTCGGGGTA CATCCGCTCG GTGGAGGCCT CCCAGCCCAT
2701 GGTCTTCTTC TGCATTACGG GGCCGTCGGA GGGAAGTTG GTGCCGCGCA GCTTCACCTT
2761 GTAGATGAAC TCGCCGTCCT GCAGGGAGGA GTCCTGGGTC ACGGTCACCA CGCCGCCGTC
2821 CTCGAAGTTC ATCACGCGCT CCCACTTGAA GCCCTCGGGG AAGGACAGCT TCAAGTAGTC
2881 GGGGATGTCG GCGGGGTGCT TCACGTAGGC CTTGGAGCCG TACTGGAACT GAGGGGACAG
2941 GATGTCCCAG GCGAAGGGCA GGGGGCCGCC CTTGGTCACC TTCAGCTTGG CGGTCTGGGT
```

Figure 16B1

SEQ ID NO: 15 – Sequence of PBzID-CAG∞RFP (part 2: from nucleotide 3001 to nucleotide 5201)

```
3001 GCCCTCGTAG GGGCGGCCCT CGCCCTCGCC CTCGATCTCG AACTCGTGGC CGTTCACGGA
3061 GCCCTCCATG CGCACCTTGA AGCGCATGAA CTCCTTGATG ACATTAACCC TAGAAAGATA
3121 ATCATATTGT GACGTACGTT AAAGATAATC ATGCGTAAAA TTGACGCATG TCCGGAGCCG
3181 TAGATATCGG AAAGAAAGCG GCCGCTGCAG GTCGAGGGAT CTTCATAAGA GAAGAGGGAC
3241 AGCTATGACT GGGAGTAGTC AGGAGAGGAG GAAAAATCTG GCTAGTAAAA CATGTAAGGA
3301 AAATTTTAGG GATGTTAAAG AAAAAAATAA CACAAAACAA AATATAAAAA AAATCTAACC
3361 TCAAGTCAAG GCTTTTCTAT GGAATAAGGA ATGGACAGCA GGGGGCTGTT TCATATACTG
3421 ATGACCTCTT TATAGCCACC TTTGTTCATG GCAGCCAGCA TATGGCATAT GTTGCCAAAC
3481 TCTAAACCAA ATACTCATTC TGATGTTTTA AATGATTTGC CCTCCCATAT GTCCTTCCGA
3541 GTGAGAGACA CAAAAAATTC CAACACACTA TTGCAATGAA AATAAATTTC CTTTATTAGC
3601 CACAAGTCAG ATGCTCAACG GCCTTCATGA TGTCCCCATA ATTTTTGGCA GAGGCAAAAA
3661 GATCTCAGTG GTATTTGTGA GCCAGGGCAT TGGCCACACC AGCCACCACC TTCTGATAGG
3721 CAGCCTGCAC CTGAGGAGTG AATTAGAAGC TTTGAGCAAA AGGCCAGCAA AAGGCCAGGA
3781 ACCGTAAAAA GGCCGCGTTG CTGGCGTTTT TCCATAGGCT CCGCCCCCT GACGAGCATC
3841 ACAAAAATCG ACGCTCAAGT CAGAGGTGGC GAAACCCGAC AGGACTATAA AGATACCAGG
3901 CGTTTCCCCC TGGAAGCTCC CTCGTGCGCT CTCCTGTTCC GACCCTGCCG CTTACCGGAT
3961 ACCTGTCCGC CTTTCTCCCT TCGGGAAGCG TGGCGCTTTC TCATAGCTCA CGCTGTAGGT
4021 ATCTCAGTTC GGTGTAGGTC GTTCGCTCCA AGCTGGGCTG TGTGCACGAA CCCCCCGTTC
4081 AGCCCGACCG CTGCGCCTTA TCCGGTAACT ATCGTCTTGA GTCCAACCCG GTAAGACACG
4141 ACTTATCGCC ACTGGCAGCA GCCACTGGTA ACAGGATTAG CAGAGCGAGG TATGTAGGCG
4201 GTGCTACAGA GTTCTTGAAG TGGTGGCCTA ACTACGGCTA CACTAGAAGA ACAGTATTTG
4261 GTATCTGCGC TCTGCTGAAG CCAGTTACCT TCGGAAAAAG AGTTGGTAGC TCTTGATCCG
4321 GCAAACAAAC CACCGCTGGT AGCGGTGGTT TTTTGTTTG CAAGCAGCAG ATTACGCGCA
4381 GAAAAAAAGG ATCTCAAGAA GATCCTTTGA TCTTTTCTAC GGGGTCTGAC GCTCAGTGGA
4441 ACGAAAACTC ACGTTAAGGG ATTTTGGTCA TGAGATTATC AAAAAGGATC TTCACCTAGA
4501 TCCTTTTAAA TTAAAAATGA AGTTTTAAAT CAATCTAAAG TATATATGAG TAAACTTGGT
4561 CTGACAGTTA CCAATGCTTA ATCAGTGAGG CACCTATCTC AGCGATCTGT CTATTTCGTT
4621 CATCCATAGT TGCCTGACTC CCCGTCGTGT AGATAACTAC GATACGGGAG GGCTTACCAT
4681 CTGGCCCCAG TGCTGCAATG ATACCGCGAG ACCCACGCTC ACCGGCTCCA GATTTATCAG
4741 CAATAAACCA GCCAGCCGGA AGGGCCGAGC GCAGAAGTGG TCCTGCAACT TTATCCGCCT
4801 CCATCCAGTC TATTAATTGT TGCCGGGAAG CTAGAGTAAG TAGTTCGCCA GTTAATAGTT
4861 TGCGCAACGT TGTTGCCATT GCTACAGGCA TCGTGGTGTC ACGCTCGTCG TTTGGTATGG
4921 CTTCATTCAG CTCCGGTTCC CAACGATCAA GGCGAGTTAC ATGATCCCCC ATGTTGTGCA
4981 AAAAAGCGGT TAGCTCCTTC GGTCCTCCGA TCGTTGTCAG AAGTAAGTTG GCCGCAGTGT
5041 TATCACTCAT GGTTATGGCA GCACTGCATA ATTCTCTTAC TGTCATGCCA TCCGTAAGAT
5101 GCTTTTCTGT GACTGGTGAG TACTCAACCA AGTCATTCTG AGAATAGTGT ATGCGGCGAC
5161 CGAGTTGCTC TTGCCCGGCG TCAATACGGG ATAATACCGC G
```

Figure 16B2

SEQUENCE LISTING

```
<160> NUMBER OF SEQ ID NOS: 15

<210> SEQ ID NO 1
<211> LENGTH: 42
<212> TYPE: DNA
<213> ORGANISM: artificial
<220> FEATURE:
<223> OTHER INFORMATION: Transposition sequence derived from Inverted
      Terminal Repeat
```

<400> SEQUENCE: 1
ttaaccctag aaagatagtc tgcgtaaaat tgacgcatgc at                    42

<210> SEQ ID NO 2
<211> LENGTH: 39
<212> TYPE: DNA
<213> ORGANISM: artificial
<220> FEATURE:
<223> OTHER INFORMATION: Transposition sequence derived from Inverted
      Terminal Repeat

<400> SEQUENCE: 2
ttaaccctag aaagatagtc tgcgtaaaat tgacgcatg                        39

<210> SEQ ID NO 3
<211> LENGTH: 67
<212> TYPE: DNA
<213> ORGANISM: artificial
<220> FEATURE:
<223> OTHER INFORMATION: Transposition sequence derived from Inverted
      Terminal Repeat

<400> SEQUENCE: 3
ttaaccctag aaagataatc atattgtgac gtacgttaaa gataatcatg cgtaaaattg  60
acgcatg                                                           67

<210> SEQ ID NO 4
<211> LENGTH: 15
<212> TYPE: DNA
<213> ORGANISM: artificial
<220> FEATURE:
<223> OTHER INFORMATION: EGFP

<400> SEQUENCE: 4
atggtgagca agggc                                                  15

<210> SEQ ID NO 5
<211> LENGTH: 15
<212> TYPE: DNA
<213> ORGANISM: artificial
<220> FEATURE:
<223> OTHER INFORMATION: CAGEGFP

<400> SEQUENCE: 5
atggttaata agggc                                                  15

<210> SEQ ID NO 6
<211> LENGTH: 21
<212> TYPE: DNA
<213> ORGANISM: artificial
<220> FEATURE:
<223> OTHER INFORMATION: RFP

<400> SEQUENCE: 6
atggcctcct ccgaggacgt c                                           21

<210> SEQ ID NO 7
<211> LENGTH: 21
<212> TYPE: DNA
<213> ORGANISM: artificial
<220> FEATURE:
<223> OTHER INFORMATION: CAGRFP

<400> SEQUENCE: 7
atggcctcct cccttaatgt c                                           21

```
<210> SEQ ID NO 8
<211> LENGTH: 15
<212> TYPE: DNA
<213> ORGANISM: artificial
<220> FEATURE:
<223> OTHER INFORMATION: IRFP

<400> SEQUENCE: 8
atggcgcgta aggtc                                                    15

<210> SEQ ID NO 9
<211> LENGTH: 15
<212> TYPE: DNA
<213> ORGANISM: artificial
<220> FEATURE:
<223> OTHER INFORMATION: CAGIRFP

<400> SEQUENCE: 9
atggcgttta atgtc                                                    15

<210> SEQ ID NO 10
<211> LENGTH: 21
<212> TYPE: DNA
<213> ORGANISM: artificial
<220> FEATURE:
<223> OTHER INFORMATION: KOZACATG

<400> SEQUENCE: 10
gaacaaatgg ttaataaggg c                                             21

<210> SEQ ID NO 11
<211> LENGTH: 12
<212> TYPE: DNA
<213> ORGANISM: artificial
<220> FEATURE:
<223> OTHER INFORMATION: iCRE

<400> SEQUENCE: 11
atgctgagga ga                                                       12

<210> SEQ ID NO 12
<211> LENGTH: 8
<212> TYPE: DNA
<213> ORGANISM: artificial
<220> FEATURE:
<223> OTHER INFORMATION: CMVCre

<400> SEQUENCE: 12 atgggaga                                                             8

<210> SEQ ID NO 13
<211> LENGTH: 4661
<212> TYPE: DNA
<213> ORGANISM: Artificial Sequence
<220> FEATURE:
<223> OTHER INFORMATION: Sequence of PB-CAG::RFP
<220> FEATURE:
<221> NAME/KEY: misc_feature
<222> LOCATION: (1061)..(1102)
<223> OTHER INFORMATION: piggyBac 5' ITR
<220> FEATURE:
<221> NAME/KEY: misc_feature
<222> LOCATION: (3785)..(3851)
<223> OTHER INFORMATION: piggyBac 3' ITR

<400> SEQUENCE: 13
```

-continued

```
tcaatctaaa gtatatatga gtaaacttgg tctgacagtt accaatgctt aatcagtgag      60
gcacctatct cagcgatctg tctatttcgt tcatccatag ttgcctgact ccccgtcgtg     120
tagataacta cgatacggga gggcttacca tctggcccca gtgctgcaat gataccgcga     180
gacccacgct caccggctcc agatttatca gcaataaacc agccagccgg aagggccgag     240
cgcagaagtg gtcctgcaac tttatccgcc tccatccagt ctattaattg ttgccgggaa     300
gctagagtaa gtagttcgcc agttaatagt ttgcgcaacg ttgttgccat tgctacaggc     360
atcgtggtgt cacgctcgtc gtttggtatg gcttcattca gctccggttc ccaacgatca     420
aggcgagtta catgatcccc catgttgtgc aaaaaagcgg ttagctcctt cggtcctccg     480
atcgttgtca gaagtaagtt ggccgcagtg ttatcactca tggttatggc agcactgcat     540
aattctctta ctgtcatgcc atccgtaaga tgcttttctg tgactggtga gtactcaacc     600
aagtcattct gagaatagtg tatgcggcga ccgagttgct cttgcccggc gtcaatacgg     660
gataataccg cgccacatag cagaacttta aaagtgctca tcattggaaa acgttcttcg     720
gggcgaaaac tctcaaggat cttaccgctg ttgagatcca gttcgatgta acccactcgt     780
gcacccaact gatcttcagc atcttttact ttcaccagcg tttctgggtg agcaaaaaca     840
ggaaggcaaa atgccgcaaa aaagggaata agggcgacac ggaaatgttg aatactcata     900
ctcttccttt ttcaatatta ttgaagcatt tatcagggtt attgtctcat gagcggatac     960
atatttgaat gtatttagaa aaataaacaa ataggggttc cgcgcacatt tccccgaaaa    1020
gtgccacctg acgtcccaat gatatcattt aaatatcgat ttaaccctag aaagatagtc    1080
tgcgtaaaat tgacgcatgc atagcgctat taatgtcgac actagttcag gtcgacattg    1140
attattgact agttattaat agtaatcaat tacggggtca ttagttcata gcccatatat    1200
ggagttccgc gttacataac ttacggtaaa tggcccgcct ggctgaccgc caacgaccc    1260 ccgcccattg acgtcaataa tgacgtatgt tcccatagta acgccaatag ggactttcca    1320
ttgacgtcaa tgggtggact atttacggta aactgcccac ttggcagtac atcaagtgta    1380
tcatatgcca agtacgcccc ctattgacgt caatgacggt aaatggcccg cctggcatta    1440
tgcccagtac atgaccttat gggactttcc tacttggcag tacatctacg tattagtcat    1500
cgctattacc atgggtcgag gtgagcccca cgttctgctt cactctcccc atctccccc    1560 cctccccacc cccaattttg tatttattta ttttttaatt attttgtgca gcgatggggg    1620
cggggggggg ggggcgcgc gccaggcggg gcgggcggg gcgaggggcg gggcggggcg    1680
aggcggagag gtgcggcggc agccaatcag agcggcgcgc tccgaaagtt tccttttatg    1740
gcgaggcggc ggcggcggcg gccctataaa aagcgaagcg cgcggcgggc gggagtcgct    1800
gcgttgcctt cgccccgtgc cccgctccgc gccgcctcgc gccgcccgcc ccggctctga    1860
ctgaccgcgt tactcccaca ggtgagcggg cgggacggcc cttctcctcc gggctgtaat    1920
tagcgcttgg tttaatgacg gctcgtttct tttctgtggc tgcgtgaaag ccttaaaggg    1980
ctccgggagg gccctttgtg cggggggag cggctcgggg ggtgcgtgcg tgtgtgtgtg    2040
cgtggggagc gccgcgtgcg gcccgcgctg cccggcggct gtgagcgctg cgggcgcggc    2100
gcggggcttt gtgcgctccg cgtgtgcgcg agggagcgc ggccggggc ggtgccccgc    2160 ggtgcggggg ggctgcgagg ggaacaaagg ctgcgtgcgg ggtgtgtgcg tggggggtg    2220 agcagggggt gtgggcgcgg cggtcgggct gtaaccccc cctgcacccc cctccccgag    2280
ttgctgagca cggcccggct tcgggtgcgg ggctccgtgc ggggcgtggc gcggggctcg    2340
ccgtgccggg cggggggtgg cggcaggtgg gggtgccggg cggggcgggg ccgcctcggg    2400
```

```
ccggggaggg ctcggggag gggcgcggcg ccccggagc gccggcggct gtcgaggcgc    2460
ggcgagccgc agccattgcc ttttatggta atcgtgcgag agggcgcagg gacttccttt    2520
gtcccaaatc tggcggagcc gaaatctggg aggcgccgcc gcaccccctc tagcgggcgc    2580
gggcgaagcg gtgcggcgcc ggcaggaagg aaatgggcgg ggagggcctt cgtgcgtcgc    2640
cgcgccgccg tccccttctc catctccagc ctcggggctg ccgcagggg acggctgcct    2700 tcgggggga cggggcaggg cggggttcgg cttctggcgt gtgaccggcg gctctagagc    2760
ctctgctaac catgttcatg ccttcttctt tttcctacag ctcctgggca acgtgctggt    2820
tgttgtgctg tctcatcatt ttggcaaaga attcatggcc tcctccgagg acgtcatcaa    2880
ggagttcatg cgcttcaagg tgcgcatgga gggctccgtg aacggccacg agttcgagat    2940
cgagggcgag ggcgagggcc gcccctacga gggcacccag accgccaagc tgaaggtgac    3000
caagggcggc cccctgccct cgcctggga catcctgtcc cctcagttcc agtacggctc    3060
caaggcctac gtgaagcacc ccgccgacat ccccgactac ttgaagctgt ccttccccga    3120
gggcttcaag tgggagcgcg tgatgaactt cgaggacggc ggcgtggtga ccgtgaccca    3180
ggactcctcc ctgcaggacg gcgagttcat ctacaaggtg aagctgcgcg gcaccaactt    3240
cccctccgac ggccccgtaa tgcagaagaa gaccatgggc tgggaggcct ccaccgagcg    3300
gatgtacccc gaggacggcg ccctgaaggg cgagatcaag atgaggctga agctgaagga    3360
cggcggccac tacgacgccg aggtcaagac cacctacatg gccaagaagc ccgtgcagct    3420
gcccggcgcc tacaagaccg acatcaagct ggacatcacc tcccacaacg aggactacac    3480
catcgtggaa cagtacgagc gcgccgaggg ccgccactcc accggcgcct aactgcagat    3540
ctgcggccgc tacgtatcga ctttagtgcc ttctagttgc cagccatctg ttgtttgccc    3600
ctcccccgtg ccttccttga ccctggaagg tgccactctc actgtccttt cctaataaaa    3660
tgaggaaatt gcatcgcatt gtctgagtag gtgtcattct attctggggg gtggggtggg    3720
gcaggacagc aaggggagg attgggaaga caatagcagg catgctgggg gtttaaacct    3780
taagcatgcg tcaattttac gcatgattat ctttaacgta cgtcacaata tgattatctt    3840
tctagggtta aacgcgtatt taaatcgata tcggaaagaa catgtgagca aaaggccagc    3900
aaaaggccag gaaccgtaaa aaggccgcgt tgctggcgtt tttccatagg ctccgcccc    3960 ctgacgagca tcacaaaaat cgacgctcaa gtcagaggtg gcgaaacccg acaggactat    4020
aaagatacca ggcgtttccc cctggaagct ccctcgtgcg ctctcctgtt ccgaccctgc    4080
cgcttaccgg atacctgtcc gcctttctcc cttcggaag cgtggcgctt tctcatagct    4140
cacgctgtag gtatctcagt tcggtgtagg tcgttcgctc caagctgggc tgtgtgcacg    4200
aaccccccgt tcagcccgac cgctgcgcct tatccggtaa ctatcgtctt gagtccaacc    4260
cggtaagaca cgacttatcg ccactggcag cagccactgg taacaggatt agcagagcga    4320
ggtatgtagg cggtgctaca gagttcttga agtggtggcc taactacggc tacactagaa    4380
gaacagtatt tggtatctgc gctctgctga agccagttac cttcggaaaa agagttggta    4440
gctcttgatc cggcaaacaa accaccgctg gtagcggtgg ttttttgtt tgcaagcagc    4500 agattacgcg cagaaaaaaa ggatctcaag aagatccttt gatctttct acggggtctg    4560 acgctcagtg gaacgaaaac tcacgttaag ggattttggt catgagatta tcaaaaagga    4620
tcttcaccta gatcctttta aattaaaaat gaagttttaa a                       4661

<210> SEQ ID NO 14
```

```
<211> LENGTH: 5223
<212> TYPE: DNA
<213> ORGANISM: Artificial Sequence
<220> FEATURE:
<223> OTHER INFORMATION: Sequence of PB-ID
<220> FEATURE:
<221> NAME/KEY: misc_feature
<222> LOCATION: (1228)..(1269)
<223> OTHER INFORMATION: piggyBac 5' ITR
<220> FEATURE:
<221> NAME/KEY: misc_feature
<222> LOCATION: (2241)..(2307)
<223> OTHER INFORMATION: piggyBac 3' ITR

<400> SEQUENCE: 14
```

| | | | | | |
|---|---|---|---|---|---|
| ggcgcgcgcc | aggcggggcg | ggcgggcg | aggggcgggg | cggggcgagg | cggagaggtg | 60 |
| cggcggcagc | caatcagagc | ggcgcgctcc | gaaagtttcc | ttttatggcg | aggcggcggc | 120 |
| ggcggcggcc | ctataaaaag | cgaagcgcgc | ggcgggcggg | agtcgctgcg | ttgccttcgc | 180 |
| cccgtgcccc | gctccgcgcc | gcctcgcgcc | gcccgcccg | gctctgactg | accgcgttac | 240 |
| tcccacaggt | gagcgggcgg | gacggccctt | ctcctccggg | ctgtaattag | cgcttggttt | 300 |
| aatgacggct | cgtttctttt | ctgtggctgc | gtgaaagcct | taaagggctc | cgggagggcc | 360 |
| ctttgtgcgg | gggggagcgg | ctcggggggt | gcgtgcgtgt | gtgtgtgcgt | ggggagcgcc | 420 |
| gcgtgcggcc | cgcgctgccc | ggcggctgtg | agcgctgcgg | gcgcggcgcg | ggctttgtg | 480 |
| cgctccgcgt | gtgcgcgagg | ggagcgcggc | cgggggcggt | gccccgcggt | gcgggggggc | 540 |
| tgcgagggga | acaaaggctg | cgtgcggggt | gtgtgcgtgg | ggggtgagc | aggggtgtg | 600 |
| ggcgcggcgg | tcgggctgta | accccccct | gcaccccct | ccccgagttg | ctgagcacgg | 660 |
| cccggcttcg | ggtgcggggc | tccgtgcggg | gcgtggcgcg | ggctcgccg | tgccgggcgg | 720 |
| ggggtggcgg | caggtggggg | tgccgggcgg | ggcgggggccg | cctcgggccg | gggagggctc | 780 |
| gggggagggg | cgcggcggcc | ccggagcgcc | ggcggctgtc | gaggcgcggc | gagccgcagc | 840 |
| cattgccttt | tatggtaatc | gtgcgagagg | gcgcagggac | ttccttgtc | ccaaatctgg | 900 |
| cggagccgaa | atctgggagg | cgccgccgca | cccctctag | cgggcgcggg | cgaagcggtg | 960 |
| cggcgccggc | aggaaggaaa | tgggcgggga | gggccttcgt | gcgtcgccgc | gccgccgtcc | 1020 |
| ccttctccat | ctccagcctc | ggggctgccg | caggggacg | gctgccttcg | gggggacgg | 1080 |
| ggcagggcgg | ggttcggctt | ctggcgtgtg | accggcggct | ctagagcctc | tgctaaccat | 1140 |
| gttcatgcct | tcttcttttt | cctacagctc | ctgggcaacg | tgctggttgt | tgtgctgtct | 1200 |
| catcattttg | gcaaagaatt | ctcgcgatta | accctagaaa | gatagtctgc | gtaaaattga | 1260 |
| cgcatgcatc | aattgtaact | gcggtttaaa | ctccccagca | tgcctgctat | tgtcttccca | 1320 |
| atcctcccc | ttgctgtcct | gccccacccc | acccccaga | atagaatgac | acctactcag | 1380 |
| acaatgcgat | gcaatttcct | cattttatta | ggaaaggaca | gtgagagtgg | caccttccag | 1440 |
| ggtcaaggaa | ggcacggggg | aggggcaaac | aacagatggc | tggcaactag | aaggcactaa | 1500 |
| agtcggatcc | tcgacaattg | gatatcttag | gcgccggtgg | agtggcggcc | ctcggcgcgc | 1560 |
| tcgtactgtt | ccacgatggt | gtagtcctcg | ttgtgggagg | tgatgtccag | cttgatgtcg | 1620 |
| gtcttgtagg | cgccgggcag | ctgcacgggc | ttcttggcca | tgtaggtggt | cttgacctcg | 1680 |
| gcgtcgtagt | ggccgccgtc | cttcagcttc | agcctcatct | tgatctcgcc | cttcagggcg | 1740 |
| ccgtcctcgg | ggtacatccg | ctcggtggag | gcctcccagc | ccatggtctt | cttctgcatt | 1800 |
| acggggccgt | cggaggggaa | gttggtgccg | cgcagcttca | ccttgtagat | gaactcgccg | 1860 |
| tcctgcaggg | aggagtcctg | ggtcacggtc | accacgccgc | cgtcctcgaa | gttcatcacg | 1920 |

```
cgctcccact tgaagccctc ggggaaggac agcttcaagt agtcgggdat gtcggcgggg    1980
tgcttcacgt aggccttgga gccgtactgg aactgagggg acaggatgtc ccaggcgaag    2040 ggcaggggc cgcccttggt caccttcagc ttggcggtct gggtgccctc gtaggggcgg     2100
ccctcgccct cgccctcgat ctcgaactcg tggccgttca cggagccctc catgcgcacc    2160
ttgaagcgca tgaactcctt gatgacgtcc tcggaggagg ccatggtggc gatatcgcta    2220
ggcccgggct aatcacttaa ttaaccctag aaagataatc atattgtgac gtacgttaaa    2280
gataatcatg cgtaaaattg acgcatgtcc ggagccgtag atatcggaaa gaaagcggcc    2340
gctgcaggtc gagggatctt cataagagaa gagggacagc tatgactggg agtagtcagg    2400
agaggaggaa aaatctggct agtaaaacat gtaaggaaaa ttttagggat gttaaagaaa     2460
aaaataacac aaaacaaaat ataaaaaaaa tctaacctca agtcaaggct tttctatgga    2520
ataaggaatg gacagcaggg ggctgtttca tatactgatg acctctttat agccacctt     2580 gttcatggca gccagcatat ggcatatgtt gccaaactct aaaccaaata ctcattctga    2640
tgttttaaat gatttgccct cccatatgtc cttccgagtg agagacacaa aaaattccaa    2700
cacactattg caatgaaaat aaatttcctt tattagccag aagtcagatg ctcaaggggc    2760
ttcatgatgt ccccataatt tttggcagag ggaaaaagat ctcagtggta tttgtgagcc    2820
agggcattgg ccacaccagc caccaccttc tgataggcag cctgcacctg aggagtgaat    2880
tagaagcttt gagcaaaagg ccagcaaaag gccaggaacc gtaaaaaggc cgcgttgctg    2940 gcgttttttcc ataggctccg cccccctgac gagcatcaca aaaatcgacg ctcaagtcag    3000
aggtggcgaa acccgacagg actataaaga taccaggcgt ttccccctgg aagctccctc    3060
gtgcgctctc ctgttccgac cctgccgctt accggatacc tgtccgcctt tctcccttcg    3120
ggaagcgtgg cgctttctca tagctcacgc tgtaggtatc tcagttcggt gtaggtcgtt    3180
cgctccaagc tgggctgtgt gcacgaaccc ccgttcagc ccgaccgctg cgccttatcc     3240
ggtaactatc gtcttgagtc aacccggta agacacgact tatcgccact ggcagcagcc    3300
actggtaaca ggattagcag agcgaggtat gtaggcggtg ctacagagtt cttgaagtgg    3360
tggcctaact acggctacac tagaagaaca gtatttggta tctgcgctct gctgaagcca    3420
gttaccttcg gaaaaagagt tggtagctct tgatccggca acaaaccac cgctggtagc     3480 ggtggttttt ttgtttgcaa gcagcagatt acgcgcagaa aaaaggatc tcaagaagat    3540 cctttgatct tttctacggg gtctgacgct cagtggaacg aaaactcacg ttaagggatt    3600
ttggtcatga gattatcaaa aaggatcttc acctagatcc ttttaaatta aaatgaagt     3660 tttaaatcaa tctaaagtat atatgagtaa acttggtctg acagttacca atgcttaatc    3720
agtgaggcac ctatctcagc gatctgtcta tttcgttcat ccatagttgc ctgactcccc    3780
gtcgtgtaga taactacgat acgggagggc ttaccatctg gccccagtgc tgcaatgata    3840
ccgcgagacc cacgctcacc ggctccagat ttatcagcaa taaaccagcc agccggaagg    3900
gccgagcgca gaagtggtcc tgcaacttta tccgcctcca tccagtctat taattgttgc    3960
cgggaagcta gagtaagtag ttcgccagtt aatagtttgc gcaacgttgt tgccattgct    4020
acaggcatcg tggtgtcacg ctcgtcgttt ggtatggctt cattcagctc cggttcccaa    4080
cgatcaaggc gagttacatg atccccatg ttgtgcaaaa aagcggttag ctccttcggt      4140
cctccgatcg ttgtcagaag taagttggcc gcagtgttat cactcatggt tatggcagca    4200
ctgcataatt ctcttactgt catgccatcc gtaagatgct tttctgtgac tggtgagtac    4260
```

```
tcaaccaagt cattctgaga atagtgtatg cggcgaccga gttgctcttg cccggcgtca    4320
atacgggata ataccgcgcc acatagcaga actttaaaag tgctcatcat tggaaaacgt    4380 tcttcgggc gaaaactctc aaggatctta ccgctgttga gatccagttc gatgtaaccc     4440
actcgtgcac ccaactgatc ttcagcatct tttactttca ccagcgtttc tgggtgagca    4500
aaaacaggaa ggcaaaatgc cgcaaaaaag ggaataaggg cgacacggaa atgttgaata    4560
ctcatactct ccttttttca atattattga agcatttatc agggttattg tctcatgagc    4620
ggatacatat ttgaatgtat ttagaaaaat aaacaaatag gggttccgcg cacatttccc    4680
cgaaaagtgc cacctgacgt cccaatgata tcatttaaat gtcgacttg attattgact     4740 agttattaat agtaatcaat tacggggtca ttagttcata gcccatatat ggagttccgc    4800
gttacataac ttacggtaaa tggcccgcct ggctgaccgc ccaacgaccc ccgcccattg    4860
acgtcaataa tgacgtatgt tcccatagta acgccaatag ggactttcca ttgacgtcaa    4920
tgggtggact atttacggta aactgcccac ttggcagtac atcaagtgta tcatatgcca    4980
agtacgcccc ctattgacgt caatgacggt aaatggcccg cctggcatta tgcccagtac    5040
atgaccttat gggactttcc tacttggcag tacatctacg tattagtcat cgctattacc    5100
atgggtcgag gtgagcccca cgttctgctt cactctcccc atctccccc cctcccccacc    5160 cccaattttg tatttattta ttttttaatt attttgtgca gcgatggggg cggggggggg    5220
ggg                                                                 5223

<210> SEQ ID NO 15
<211> LENGTH: 5201
<212> TYPE: DNA
<213> ORGANISM: Artificial Sequence
<220> FEATURE:
<223> OTHER INFORMATION: Sequence of PB-zID
<220> FEATURE:
<221> NAME/KEY: misc_feature
<222> LOCATION: (2136)..(2177)
<223> OTHER INFORMATION: piggyBac 5' ITR
<220> FEATURE:
<221> NAME/KEY: misc_feature
<222> LOCATION: (3104)..(3170)
<223> OTHER INFORMATION: piggyBac 3' ITR

<400> SEQUENCE: 15
ccacatagca gaactttaaa agtgctcatc attggaaaac gttcttcggg gcgaaaactc     60
tcaaggatct taccgctgtt gagatccagt tcgatgtaac ccactcgtgc acccaactga    120
tcttcagcat ctttactttt caccagcgtt tctgggtgag caaaaacagg aaggcaaaat    180
gccgcaaaaa agggaataag ggcgacacgg aaatgttgaa tactcatact cttcctttt    240 caatattatt gaagcattta tcagggttat tgtctcatga gcggatacat atttgaatgt    300
atttagaaaa ataaacaaat aggggttccg cgcacatttc cccgaaaagt gccacctgac    360
gtcccaatga tatcatttaa atgtcgacat tgattattga ctagttatta atagtaatca    420
attacggggt cattagttca tagcccatat atggagttcc gcgttacata acttacggta    480
aatggcccgc ctggctgacc gcccaacgac ccccgcccat tgacgtcaat aatgacgtat    540
gttcccatag taacgccaat agggactttc cattgacgtc aatgggtgga ctatttacgg    600
taaactgccc acttggcagt acatcaagtg tatcatatgc caagtacgcc ccctattgac    660
gtcaatgacg gtaaatggcc cgcctggcat tatgcccagt acatgacctt atgggacttt    720
cctacttggc agtacatcta cgtattagtc atcgctatta ccatgggtcg aggtgagccc    780
cacgttctgc ttcactctcc ccatctcccc cccctcccca ccccaatttt gtatttatt    840
```

```
tatttttttaa ttattttgtg cagcgatggg ggcgggggggg ggggggggcgc gcgccaggcg    900
gggcggggcg gggcgagggg cggggcgggg cgaggcggaa aggtgcggcg gcagccaatc    960
agagcggcgc gctccgaaag tttccttttta tggcgaggcg gcggcggcgg cggccctata   1020
aaaagcgaag cgcgcggcgg gcgggagtcg ctgcgttgcc ttcgcccgt gccccgctcc    1080
gcgccgcctc gcgccgcccg ccccggctct gactgaccgc gttactccca caggtgagcg   1140
ggcgggacgg cccttctcct ccgggctgta attagcgctt ggtttaatga cggctcgttt   1200
cttttctgtg gctgcgtgaa agccttaaag ggctccggga gggcccttg tgcgggggggg   1260
agcggctcgg ggggtgcgtg cgtgtgtgtg tgcgtgggga gcgccgcgtg cggcccgcgc   1320
tgcccggcgg ctgtgagcgc tgcgggcgcg gcgcggggct ttgtgcgctc cgcgtgtgcg   1380
cgaggggagc gcggccgggg gcggtgcccc gcggtgcggg ggggctgcga ggggaacaaa   1440
ggctgcgtgc ggggtgtgtg cgtggggggg tgagcagggg gtgtgggcgc ggcggtcggg   1500
ctgtaaccccc ccctgcacc cccctccccg agttgctgag cacggccgg cttcgggtgc    1560
ggggctccgt gcggggcgtg gcgcggggct cgccgtgccg ggcgggggggt ggcggcaggt   1620
gggggtgccg ggcggggcgg ggccgcctcg ggccggggag ggctcggggg aggggcgcgg   1680
cggccccgga gcgccggcgg ctgtcgaggc gcggcgagcc gcagccattg cctttatgg   1740
taatcgtgcg agagggcgca gggacttcct ttgtcccaaa tctggcggag ccgaaatctg   1800
ggaggcgccg ccgcaccccc tctagcgggc gcgggcgaag cggtgcggcg ccggcaggaa   1860
ggaaatgggc ggggagggcc ttcgtgcgtc gccgcgccgc cgtccccttc tccatctcca   1920
gcctcggggc tgccgcaggg ggacggctgc cttcgggggg gacggggcag ggcggggttc   1980
ggcttctggc gtgtgaccgg cggctctaga gcctctgcta accatgttca tgccttcttc   2040
tttttcctac agctcctggg caacgtgctg gttgttgtgc tgtctcatca ttttggcaaa   2100
gcacgtgagg accggtgcca ccatggcctc ctcccttaac cctagaaaga tagtctgcgt   2160
aaaattgacg catgcatcaa ttgtaactgc ggtttaaact ccccagcatg cctgctattg   2220
tcttcccaat cctcccccctt gctgtcctgc cccaccccac ccccagaat agaatgacac   2280
ctactcagac aatgcgatgc aatttcctca ttttattagg aaaggacagt gagagtggca   2340
ccttccaggg tcaaggaagg cacggggag gggcaaacaa cagatggctg caactagaa    2400
ggcactaaag tcgagaatt cattcccggg ggaaaaagat ctttaggcgc cggtggagtg   2460
gcggccctcg gcgcgctcgt actgttccac gatggtgtag tcctcgttgt gggaggtgat   2520
gtccagcttg atgtcggtct tgtaggcgcc gggcagctgc acgggcttct tggccatgta   2580
ggtggtcttg acctcggcgt cgtagtggcc gccgtccttc agcttcagcc tcatcttgat   2640
ctcgcccttc agggcgccgt cctcgggta catccgctcg gtggaggcct cccagcccat   2700
ggtcttcttc tgcattacgg ggccgtcgga ggggaagttg gtgccgcgca gcttcacctt   2760
gtagatgaac tcgccgtcct gcagggagga gtcctgggtc acggtcacca cgccgccgtc   2820
ctcgaagttc atcacgcgct cccacttgaa gccctcgggg aaggacagct tcaagtagtc   2880
ggggatgtcg gcggggtgct tcacgtaggc cttggagccg tactggaact gaggggacag   2940
gatgtcccag gcgaagggca ggggggccgcc cttggtcacc ttcagcttgg cggtctgggt   3000
gccctcgtag gggcggccct cgccctcgcc ctcgatctcg aactcgtggc cgttcacgga   3060
gccctccatg cgcaccttga agcgcatgaa ctccttgatg acattaaccc tagaaagata   3120
atcatattgt gacgtacgtt aaagataatc atgcgtaaaa ttgacgcatg tccggagccg   3180
```

```
tagatatcgg aaagaaagcg gccgctgcag gtcgagggat cttcataaga gaagagggac    3240
agctatgact gggagtagtc aggagaggag gaaaaatctg gctagtaaaa catgtaagga    3300
aaattttagg gatgttaaag aaaaaaataa cacaaaacaa aatataaaaa aaatctaacc    3360
tcaagtcaag gcttttctat ggaataagga atggacagca gggggctgtt tcatatactg    3420
atgacctctt tatagccacc tttgttcatg gcagccagca tatggcatat gttgccaaac    3480
tctaaaccaa atactcattc tgatgtttta aatgatttgc cctcccatat gtccttccga    3540
gtgagagaca caaaaaattc caacacacta ttgcaatgaa aataaatttc ctttattagc    3600
cagaagtcag atgctcaagg ggcttcatga tgtccccata attttggca gagggaaaaa     3660 gatctcagtg gtatttgtga gccagggcat tggccacacc agccaccacc ttctgatagg    3720
cagcctgcac ctgaggagtg aattagaagc tttgagcaaa aggccagcaa aaggccagga    3780
accgtaaaaa ggccgcgttg ctggcgtttt tccataggct ccgcccccct gacgagcatc    3840
acaaaaatcg acgctcaagt cagaggtggc gaaacccgac aggactataa agataccagg    3900
cgtttccccc tggaagctcc ctcgtgcgct ctcctgttcc gaccctgccg cttaccggat    3960
acctgtccgc ctttctccct tcgggaagcg tggcgctttc tcatagctca cgctgtaggt    4020
atctcagttc ggtgtaggtc gttcgctcca agctgggctg tgtgcacgaa ccccccgttc    4080
agcccgaccg ctgcgcctta tccggtaact atcgtcttga gtccaacccg gtaagacacg    4140
acttatcgcc actggcagca gccactggta acaggattag cagagcgagg tatgtaggcg    4200
gtgctacaga gttcttgaag tggtggccta actacggcta cactagaaga acagtatttg    4260
gtatctgcgc tctgctgaag ccagttacct tcggaaaaag agttggtagc tcttgatccg    4320
gcaaacaaac caccgctggt agcggtggtt tttttgtttg caagcagcag attacgcgca    4380
gaaaaaaagg atctcaagaa gatcctttga tcttttctac ggggtctgac gctcagtgga    4440
acgaaaactc acgttaaggg attttggtca tgagattatc aaaaaggatc ttcacctaga    4500
tccttttaaa ttaaaaatga agttttaaat caatctaaag tatatatgag taaacttggt    4560
ctgacagtta ccaatgctta atcagtgagg cacctatctc agcgatctgt ctatttcgtt    4620
catccatagt tgcctgactc cccgtcgtgt agataactac gatacgggag ggcttaccat    4680
ctggccccag tgctgcaatg ataccgcgag acccacgctc accggctcca gatttatcag    4740
caataaacca gccagccgga agggccgagc gcagaagtgg tcctgcaact ttatccgcct    4800
ccatccagtc tattaattgt tgccgggaag ctagagtaag tagttcgcca gttaatagtt    4860
tgcgcaacgt tgttgccatt gctacaggca tcgtggtgtc acgctcgtcg tttggtatgg    4920
cttcattcag ctccggttcc caacgatcaa ggcgagttac atgatccccc atgttgtgca    4980
aaaaagcggt tagctccttc ggtcctccga tcgttgtcag aagtaagttg gccgcagtgt    5040
tatcactcat ggttatggca gcactgcata attctcttac tgtcatgcca tccgtaagat    5100
gcttttctgt gactggtgag tactcaacca agtcattctg agaatagtgt atgcggcgac    5160
cgagttgctc ttgcccggcg tcaatacggg ataataccgc g                       5201
```

MOLECULAR TOOLS AND METHODS FOR TRANSGENE INTEGRATION AND THEIR TRANSPOSITION DEPENDENT EXPRESSION

CROSS-REFERENCES TO RELATED APPLICATIONS

This application claims priority to International Patent Application No. PCT/EP2019/062877 filed on May 17, 2019, which claims the benefit of European Patent Application No. 18305623.3 filed on May 18, 2018.

STATEMENT REGARDING SEQUENCE LISTING

The sequence listing associated with this application is provided in text format and is hereby incorporated by reference into the specification. The name of the text file containing the sequence listing is eolf-othd-000002.txt. The text file is 22.7 KB; was created on May 17, 2019; and was submitted electronically via European Patent Office with the filing of International Patent Application No. PCT/EP2019/062877 filed on May 17, 2019.

FIELD OF THE DISCLOSURE

Embodiments of the present disclosure relate to biology and the technical field of genetic engineering and in particular DNA modifications in isolated cells or in living organisms. The disclosure is directed at providing molecular tools and methods for transgenes integration in the genome of host cells, in particular tools and method enabling a transposition-dependent expression of the transgene, thereby facilitating detection and selection of effectively transformed hosts. The disclosure is also directed at the production and use of recombinant hosts transformed with the molecular tools and/or method of the disclosure. The disclosure is further directed to the biotechnological and therapeutic uses of the molecular tools or recombinant hosts according to the disclosure.

BACKGROUND OF THE DISCLOSURE

Achieving appropriate integration and expression of transgenes is a basic requirement in genetic engineering. Lentiviral and retroviral vectors have long been used for this purpose, but they are intrinsically limited in their cargo capacity and prone to silencing, their preparation is long, labor intensive and expensive, their storage and shipment requires specific conditions and their usage is subject to tight regulations. Naked plasmid DNA vectors and DNA-based viral vectors such as adeno-associated vectors (AAVs) are much more convenient to produce and handle. They are increasingly used to achieve transgene expression in genomic configuration, thanks to technologies that enhance random or locus-specific integration, in particular transposons that are active in vertebrate species such as piggyBac, Tol2 or Sleeping Beauty (Wu et al., 2006), and site-specific endonucleases including in particular Zinc-finger nucleases (ZFNs), transcription activator-like effector nucleases (TAL-ENs) and CRISPR/Cas9 (Gaj et al., 2013). However, a general problem with DNA vectors is the identification of recombinant cells, usually achieved by expressing specific markers from the vector (e.g. drug resistance or fluorescent protein markers). With classic vector configurations where a gene or interest (GOI) is placed under the control of a promoter, establishing and analyzing recombinant cells bearing genome-integrated transgenes is hindered by marker expression from the episomal form of the vector prior to transgene integration. This typically causes a transient burst of expression after transfection that masks that from integrated transgenes, with two detrimental consequences. First, expression from genomic transgenes cannot be reliably assessed prior elimination of episomes, which typically requires multiple rounds of cell division and results in weeks-long delays (10-20 days or more) to select and analyze transgenic cells. Second, episomal expression at abnormally high levels may perturb metabolism and gene expression, with potential harmful effects on the behavior, identity and viability of target cells. Inducible expression strategies may be used to delay transgene expression and avoid the transient expression burst from episomes, but they necessitate additional manipulations of the cells, often suffer from leakiness and are still subordinate to episome elimination by cell division to assay genome-integrated transgenes, introducing week-long delays in transgenesis procedures.

There is thus a need for improved molecular tools and methods useful for transgenesis, and which would overcome the above-mentioned drawbacks, in particular prevent or limit episomal expression of the vectors carrying the transgene.

DESCRIPTION

The inventors have developed molecular tools, and in particular vectors, useful for the integration of a gene of interest (GOI) in a genome, enabling to couple integration and expression of the gene, under the control of a promoter of choice. In other terms, when the vector is in an episomal form, the configuration of the vector is not compatible with the expression of the GOI, which is therefore silenced, thereby limiting or preventing expression from such episomal form. The configuration of the vectors of the disclosure is such that the integration of the GOI in the genome by transposition induces configurational changes within the sequence of the vector, these changes resulting in an integrated sequence compatible with expression of the GOI. This system can be referred to as transposition-dependent switch, the expression of the GOI being only possible once the GOI has been subjected to transposition.

The vectors of the disclosure utilize various molecular elements already known in the art, in particular a promoter sequence, a sequence encoding a gene of interest, and a set of two sequences derived from, preferably comprising or consisting of 5' and 3' ITR from DNA transposons, and which are capable of inducing the integration of a polynucleotide sequence of interest in a genome, these elements being arranged within the vector in such a way so as to prevent the expression of the transgene of interest prior to its integration in the genome.

The vectors of the disclosure rely in particular on the use of a set of sequences derived from, preferably comprising or consisting of 5' and 3' ITR from DNA transposons.

DNA transposons, also referred to as class II transposable elements (TE), are typically formed of a DNA molecule comprising a central sequence which encodes a transposase protein, flanked by inverted terminal repeats (ITR) sequences. These transposons include the piggyBac, Tol2 and Sleeping Beauty TEs active in vertebrate cells. DNA transposons are generally removed from their locus and integrated in a foreign genome or sequence by a cut-and-paste mechanism. The cut-and-paste mechanism begins with the binding of two transposase monomers to the ITR sequences. Then, the transposon ends are brought together by both transposase monomers so as to form a dimer. When the dimer is formed, excision of the transposon DNA body takes places, generating a transient structure called the paired-end complex. At the excision site, continuity of the donor DNA molecule from which the transposon has been removed may be restored by the host cell DNA repair machinery. Finally, the transposase dimer of the paired-end complex binds to a DNA integration site where the DNA is cut, and the integration takes place. Upon insertion, the DNA integration site is duplicated, generating what is called a transposon footprint, which will ultimately flank the integrated transposon. Both the sequence of the ITR sequences and their orientation relative to each other are critical for these molecular events to take place, and result in transposon integration.

Sets of inverted terminal repeats (ITR) derived from, preferably comprising or consisting of, transposons are well known in the art, and have been used as molecular tools for transgenesis. These sequences function as a set, in that they can only enable the introduction of a sequence of interest in a genome when they are both present in the nucleotide molecule comprising the sequence to be inserted, based on the molecular mechanisms detailed above.

Typically, their position and orientation define the sequence which will actually be integrated in the genome, usually called the transgene sequence, which corresponds to the sequence of the vector which is flanked by a set of ITR operatively arranged, that is to say wherein the 5' ITR and the 3' ITR are positioned and oriented so as to enable the integration of the gene of interest in the genome. Usually, in the art, an integration cassette is formed, when read from the 5' end to the 3' end in the sense orientation (with respect to the open reading frame of the gene of interest) of the following:

5'-ITR1-promoter-gene of interest-ITR2-3',

In this scheme, the 5' ITR (ITR1) and the 3' ITR (ITR2) are positioned and oriented such that they frame the transgene of interest and drive its integration in the genome of host cells, while the rest of the vector does not integrate. The orientation of 5' ITR and 3' ITR in this classical scheme will hereafter be defined as "sense" orientation. Should the ITR1 and ITR2 sequences be oriented in the antisense direction, with respect to the above arrangement, the transgene sequence would then correspond to the part of the vector that does not contain the gene of interest under the control of the promoter. In this case, the gene of interest and the promoter would not integrate the genome. It is therefore possible to identify a sense and an anti-sense orientation for ITR sequences, and thereby determine how they are arranged, with respect to the open reading frame of the sequence of a gene of interest.

In the vectors of the disclosure, silencing of the transgene is obtained by arranging the sequence of the promoter and the sequence of the gene of interest within the vector such that the sequence of the promoter is in the sense orientation, while at least part of the sequence of the gene of interest is in the anti-sense orientation, the sequence of the promoter and the part of the sequence of the gene of interest being furthermore separated by one of the ITR sequences derived from, preferably comprising or consisting of a DNA transposon. Therefore, prior to its integration in the genome, that is to say within the vector in an episomal form, the gene of interest is not under the control of the promoter.

In addition to the above, in the vector of the disclosure, the set of ITR sequences are oriented opposite to each other, that is to say that one is in the sense orientation while the other is in the anti-sense orientation, with respect to the orientation of the promoter.

Interestingly, this particular position and orientation of the set of integration sequences, although counter intuitive, results in the integration of the gene of interest under the control of the promoter of choice (i.e. comprised in the vector of the disclosure) in the genome of host cells.

Without being bound by theory, it is proposed that the vectors of the disclosure, upon transfection in a host cell, together with transposase enzyme appropriate for their integration in the genome of the host cell, are subject to conformational changes leading to the rearrangement of the various elements constitutive of the vector, causing a flipping of the promoter region relative to the gene of interest and bringing next to each other the promoter and the gene of interest, which then ends under the control of the promoter.

Despite the counter-intuitive arrangement of their elements, the vectors of the disclosure enable integration and expression of the gene of interest. Because this expression is transposition-dependent, the vectors and methods of the disclosure prevent the transient burst of expression (from episomal vectors) that occurs with classic plasmid-based vectors prior to their dilution by cell division. Instead, with the vectors and methods of the disclosure, sustained expression is obtained from genome-integrated transgene copies while episomes are kept silent, thereby limiting toxic effects or other unwanted biological consequences, and allowing to readily and efficiently detect the host cells in which the sequence of the gene of interest has actually been integrated in the genome.

When transfected in a host cell using the methods of the disclosure, the vectors of the disclosure enable the integration of the gene of interest under the control of the promoter of choice, which may be of particular interest when an inducible promoter (e.g. induced in specific cell types, stages, phases of the cell cycle or upon application of certain drugs) is required.

A first object of the disclosure is a recombinant vector which comprises:
   a) a promoter;
   b) a gene of interest (GOI);
   c) a set of two sequences consisting in a first sequence and a second sequence being respectively derived from, preferably comprising or consisting of a 5' ITR and a 3' ITR of a DNA transposon, wherein the first sequence and the second sequence are in opposite orientation relative to each other;
wherein one of the two sequences of the set is located between the promoter and at least part of the gene of interest (GOI), and wherein the at least part of the sequence of the gene of interest is in an anti-sense orientation with respect to the orientation of the promoter.

One of the two sequences of the set is located between the promoter and at least part of the GOI. Preferably, the at least part of the GOI is flanked by one of the two sequences of the set which is located between the promoter and at least part of the GOI and by the other one of the two sequences of the set. It should therefore be understood that the sense of orientation of the elements of the vector can be defined with respect to the sense of the sequence of the promoter.

It is well known in molecular biology that promoter sequences define the direction of transcription, and thereby indicate which DNA strand will be transcribed, the strand being then referred to as the "sense strand". In the context of the disclosure, in a nucleic acid molecule, which sequence is read from the 5' end to the 3' end, the sense orientation of the sequence of a promoter is the orientation which enables the transcription of elements localized downstream of the sequence, that is to say on 3' of the promoter. Since the promoters appropriate for the vector of the disclosure are well known and routinely used in molecular biology, the person skilled in the art can easily determine their sense and anti-sense direction, and appropriately design the other elements of the vector in consequence.

In the context of the disclosure, the sequence of a nucleic acid is the succession of nucleotide residues that constitute the molecule, presented from the 5' end to the 3' end, using the IUPAC convention, wherein the adenine residue is represented by the letter A, the cytosine residue is represented by the letter C, the guanine residue is represented by the letter G and the thymine residue is represented by the letter T. When the nucleic acid molecule is a double strand molecule, such as DNA, unless otherwise specified, the sequence of the molecule is that of the sense strand. By "sequence of a promoter" it is herein referred to a nucleic acid sequence which is recognized by a host cell for expression of a specific nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell. A nucleic acid sequence is under control of a promoter if the promoter exercises its function on the nucleic acid.

Promoters and their sequences are well known in the art, and include for instance constitutive promoter and inducible promoter.

Constitutive promoters appropriate for the vector of the disclosure include, but are not limited to, immediate early cytomegalovirus (CMV) promoter, herpes simplex virus 1 (HSV1) immediate early promoter, SV40 promoter, lysozyme promoter, early and late CMV promoters, early and late HSV promoters, actin promoter, synthetic CAG promoter (composed of CMV immediate-early enhancer, the first exon and the first intron of the chicken beta-actin gene and the splice acceptor of the rabbit beta-globin gene), elongation factor-1 alpha (EF-1 alpha) promoter, tubulin promoter, Rous-Sarcoma virus (RSV) promoter, and heat-shock protein (HSP) promoter. Other examples of constitutive promoters appropriate for the vector of the disclosure include but are not limited to smooth-muscle SM22 promoter, including chimeric SM22alpha/telokin promoters, ubiquitin C promoter, Hsf2 promoter; murine COMP (cartilage oligomeric matrix protein) promoter; early B cell-specific mb-1 promoter; prostate specific antigen (PSA) promoter; pineal expression-promoting element promoter; neural and liver ceramidase gene promoters; PSP94 gene promoter; the promoter of the human FAT/CD36 gene; VL30 promoter; and, IL-10 promoter.

Inducible promoters appropriate for the vector of the disclosure include, but are not limited to, tissue-specific promoters, developmentally-regulated promoters and chemically inducible promoters. Examples of tissue-specific promoters include the vitellogenin promoter, ovalbumin promoter, ovomucoid promoter, conalbumin promoter, ovotransferrin promoter, prolactin promoter, kidney uromodulin promoter, and placental lactogen promoter. Examples of developmentally-regulated promoters include the homeobox promoters and several hormone induced promoters. Examples of chemically inducible promoters include reproductive hormone induced promoters and antibiotic inducible promoters such as the tetracycline inducible promoter and the zinc-inducible metallothionine promoter. Other inducible promoter systems appropriate for the vector of the disclosure include the Lac operator repressor system inducible by IPTG (isopropyl beta-D-thiogalactoside), ecdysone-based inducible systems, estrogen-based inducible systems, progesterone-based inducible systems.

In order to improve the function of the promoter, and thereby increase and stabilize the expression of the gene of interest when integrated in the genome, the vector of the disclosure preferably further comprises a promoter enhancer and/or epigenetic regulators. These elements, when present in the vector of the disclosure, are preferably oriented in the same orientation as the promoter sequence. Promoter enhancers are well known in the art and include for instance HACNS1, GADD45G and CMV immediate early enhancer. Epigenetic regulators are well known in the art and include boundary or insulator elements, locus control regions (LCRs), stabilizing and antirepressor (STAR) elements, ubiquitously acting chromatin opening (UCOE) elements and matrix attachment regions (MARs). All of these epigenetic regulators have been used for recombinant protein production in mammalian cell lines (Zahn-Zabal et al., 2001) and for gene therapies.

By "sequence encoding a gene of interest (GOI)" it is herein referred to a nucleotide sequence encoding a peptide of interest, presented from the 5' end to the 3' end, and read in the sense orientation corresponding to its open reading frame, which comprises the structural elements necessary for its translation, that is to say for the production of the peptide it encodes. In the context of the disclosure, the gene of interest can be any polynucleotide encoding a peptide of interest, which expression is desired, and thus which sequence can be transcribed and translated. Preferably, a sequence of a gene of interest (GOI) comprises 3 consecutive nucleotides encoding a start codon its 5' terminal part. In the context of the disclosure, a start codon is the first codon of a messenger RNA transcript translated by a ribosome. Start codons include AUG, which is the most common start codon in eukaryotes; as well as alternative start codons such as AUA, AUU, GUG, UUG. Most preferably, the sequence of a gene of interest comprises, in its 5' terminal part, the 3 consecutive nucleotides ATG.

The sequence of the gene of interest may further comprise a protein degradation signal. In the context of the disclosure, the terms "protein degradation signal", also referred to as degron, should be construed as generally understood in the field of molecular biology, that is to say as referring to a nucleic sequence comprised within the sequence of protein, and which decrease the half-life of the protein. Protein destruction signals have been identified, which corresponding nucleic sequence may be introduced in N-terminal of the protein, to engineer fast-degradable recombinant proteins. Protein degradation signals appropriate in the context of the disclosure include, but are not limited to, PEST sequences and cyclin destruction boxes.

The sequence of the gene of interest preferably further comprises a sequence encoding a protein tag. Sequences encoding protein tags appropriate in the context of the disclosure include, but are not limited to, the genes encoding the FLAG, HBH, MBP, CBP, V5, hemaglutinin antigen (HA), c-myc and polyhistidine (His) tag, useful for the detection and purification of the protein they are fused with.

Preferably, in the vector of the disclosure, the gene of interest is operatively linked to a polyadenylation signal and/or a transcription terminator.

In the context of the disclosure, a gene of interest is "operably linked" to a polyadenylation signal when the sequence of the gene of interest and that of the polyadenylation signal are positioned and oriented in such a way as to enable the addition of a poly(A) tail to the messenger RNA produced by transcription of the gene of interest. In the context of the disclosure, a gene of interest is "operably linked" to a transcription terminator when the sequence of the gene of interest and that of the transcription terminator are positioned and oriented in such a way as to enable the endonucleolytic cleavage and addition of a poly(A) tail to the messenger RNA produced by transcription of the gene of interest.

In the context of the disclosure, the terms "polyadenylation signal" should be construed as generally understood in molecular biology, that is to say as referring to a nucleotide sequence that mediates the post-transcriptional addition of multiple adenine (A) nucleotides to the tail of a messenger RNA transcript. Polyadenylation signals are usually localized downstream of the sequence of the gene to be transcribed, after the stop codon. In the context of the disclosure, they are oriented in the sense orientation with respect to the open reading frame of the sequence of the gene of interest. In embodiments wherein the vector of the disclosure comprises more than one gene of interest, as detailed above, the polyadenylation signal is preferably localized downstream of the last stop codon in the 3' terminal part of the sequence of the gene of interest.

In the context of the disclosure, the terms "transcription terminator" should be construed as generally understood in molecular biology, that is to say as referring to a nucleotide sequence that mediates transcriptional termination of a gene of interest, and thus marks the end of its transcription into RNA. Transcription terminator are usually localized downstream of the sequence of the gene to be transcribed, and typically directly after any 3' regulatory elements, such as the polyadenylation signal.

Transcription terminators and polyadenylation signals appropriate in the context of the disclosure include the SV40, human growth hormone (hGH), bovine growth hormone (bGH), and rabbi beta-globin (rbGlob) polyadenylation signals. These signals include a sequence motif (AAUAAA) which promotes both polyadenylation and termination.

In the vector of the disclosure, at least part of the sequence of the gene of interest is in an anti-sense orientation with respect to the sequence of the promoter. In other terms, at least part of the gene of interest is present in the form of the complementary sequence of the corresponding portion of the gene of interest.

The term "complementary" or "complement", when referring to a nucleotide sequence, such as a DNA or RNA sequence, should be construed as generally understood in the art. A nucleotide sequence will thus be considered as complimentary to a nucleotide sequence of reference, when the two nucleotide sequences form a hybridized duplex by base pairing. The degree of complementarity between a nucleotide sequence and a nucleotide sequence of reference may vary, from complete complementarity (each nucleotide is across from its opposite) to partial complementary (50%, 60%, 70%, 80%, 90% or 95%). A nucleotide sequence is considered as completely complementary to a nucleotide sequence of reference if all of the nucleotides in the sequence form base pairing with the nucleotides in the corresponding antiparallel positions of the sequence of reference. The terms base pairing refer to the pairing of nucleotide base A with T, and of nucleotide C with G.

Preferably, in the context of the disclosure, a sequence complementary to a sequence of reference is completely complementary to the sequence of reference.

It should be understood that the sequence of the gene of interest may be present in the recombinant vector of the disclosure either in the form of one nucleotide segment, or in the form of several fragments of the sequence of the gene of interest, which are arranged in a non-continuous manner, provided that at least one of the fragments is in an anti-sense orientation with respect to the sequence of the promoter, and is separated from the sequence of the promoter by one of the two sequences of the set as herein defined.

Thus, according to the disclosure, when the sequence of the gene of interest is present in the form of one nucleotide segment, the entire sequence of the gene of interest is in an anti-sense orientation with respect to the sequence of the promoter, and the sequence of the gene of interest and that of the promoter are separated by one of the two sequences of the set as herein defined. In this embodiment, in the vector of the disclosure, the gene of interest is initially not under the control of the promoter, or, in other terms, the promoter is not operably linked to the gene of interest.

Alternatively, when the sequence of the gene of interest is present in the recombinant vector of the disclosure in the form of several fragments, preferably two fragments consisting in the 5' terminal part of the sequence of the gene of interest and the 3'terminal part of the sequence of the gene of interest, preferably at least the 3' terminal part of the sequence of the gene of interest is in an anti-sense orientation with respect to the sequence of the promoter and is separated from the sequence of the promoter by one of the two sequences of the set as herein defined.

In a preferred embodiment, in the vector of the disclosure, the gene of interest is present in the form of two fragments consisting in the 5' terminal part of the sequence of the gene of interest and the 3'terminal part of the sequence of the gene of interest, wherein:

the 3' terminal part of the sequence of the gene of interest is in an anti-sense orientation with respect to the sequence of the promoter, and the 3' terminal part of the sequence of the gene of interest and the sequence of the promoter are separated by one of the two sequences of the set as herein defined; and the 5' terminal part of the sequence of the gene of interest is localized downstream of the promoter sequence, preferably is not separated from the promoter by any of the two sequences of the set as herein defined, and is in the sense orientation with respect to the sequence of the promoter.

The above embodiment is particularly advantageous in that the gene of interest being present in the form of two fragments which are not contiguous, and further are in an anti-sense orientation with respect to each other, the product of the gene of interest cannot be expressed, further reinforcing the silencing effect on episomal forms of the vector even in the event of cryptic initiation of transcription of the gene of interest prior to transposition. Nevertheless, during the molecular events induced during transgenesis, the different elements of the vector are rearranged in such a way as to reposition the 5' and the 3' terminal parts of the sequence of the gene of interest in a contiguous manner, in the same orientation and further under the control of the promoter, thereby restoring the sequence in its entirety, such that the gene of interest can be fully transcribed and translated.

The vector of the disclosure may further comprise, in addition to the gene of interest, one or more additional distinct genes of interest, which are intended to be integrated together with the sequence of the gene of interest in the new genome. The position and orientation of the sequence of the one or more additional distinct genes of interest may be adapted according to the expected use of the recombinant vector of the disclosure, and in particular the expected pattern of expression of the one or more additional distinct genes of interest. For instance, when an expression in the episomal form of the one or more additional distinct genes of interest is desired, the sequence of the one or more additional distinct genes of interest may be positioned and oriented so as to be under the control of the promoter in the vector. Conversely, when an transposition-dependent expression of the one or more additional distinct genes of interest is desired, the orientation of their sequence may mimic that of the principal gene of interest mentioned above, in that it is in the anti-sense orientation with respect to the sequence of the promoter, and the sequence and that of the promoter are separated by one of the two sequences of the set as herein defined.

In an embodiment of the disclosure, wherein the vector of the disclosure comprises, in addition to the gene of interest, one or more additional distinct genes of interest, the sequence of the one or more additional distinct genes of interest is under the control of the promoter, preferably is localized downstream of the promoter sequence, preferably is not separated from the promoter by any of the two sequences of the set as herein defined.

In another embodiment of the disclosure, wherein the vector of the disclosure comprises, in addition to the gene of interest, one or more additional distinct genes of interest, the sequence of the one or more additional distinct genes of interest is in the anti-sense orientation with respect to the sequence of the promoter, and the sequence of the one or more additional distinct genes of interest and that of the promoter are separated by one of the two sequences of the set as herein defined. Preferably, in this embodiment, in order to enable transposition-dependent expression of all of the genes of interest integrated in the recombinant vector of the disclosure, their respective sequences may be operatively linked for the purpose of transcription and translation. This feature can easily be achieved by organizing the sequences of the genes as a single functioning unit for the purpose of transcription, by fusing the genes, thereby obtaining a fusion protein, and possibly by inserting between the respective gene sequences an internal ribosome entry site IRES) or 2A element. In these embodiments wherein the gene of interest is present in the vector in the form of two fragments, consisting in the 5' terminal part of the sequence of the gene of interest and the 3' terminal part of the sequence of the gene of interest, the sequence of the one or more additional distinct genes of interest is contiguous to the 3' terminal part of the sequence of the gene of interest, oriented in the same direction as the 3' terminal part of the sequence of the gene of interest, positioned downstream of the 3' terminal part of the sequence of the gene of interest with respect to the open reading frame of the 3' terminal part of the sequence of the gene of interest, and the 3' terminal part of the sequence of the gene of interest and the sequence of the one or more additional distinct genes of interest are separated by an internal ribosome entry site (IRES) element or a 2A element.

Both IRES and 2A elements are well known in the art, and are routinely used in molecular biology, in particular in vector and other nucleic acid constructs. 2A elements appropriate in the context of the disclosure are for instance the T2A, P2A, E2A and F2A elements, that is to say the nucleotide sequences encoding the T2A, P2A, E2A and F2A peptides.

Preferably, at least one of the additional distinct genes of interest is chosen from the list consisting of reporter genes and genes encoding a selection marker.

In the context of the disclosure, the terms "reporter gene" should be construed as generally understood in the field of molecular biology, that is to say as referring to a gene encoding a peptide product which can easily be detected using techniques or methods known in the art. Reporter genes appropriate in the context of the disclosure include, but are not limited to, any of fluorescent protein (e.g., green (GFP), red, near-infrared, yellow, cyan or blue fluorescent protein, enhanced green, red, yellow, cyan or blue fluorescent protein), beta--lactamase, beta-galactosidase, luciferase (e.g., firefly luciferase (FLuc), Renilla (RLuc) luciferase, NANOLUC luciferase (NlucP) (Promega, Madison, WI), bacterial luciferase, Click-Beetle Luciferase Red (CBRluc), Click-Beetle Luciferase Green (CBG681uc and CBG991uc), *Metridia pacifica* Luciferase (MetLuc), *Gaussia* Luciferase (GLuc), Cypridina Luciferase, and *Gaussia*-Dura Luciferase), chloramphenicol acetyltransferase (CAT), neomycin phosphotransferase, alkaline phosphatase, secreted alkaline phosphatase (SEAP), Chloramphenicol acetyltransferase (CAT), mCherry, tdTomato, TurboGFP, TurboRFP, dsRed, dsRed2, dsRed Express, AcGFPl, ZsGreenl, Red Firefly Luciferase, Enhanced Click-Beetle Luciferase (ELuc), Dinoflagellate Luciferase, Pyrophorus plagiophthalamus, Luciferase (lucGR), Bacterial luciferase (Lux), pmeLUC, *Phrixothrix hirtus* Luciferase, *Gaussia*-Dura Luciferase, RenSP, *Vargula hilgendorfn* Luciferase, Lucia Luciferase, *Metridia longa* Luciferase (MetLuc), HaloTag, SNAP-tag, CLIP-tag, β-Glucuronidase, Aequorin, Secreted placental alkaline phosphatase (SPAP), Gemini, TagBFP, mTagBFP2, Azurite, EBFP2, mKalamal, Sirius, Sapphire, T-Sapphire, ECFP, Cerulean, SCFP3A, mTurquoise, mTurquoise2, Midoriishi-Cyan, TagCFP, mTFPl, Emerald, Superfolder GFP, Azami Green, TagGFP2, mU G, mWasabi, Clover, Citrine, Venus, SYFP2, TagYFP, Kusabira-Orange, mKO, mK02, mOrange, mOrange2, mRaspberry, mStrawberry, mTangerine, TagRFP, TagRFP-T, mApple, mRuby, mRuby2, mPlum, HcRed-Tandem, mKate2, mNeptune, NirFP, TagRFP657, IFP1.4, iRFP, meima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, PSmOrange, Dronpa, TurboYFP, TurboFP602, TurboFP635, TurboFP650, hrGFP, hrGFP II, E2-Crimson, HcRed1, Dendra2, AmCyan1, ZsYellow1, mBanana, EBFP, Topaz, mECFP, CyPet, yPet, PhiYFP, DsRed-Monomer, Kusabira Orange, Kusabira Orange2, Jred, AsRed2, dKeima-Tandem, AQ143, mKikGR, and homologs and variants thereof.

The vector of the disclosure preferably comprises a gene encoding a selection marker. In the context of the disclosure, the terms "gene encoding a selection marker" should be construed as generally understood in the field of molecular biology, that is to say as referring to a gene encoding a peptide product which confers resistance to a selection agent, preferably an antibiotic. Genes encoding a selection marker appropriate in the context of the disclosure include, but are not limited to, chloramphenicol, ampicillin, gentamycin, streptomycin, tetracyclin, kanamycin, neomycin, puromycin, histidinol, hygromycin resistance genes.

The vector of the disclosure preferably further comprises at least a multiple cloning site. In the context of the disclosure, the terms "multiple cloning site", or "multiple restriction enzyme cleavage sites" refer to a nucleotide sequence comprising more than one restriction enzyme site. Multiple cloning sites are well known and are routinely used in molecular biology to allow the direct cloning of a variety of restriction fragments.

The vector of the disclosure as herein defined comprises a set of two sequences consisting in a first sequence and a second sequence being respectively derived from, preferably comprising or consisting of a 5' ITR and a 3' ITR of a DNA transposon.

The terms "DNA transposon" should be construed as generally understood in molecular biology, that is to say as Class II transposable elements (TE) that are capable of transposing between two DNA molecules or sequence environment. Eukaryotic DNA transposons can be divided into three major subclasses: (i) those that excise as double-stranded DNA and reinsert elsewhere in the genome, also referred to as "cut-and-paste" transposons; (ii) those that utilize a mechanism probably related to rolling-circle replication, Helitrons; and (iii) Mavericks, whose mechanism of transposition is not yet well understood, but that likely replicate using a self-encoded DNA polymerase.

Cut and paste DNA transposons, also referred to as class II cut-and-paste TE, are typically formed of a DNA molecule comprising a central sequence which encodes a transposase protein, flanked by inverted terminal repeats (ITR) sequences. When referring to transposons, the term "inverted terminal repeats" refers to the set of two sequences flanking the transposase gene, and which are capable of complementary base pairing (regions which can base pair with each other). In other terms, inverted terminal repeats of a transposon form a set of a first and a second sequences, the first sequence being localized in 5' (upstream) of the transposase gene, the second sequence being localized in 3' (downstream) of the transposase gene, the first and second sequences being capable of complementary base pairing.

Thus, the sequence of a cut and paste DNA transposon, read from the 5' end to the 3' end, wherein the sense orientation is defined by the open reading frame of the gene encoding the transposase, and ITR are operatively arranged, that is to say, positioned and oriented so as to enable the integration of the transposase gene in another sequence or genome, is typically formed of:

5'-ITR1-transposase gene-ITR2-3', wherein the sequences of ITR1 and ITR2 are capable of complementary base pairing. It is therefore possible to define, for all known cut-and-paste DNA transposons, the sequence and sense of orientation of the ITR localized in either 5' or 3' of the transposon.

Thus, in the context of the disclosure, the terms "5' ITR", when referring to a cut and paste DNA transposon, will be used to refer to the sequence of the ITR localized upstream of the transposase gene wherein the sense orientation is defined by the open reading frame of the gene encoding the transposase, and ITRs are operatively arranged as defined above. The terms "3' ITR", when referring to a cut and paste DNA transposon, will be used to refer to the sequence of the ITR localized downstream of the transposase gene wherein the sense orientation is defined by the open reading frame of the gene encoding the transposase, and ITR are operatively arranged as defined above.

As herein defined, the vector of the disclosure comprises a set of two sequences consisting in a first sequence and a second sequence being respectively derived from, preferably comprising or consisting of a 5' ITR and a 3' ITR of a DNA transposon, wherein the first sequence and the second sequence are in opposite orientation relative to each other. In the context of the disclosure, these terms should be construed as indicating that either the sequence derived from, preferably comprising or consisting of a 5' ITR or the sequence derived from, preferably comprising or consisting of the 3' ITR of the DNA transposon of reference, is in an opposite orientation relative to the classic arrangement found in the transposon from which it is derived. Considering that in the DNA transposon of reference, the 5' ITR and the 3'ITR are both in the sense orientation, wherein the sense orientation is defined by the open reading frame of the gene encoding the transposase, then, in the vector of the disclosure, one of the first or second sequence is in the sense orientation, while the other is in the anti-sense orientation.

In one embodiment, the first sequence is in the sense orientation and the second sequence is in the anti-sense orientation. In another embodiment, the first sequence is in the anti-sense orientation and the second sequence is in the sense orientation.

Preferably, the sequence of the vector of the disclosure comprises a set of two sequences consisting in a first sequence and a second sequence being respectively derived from, preferably comprising or consisting of a 5' ITR and a 3' ITR of a DNA transposon, wherein one of the first sequence or the second sequence is identical to a 5' ITR or a 3' ITR from a DNA transposon and the other is reverse complementary to a 5' ITR or a 3' ITR from the DNA transposon. In one embodiment, the first sequence is identical to a 5' ITR from a DNA transposon and the second sequence is reverse complementary to a 3'ITR from the DNA transposon. In another embodiment, the second sequence is identical to a 3' ITR from a DNA transposon and the first sequence is reverse complementary to a 5' ITR from the DNA transposon.

The term "reverse complement" or "reverse complementary", when referring to a nucleotide sequence, such as a DNA or RNA sequence, should be construed as generally understood in the art. The reverse complement of a nucleotide sequence of reference can be determined by reversing the letters, interchanging A and T and interchanging C and G. For instance, the reverse complement of ACCTGAG is CTCAGGT, both being read from their 5' end to their 3' end.

Preferably, in the vector of the disclosure, the first sequence and a second sequence of the set of two sequences are respectively derived from a 5' ITR and a 3' ITR of a cut and paste DNA transposon. More preferably, in the vector of the disclosure, the first sequence and the second sequence of the set of two sequences respectively comprise or consist of a 5' ITR and a 3' ITR of a DNA transposon, advantageously a cut and paste DNA transposon. As indicated, in the vector of the disclosure, one of the sequence is in the sense orientation, while the other is in the anti-sense orientation, with respect to the sequence of the promoter.

Several superfamilies of cut-and-paste eukaryotic DNA transposons have been described, which comprise the Tc1/mariner family, the hAT family P element, MuDR/Foldback, CACTA, PiggyBac, PIF/Harbinger, Merlin, Transib and Banshee. ITR from DNA transposon appropriate for the vector of the disclosure include, but are not limited to: ITR from the Tc1/mariner transposons, which include Tc1 and Tc3 from *C. elegans*, Minos from *Drosophila hydei*, Mos1 from *D. mauritiana*, Famar1 from European Earwig (*Forficula auricularia*), Osmar5 from rice (*Oryza sativa*), Fot1 and Impala from the fungus *Fusarium oxysporum*, ISY100 isolated in bacteria, and Mboumar-9 from the ant *Messor bouvieri*. In addition, as well as ITR from the Tc1/mariner transposons which have been reconstructed from inactive elements: Sleeping Beauty from salmonid-type fishes, Himar1 from the Horn Fly (*Hematobia irritans*), Frog Prince from the frog *Rana pipiens* and Hsmar1, incorporated into the SETMAR gene, from *H. sapiens*; ITR from the hAT transposons, which include Tol1, Tol2, and Ac/Ds transposons; ITR from the MuDR/Foldback transposons; ITR from the CACTA transposons; ITR from the PiggyBac transposon; ITR from the PIF/Harbinger transposons; ITR from the Merlin transposons; ITR from the Transib transposons; ITR from the Banshee transposons.

Preferably, in the vector of the disclosure, the first sequence and the second sequence of the set of two sequences are preferably respectively derived from, yet preferably respectively comprise or consist of, 5' ITR and 3' ITR from a DNA transposon chosen in the list consisting of piggyBac, Tol2 and Sleeping Beauty transposons, yet preferably the piggyBac transposons.

In the context of the disclosure, the terms "piggyBac transposon" refer to the piggyBac transposon described in Cary et al., 1989, and the transposons derived therefrom. The sequences of the 5' ITR and 3' ITR from the piggyBac transposon and transposons derived therefrom are well known in the art. For instance, the sequences of the 5' ITR and 3' ITR from the piggyBac transposon have been described in Cary et al., 1989, Fraser et al., 1995 and Fraser et al., 1996, and the sequences of the 5' ITR and 3' ITR derived from the piggyBac transposon have been described in Lacoste et al. (2009).

Preferably, in the context of the disclosure, the sequence derived from a 5' ITR the piggyBac transposon comprises or consists of SEQ ID NO. 1:

TTAACCCTAGAAAGATAGTCTGCGTAAAATTGACGCATGCAT.

Yet preferably, in the context of the disclosure, the sequence derived from a 5' ITR the piggyBac transposon comprises or consists of SEQ ID NO. 2:

TTAACCCTAGAAAGATAGTCTGCGTAAAATTGACGCATG.

Preferably, in the context of the disclosure, the sequence derived from a 3' ITR the piggyBac transposon comprises or consists of SEQ ID NO. 3:

TTAACCCTAGAAAGATAATCATATTGTGACGTACGTTAAAGATAATCAT
GCGTAAAATTGACGCATG.

Advantageously, in the vector of the disclosure, the first sequence and the second sequence of the set of two sequences are preferably respectively derived from, yet preferably respectively comprise or consist of SEQ ID NO. 1 or SEQ ID NO. 2, and SEQ ID NO. 3.Out of the usual transposons active in vertebrate species mentioned above, piggyBac has the higher transposase activity and larger cargo capacity. Furthermore, piggyBac is known to bypass DNA synthesis during cut and paste transposition, and to enable precise excision and regeneration of intact duplex DNA both at the donor site and at the target site. More preferably, in the vector of the disclosure, the first sequence and the second sequence of the set of two sequences are preferably respectively derived from, yet preferably comprise or consist of, 5' and 3' ITR of piggyBac transposon.

In a preferred embodiment, the recombinant vector of the disclosure comprises:
a) a promoter;
b) a gene of interest (GOI);
c) a set of two sequences consisting in a first sequence and a second sequence respectively derived from, preferably respectively comprising or consisting of, 5' and 3' ITR of piggyBac transposon, wherein the sequences are in opposite orientation relative to each other; and wherein,
at least part of the sequence of the gene of interest is in an anti-sense orientation with respect to the sequence of the promoter; and
the sequence of the set derived from, preferably comprising or consisting of, the 5' ITR of piggyBac transposon, is localized downstream of the promoter sequence, in the sense orientation with respect to the orientation of the promoter, and separates the promoter from the at least part of the sequence of the gene of interest which is in an anti-sense orientation with respect to the sequence of the promoter.

In a yet most preferred embodiment, the recombinant vector of the disclosure comprises:
a) a promoter;
b) a gene of interest (GOI);
c) a set of two sequences consisting in a first sequence and a second sequence respectively derived from, preferably respectively comprising or consisting of, 5' and 3' ITR of piggyBac transposon, wherein the sequences are in opposite orientation relative to each other; and wherein,
the sequence of the gene of interest is present in the recombinant vector of the disclosure in the form of two fragments consisting in the 5' terminal part of the gene of interest and the 3'terminal part of the gene of interest, and
the 3' terminal part of the sequence of the gene of interest is in an anti-sense orientation with respect to the sequence of the promoter, and
the 5' terminal part of the sequence of the gene of interest is localized downstream of the promoter sequence and in the sense orientation with respect to the orientation of the promoter; and
one of the two sequences of the set is located between the promoter and the 3' end of the sequence of the gene of interest.

In a preferred embodiment, the recombinant vector of the disclosure comprises:
a) a promoter;
b) a gene of interest (GOI);
c) a set of two sequences consisting in a first sequence and a second sequence respectively derived from, preferably respectively comprising or consisting of, 5' and 3' ITR of piggyBac transposon, wherein the sequences are in opposite orientation relative to each other; and wherein,
the sequence of the gene of interest is present in the recombinant vector of the disclosure in the form of two fragments consisting in the 5' terminal part of the gene of interest and the 3'terminal part of the gene of interest, and
the 3' terminal part of the sequence of the gene of interest is in an anti-sense orientation with respect to the sequence of the promoter, and
the 5' terminal part of the sequence of the gene of interest is localized downstream of the promoter sequence and is in the sense orientation with respect to the orientation of the promoter; and the sequence of the set which is derived from, preferably comprises or consists of, the 5' ITR of piggyBac transposon, is localized downstream of the promoter sequence, is in the sense orientation with respect to the orientation of the promoter and separates the promoter from the 3' end of the sequence of the gene of interest.

As well known in the art and as explained above, the transposon system requires the presence of a transposase enzyme to elicit transgenesis. By "transposase" it is herein referred to an enzyme which binds specifically to the ITR sequences of at least one transposon, and catalyzes the cut and paste mechanism enabling the excision and integration of the transposon in another genome.

Preferably, the vector of the disclosure further comprises a sequence encoding a transposase. More preferably, the sequence encoding a transposase is under the control of the promoter. In this embodiment, it should be understood that the sequence encoding the transposase is localized downstream of the promoter, and its open reading frame is in the same orientation as that of the promoter. Preferably, the promoter and the gene of the transposase are separated by one of the sequences of the set as defined herein. The sequence encoding the transposase may be chosen from any known transposase gene or their respective cDNA. Preferred transposases are those encoded by the transposons listed herein.

Functional variants of a transposase of reference encompass peptides which peptide sequence derives from the sequence of the transposase of reference by insertions, substitutions, and/or deletion, of amino-acid residues at one or more positions of the sequence of reference, and which have retained the ability to specifically bind to the same ITR. Of particular interest are the functional variants which sequence contains conservative substitutions, that is to say wherein amino acids residues of the sequence of reference are substituted for other amino acid residues with similar chemical properties (e.g., charge or hydrophobicity) and therefore do not change the functional properties of the molecule. Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. Preferably, a functional variant of a transposase is a peptide which sequence derives from the sequence of reference by one or more conservative substitutions. Yet preferably, a functional variant of a transposase of reference has a sequence which has at least 80, 85, 90 or 95% identity with the sequence of reference. In a preferred embodiment, a functional variant of a transposase of reference has a sequence which has at least 80, 85, 90 or 95% identity with the sequence of reference and is a peptide which sequence derives from the sequence of reference by conservative substitutions.

In the sense of the present disclosure, the "percentage identity" or "% identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, the comparison being able to be conducted by segment or by using an "alignment window". Optimal alignment of the sequences for comparison can be carried out, in addition to comparison by hand, by means of the local homology algorithm of Smith and Waterman, by means of the similarity search method of Pearson and Lipman (1988) or by means of computer software using these algorithms (GAP, BESTFIT, FASTA and TFASTA in the Wisconsin Genetics Software Package, Genetics Computer Group, 575 Science Dr., Madison, WI, or by the comparison software BLAST NR or BLAST P). The percentage identity between two nucleic acid or amino acid sequences is determined by comparing the two optimally-aligned sequences, in which the nucleic acid or amino acid sequence to compare can have additions or deletions with respect to the reference sequence for optimal alignment between the two sequences. Percentage identity is calculated by determining the number of positions at which the amino acid or nucleotide residue is identical between the two sequences, preferably between the two complete sequences, dividing the number of identical positions by the total number of positions in the alignment window and multiplying the result by 100 to obtain the percentage identity between the two sequences.

A transposase may have different affinities for each set of ITR. Typically, in transposon-based transgenesis systems, it is preferable to use a transposase which recognizes, i.e. binds specifically to, the ITR-derived sequences used in the vector. This can be achieved by selecting a transposase originating from the same transposon family as the transposon, and in particular the ITR sequences, from which the set of two sequences as defined herein are derived.

Preferably, the vector of the disclosure comprises a sequence encoding a transposase specific of the ITR sequences from which the set of two sequences comprised in the vector of the disclosure are derived. In the context of the disclosure, a transposase is specific of ITR sequences when it is capable of binding specifically thereto, and of inducing transposition.

Advantageously, in the vector of the disclosure, the first sequence and the second sequence of the set of two sequences as defined herein are respectively derived from, yet preferably respectively comprise or consist of, 5' ITR and 3' ITR from the DNA transposons piggyBac, and the vector of the disclosure comprises a sequence encoding a piggyBac transposase, yet preferably under the control of the promoter. Advantageously, in the vector of the disclosure, the first sequence and the second sequence of the set of two sequences as defined herein are respectively derived from, yet preferably respectively comprise or consist of, 5' ITR and 3' ITR from the DNA transposons Tol2 and the vector of the disclosure comprises a sequence encoding a Tol2 transposase, yet preferably under the control of the promoter. Advantageously, in the vector of the disclosure, the first sequence and the second sequence of the set of two sequences as defined herein are respectively derived from, yet preferably respectively comprise or consist of, 5' ITR and 3' ITR from the DNA transposons Sleeping Beauty and the vector of the disclosure comprises a sequence encoding a Sleeping Beauty transposase, yet preferably under the control of the promoter.

In vector based on the piggyBac system, such as classic piggyBac transposons, action of the transposase may lead to unwanted auto or inter integration in the episomal form of the piggyBac based vector itself (Wang et al., 2014), or in the vector encoding the piggyBac transposase. To reduce the possibility of inter-episomal integration, and thus favor genomic integration, in embodiments wherein the first sequence and the second sequence of the set of two sequences as defined herein are respectively derived from, yet preferably respectively comprise or consist of, 5' ITR and 3' ITR from the DNA transposons piggyBac, the recombinant vector of the disclosure does not contains TTAA sites except for those which are at the extremities of the 5' ITR and 3' ITR. In other terms, in the embodiments, preferably, the recombinant vector of the disclosure does not contain the sequence TTAA more than twice in its sequence. Should the person skilled in the art use a classic vector backbone to produce the recombinant vector of the disclosure, the above embodiments can easily be obtained by substituting T or A residues in the classic backbone vector in ways that do not affect the functionalities of the vector, such as its ability of the vector to replicate in bacteria or its function in the host cell.

The recombinant vector of the disclosure may be produced using established methods and techniques of molecular biology. These methods and techniques are well known in the field, and fully detailed for instance in *Molecular Cloning: A Laboratory Manual*, by Michael R. Green and Joseph Sambrook (Cold Spring Harbor Laboratory press, Fourth Edition, 2002), and the article of Gibson et al. (2009) which the person skilled in the art may refer to.

To facilitate implementation of the method of the disclosure, the inventors have further developed empty recombinant vectors which already comprise the set of integration sequence according to the disclosure, in the appropriate orientation, and multicloning sites, in which the end user, i.e. the person skilled in the art, can easily integrate a GOI and a promoter of his choice. In the context of the disclosure, the terms "empty recombinant vector" refer to a vector which does not comprise a gene of interest as defined herein, but may include a reporter gene, and/or a gene encoding a selection marker as defined herein.

The disclosure therefore further pertains to an empty recombinant vector, preferably to be used for producing the recombinant vector of the disclosure, comprising
 a) a first multi-cloning site;
 b) a second multi-cloning site;
 c) a set of two sequences consisting of a first sequence and a second sequence being respectively derived from, preferably comprising or consisting of, a 5' ITR and a 3' ITR of a DNA transposon, wherein the sequences are in opposite orientation relative to each other;
wherein one of the two sequences of the set is located between the first and the second multi-cloning site.

Preferably, the empty recombinant vector of the disclosure comprises a promoter, as defined herein. Preferably, the empty recombinant vector of the disclosure comprises at least a reporter gene, and/or a gene encoding a selection marker as defined herein, wherein the open reading frame of the genes are in the same orientation. In a preferred embodiment, the empty recombination vector comprises a promoter and at least a reporter gene, a gene encoding a selection marker or a gene encoding a protein tag, wherein one of the two sequences capable of inducing the integration of a polynucleotide sequence in a genome is located between the promoter and the reporter gene, the gene encoding a selection marker and/or the gene encoding a protein tag and wherein the open reading frame of the genes is in an anti-sense orientation with respect to the orientation of the promoter.

The recombinant vector of the disclosure, as well as the empty recombinant vector defined herein, may be used for molecular biology purpose, as well as for therapeutic uses, which are detailed thereafter. In this context, these vectors may be formulated in compositions appropriate for their intended use.

The disclosure further pertains to a composition comprising the empty recombinant vector or the recombinant vector of the disclosure, and a pharmaceutically acceptable carrier.

The disclosure further pertains to a kit comprising the empty recombinant vector or the recombinant vector of the disclosure, and a transposase enzyme. The transposase enzyme may be provided as a protein, or in the form of a transposase expression vector.

In the context of the disclosure, a transposase expression vector is a vector comprising a sequence encoding the transposase and enabling its expression. Advantageously, the transposase expression vector of the disclosure comprises a sequence encoding the transposase under the control of a promoter, and preferably operably linked to a polyadenylation signal.

The disclosure further pertains to the use of the above-disclosed recombinant vector, composition or kit comprising thereof, for the integration of a sequence encoding a gene of interest in the genome of a host cell.

Preferably, when used for transgenesis, the vector of the disclosure comprises a sequence encoding a transposase. Alternatively, in order to achieve transgenesis of the gene of interest in the genome of the host, the recombinant vector of the disclosure is used in combination with a transposase expression vector, as defined above.

As indicated above, the vector of the disclosure according to the first embodiment disclosed above, once introduced in a host cell, enables efficient introduction of the gene of interest in the genome of the host cell, provided a transposase, preferably adapted to the vector of the disclosure, is present in the host cell.

As already indicated, the transposase may be provided as a sequence encoding thereof comprised in the vector of the disclosure, under the control of a promoter and preferably operably linked to a polyadenylation signal. Alternatively, the transposase may be provided in the form of a transposase expression vector.

The disclosure further pertains to a method for the integration of a gene of interest in the genome of a host cell, the method comprising the steps of:
 a) transfection of a recombinant vector according to the disclosure in a host cell;
 b) optionally, transfection of a transposase enzyme in the host cell.

As taught herein, the vector of the disclosure preferably comprises a sequence encoding a transposase, yet preferably under the control of a promoter and operably linked to a polyadenylation signal. Alternatively, in order to achieve transgenesis of the gene of interest in the genome of the host, the vector of the disclosure is used in combination with a transposase enzyme, which may be provided as a protein, or in the form of a transposase expression vector, as defined above.

The recombinant vector may be transfected in the host cell of choice using any of the usual techniques known in cell biology, such as for instance chemical-based transfection (using for example cyclodextrin, polymers, liposomes, or nanoparticles), electroporation, cell squeezing, microinjection, or sonoporation.

In the context of the disclosure, the host cell is preferably a eukaryotic cell, yet preferably a mammalian cell.

The method of the disclosure therefore enables the generation of recombinant host cells, comprising the recombinant vector of the disclosure.

The disclosure further pertains to recombinant host cells susceptible to be obtained by the method for the integration of a gene of interest detailed above, preferably wherein the promoter and the gene of interest as defined above have been integrated in the genome of the host cell. Such recombinant host cells may easily be identified and/or selected based on their ability to express the product of the gene of interest.

In addition, it is well known that the piggyBac transposon system has a specificity of DNA integration site which comprise the sequence TTAA. Because of the molecular mechanism involved in DNA transposon integration discussed herein, transgenesis performed using piggyBac transposon systems usually results in the duplication of this target sequence (TTAA) in the genome, each of the TTAA sequences flanking the transgene, which, together with the presence of piggyBac ITR sequences, can be considered as the typical "piggyBac footprint". However, because the vector of the disclosure relies on a very different arrangement of its elements (promoter, gene of interest and set of sequences derived from ITR sequences from, preferably comprising or consisting of DNA transposon), recombinant host cells obtained using a recombinant vector according to the disclosure comprising a set of two sequences derived from 5' and 3' ITR of piggyBac transposon have, in their genome, a different and specific footprint. This footprint can be defined as the presence of a TTAA motif localized in the genome of the recombinant host cells, between the sequence of a promoter and that of a gene of interest, the promoter and gene of interest being further preferably flanked by sequences derived from 5' and 3' ITR of piggyBac transposon.

Thus, in embodiments wherein the recombinant host cells are obtained using a recombinant vector according to the disclosure comprising a set of two sequences consisting in a first sequence and a second sequence respectively derived from, preferably comprising or consisting of 5' and 3' ITR of piggyBac transposon, the host cells preferably comprise, in their genome, TTAA motif localized between the sequence of a promoter and that of a gene of interest, the promoter and gene of interest being advantageously flanked by sequences derived from 5' and 3' ITR of piggyBac transposon.

The disclosure further pertains to the recombinant vector of the disclosure, or a pharmaceutical composition comprising thereof, and/or a recombinant host cell as defined above, for use as a medicament.

DESCRIPTION OF THE FIGURES

FIGS. 1A-1D: Principle and validation of the PB-ID transcriptional switch enabling transposition-dependent expression based on the piggyBac system FIG. 1A: Classic transposon vector (PBCAG::RFP, left), and transgene configuration enabling transposition dependent transcription of a GOI based on the piggyBac transposition system (PB-IDCAG∞RFP, right). FIG. 1B: Validation in vitro in HEK-293 cells, analyzed 3 days after transfection by epifluorescence imaging (top) and FACS analysis (bottom). Graphs compare transfected and control cells transfected with non-fluorescent plasmids. RFP is only expressed from the PB-IDCAG∞RFP vector in presence of PBase, while it is active in the episomal form of the classic transposable vector. FIG. 1C: Time-course analysis of fluorescent protein expression in HEK-293 cells after transfection of episomal, transposon-based and PB-ID vectors. FIG. 1D: Validation in vivo of the PB-ID switch in the embryonic chicken spinal (electroporation at E2, analysis at E6 in whole-mount spinal cord preparations). An episomal vector (CAG::Cerulean) is found in isolated neurons born shortly after electroporation, while the PB-ID vector labels radial clones of neurons migrating from the ventricular surface FIGS. 2A-2B2: Transgene configurations for transposition-dependent GOI expression FIG. 2A: Four distinct PB-ID configurations (PB-ID 1A, 1B, 2A, 2B) can be envisioned depending on the relative arrangement and orientation of the piggyBac ITRs, promoter and GOI. FIG. 2B1 and FIG. 2B2: Validation of PBase-dependent expression with three PB-ID configurations in HEK-293 cells (epifluorescence imaging 3 days after transfection).

FIG. 3A: Configuration of an "all-in-one" PB-ID vector in which the piggyBac transposase (PBase) is initially expressed by episomal ID vectors, and where expression switches to that of a GOI upon transposition (PB-IDCAG::PBase∞RFP). FIG. 3B: Validation in HEK-293 cells (epifluorescence imaging and FACS analysis 3 days after transfection).

FIGS. 4A-4B2: Principle of the PB-ID translational switch and vectors driving expression of three distinct fluorescent proteins FIG. 4A: Configuration of PB-ID vectors in which full translation of EGFP, mRFP1 or IRFP670, initially blocked, is activated by genome integration mediated by the piggyBac transposase (PB-zIDCAG∞EGFP, PB-zIDCAG∞RFP, PB-zIDCAG∞IRFP). FIG. 4B1 and FIG. 4B2: Validation in HEK-293 cells. Epifluorescence imaging and C: FACS analysis 3 days after transfection of PB-IDCAG∞RFP (left) vs. PB-zIDCAG∞RFP (right) in absence of PBase.

FIGS. 5A-5B2: Transposition-dependent Cre recombination with the PB-ID translational switch FIG. 5A: Configuration of PB-ID vector in which full translation of Cre, initially blocked, is activated by genome integration mediated by the piggyBac transposase (PB-zIDCMV∞Cre). FIG. 5B1 and FIG. 5B2: Validation in HEK-293 cells stably expressing a floxed reporter transgene (CAG::loxP-mCherry-loxP-EYFP) switching from RFP to YFP expression upon Cre action (top). Epifluorescence images were acquired 3 days after transfection of the three vectors in presence (left) or absence of PBase (right). Immunostaining with an anti-FLAG antibody confirms expression of Cre in a PBase-dependent manner (bottom).

Validation in HEK-293 cells A normal (left) and modified PB-ID vector (right) were transfected in HEK-293 cells. In the modified vector (PB-zIDCAG∞RFP), TTAA sites have been mutated to prevent PBase-mediated suicidal integration of one copy of the vector into another copy (auto-integration), with the exception of TR sites. The modified vector drives efficient RFP expression in presence of PBase.

FIGS. 7A1-7B: Experimental manipulation of cell phenotype with the PB-ID switch

Figure 7B:
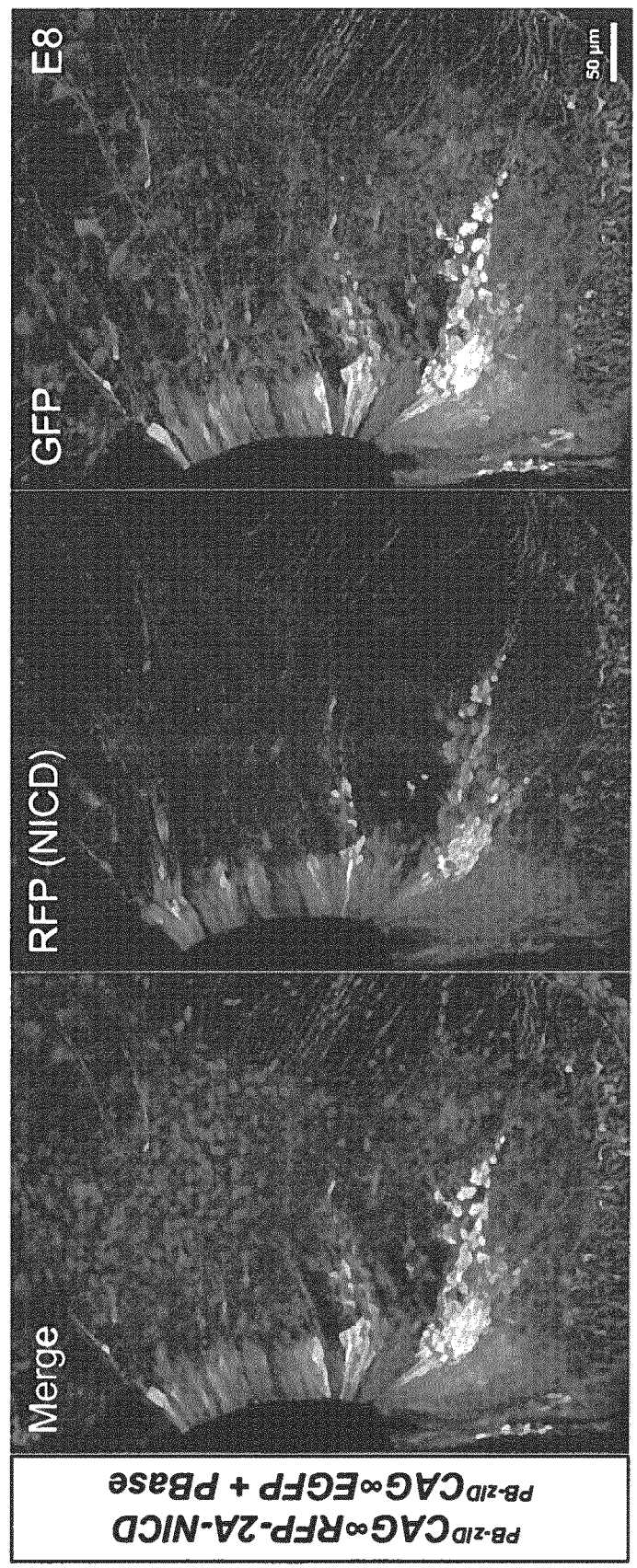

FIG. 7A1 to FIG. 7A3. Effect of a PB-ID vector co-expressing the Notch intracellular receptor (NICD) along with RFP (PB-zIDCAG∞RFP-2A-NICD), 3 days after electroporation in the embryonic chicken spinal cord. Strong and sustained inhibition of neurogenesis is observed (left) compared to the control situation (absence of perturbation, right). A vector transiently expressing NICD shows less pronounced effect (middle). FIG. 7B: The same phenotype is observed in the dorsal chicken spinal cord 6 days after electroporation with the PB-zIDCAG∞RFP-2A-NICD and PB-zIDCAG∞EGFP in presence of PBase.

Figure 8A:
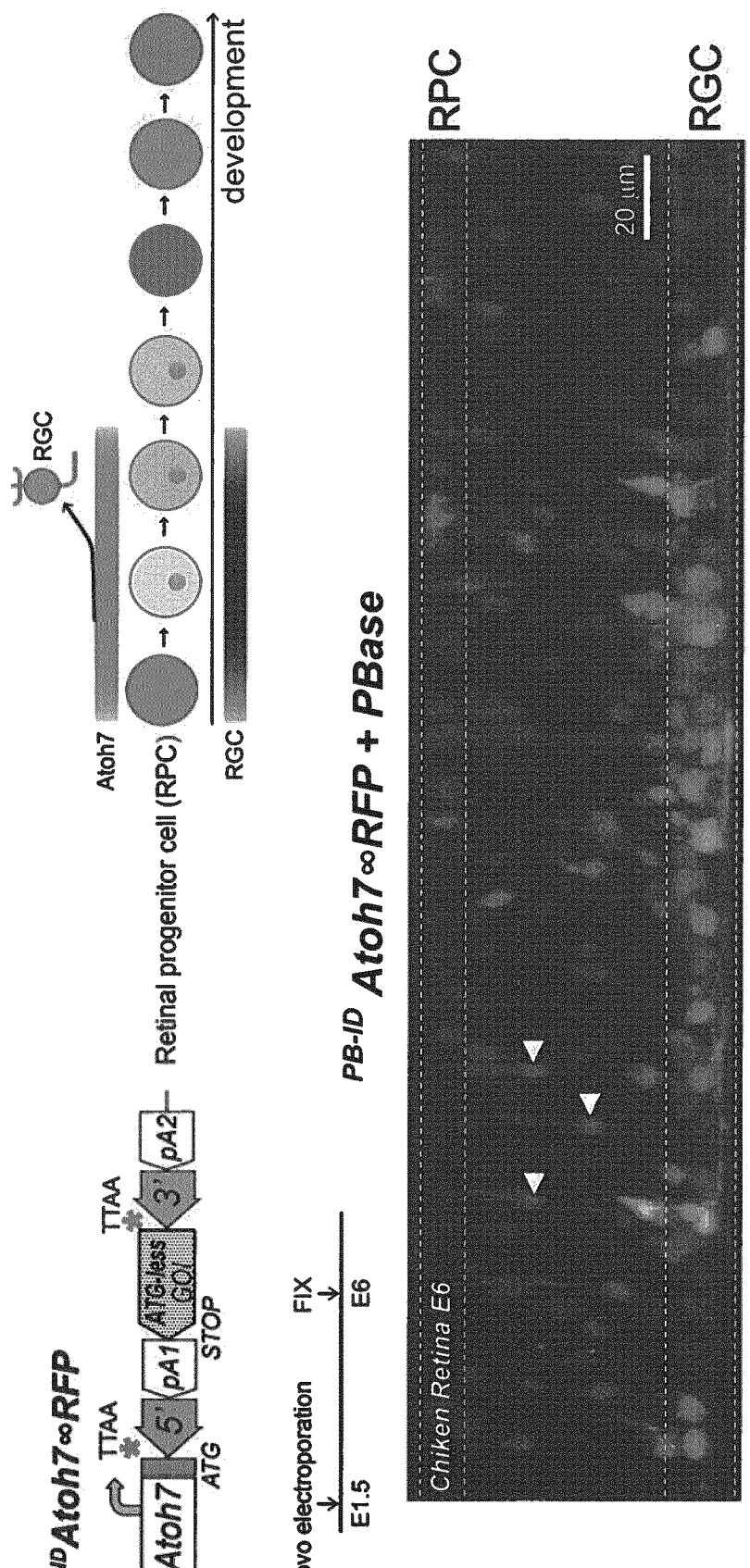
Figure 8B:
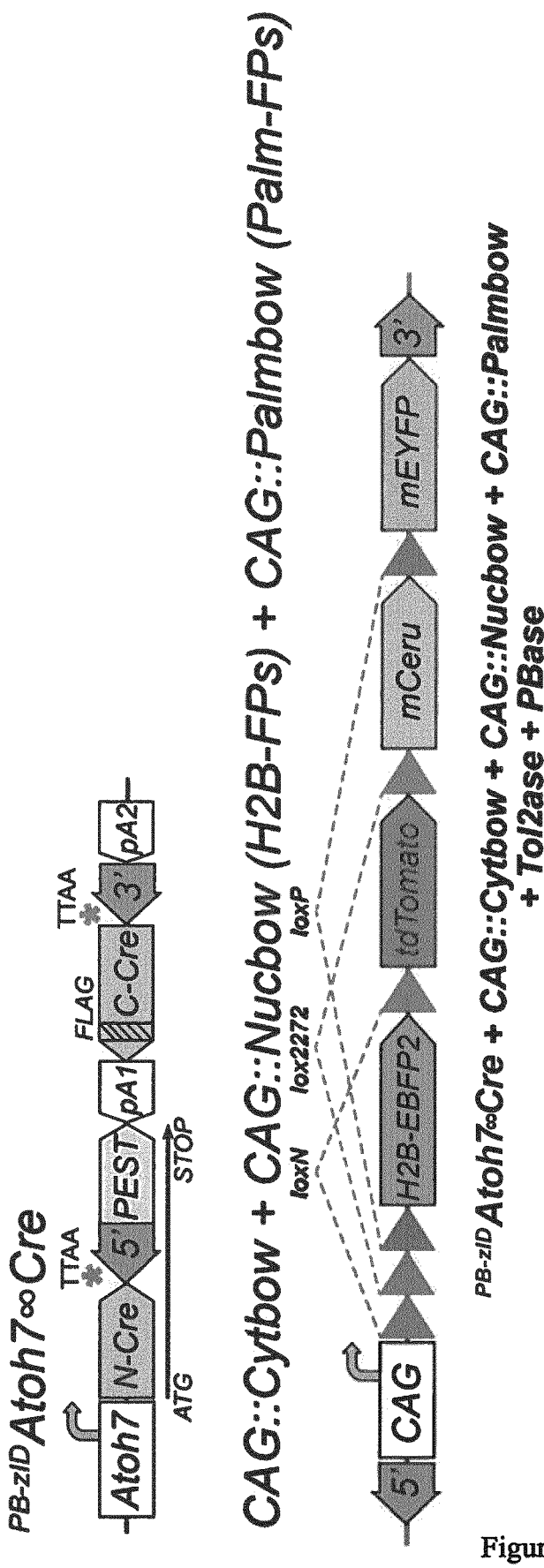
Figure 8B:
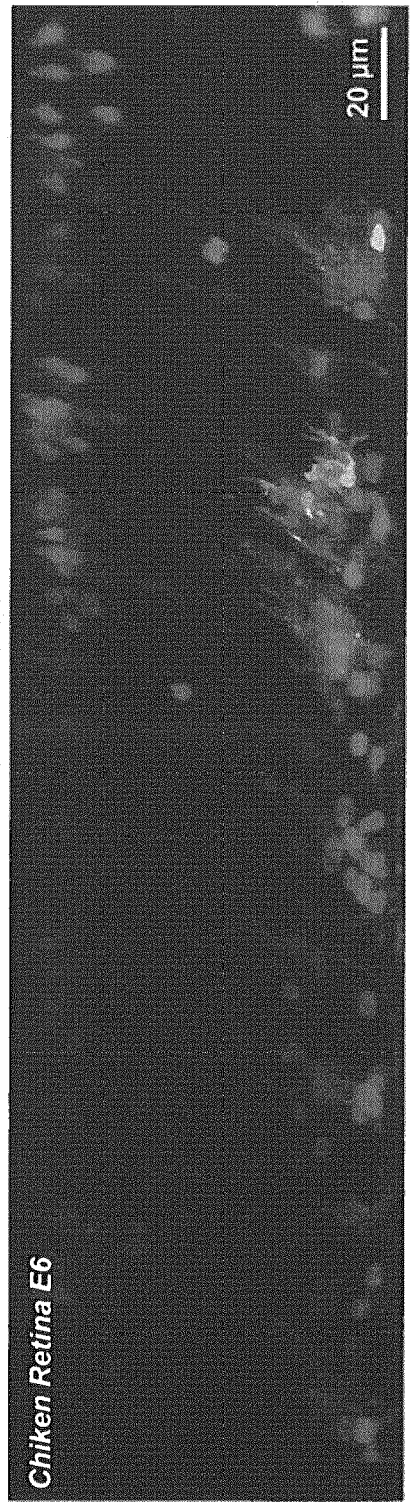

FIGS. 8A-8B: PB-ID vectors in which expression of a GOI is controlled by regulatory sequences of interest FIG. 8A: View across the retina of an E6 chicken embryo 5 days after electroporation of a PB-zIDAtoh7∞RFP vector expressing RFP under the control of the Atoh7 promoter, active in subsets of retinal neurons. The expected restriction of transgene expression in retinal ganglion cells is observed. FIG. 8B: A similar pattern is observed with electroporation of a PB-zIDAtoh7∞Cre vector along with "floxed" multicolor reporter transgene (nuclear, cytoplasmic and membrane-bound Brainbow transgenes; Loulier et al., 2014).

Figure 9A:
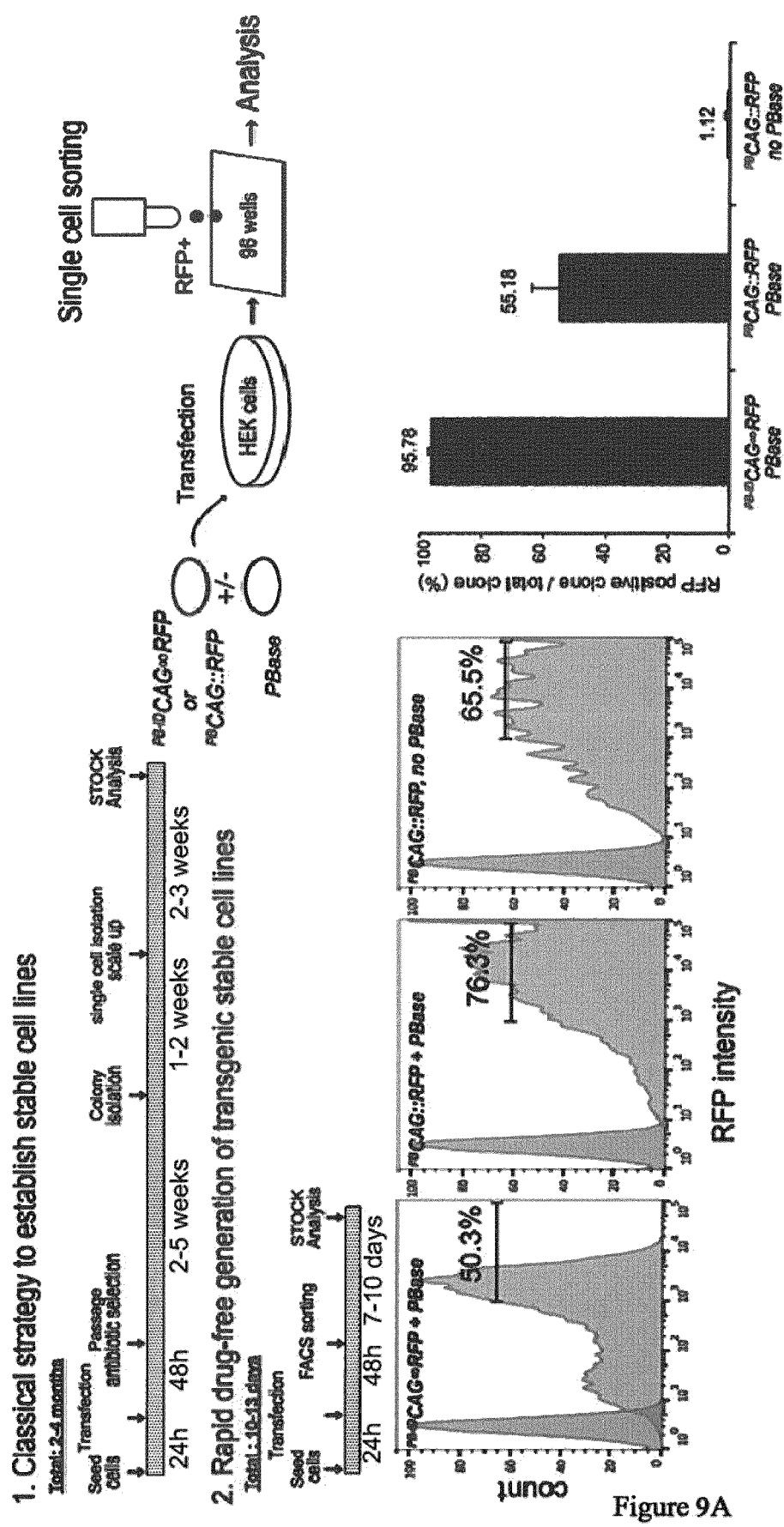
Figure 9B:
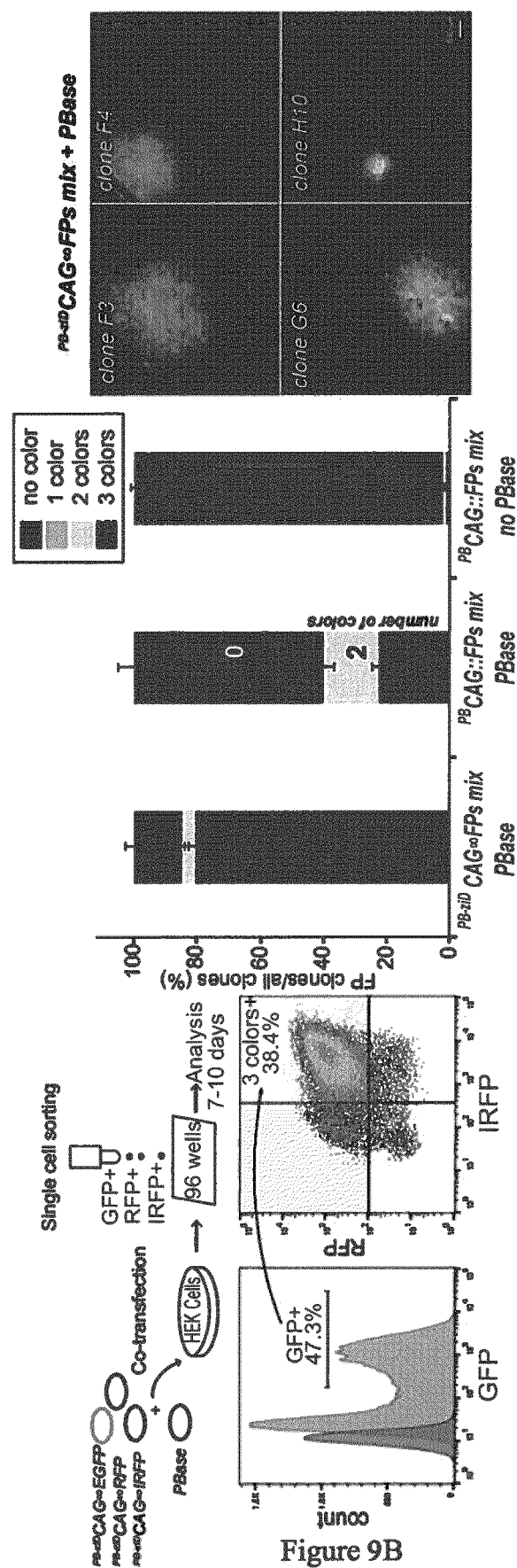

FIGS. 9A-9B: Rapid selection of cell lines expressing one or more transgenes with PB-ID FIG. 9A: Comparison of classic and PB-ID-based protocols to establish stably transfected cell lines in vitro (top). Sorting of cells expressing RFP from a PB-IDCAG∞RFP vector or a classic transposon vector (PBCAG::RFP) two days after transfection results in a higher yield of RFP+ clones in the first case (bottom). FIG. 9B: Establishment of triple transgenic cell lines co-expressing RFP, GFP, IRFP with high yield using the PB-ID switch.

Figure 10A:
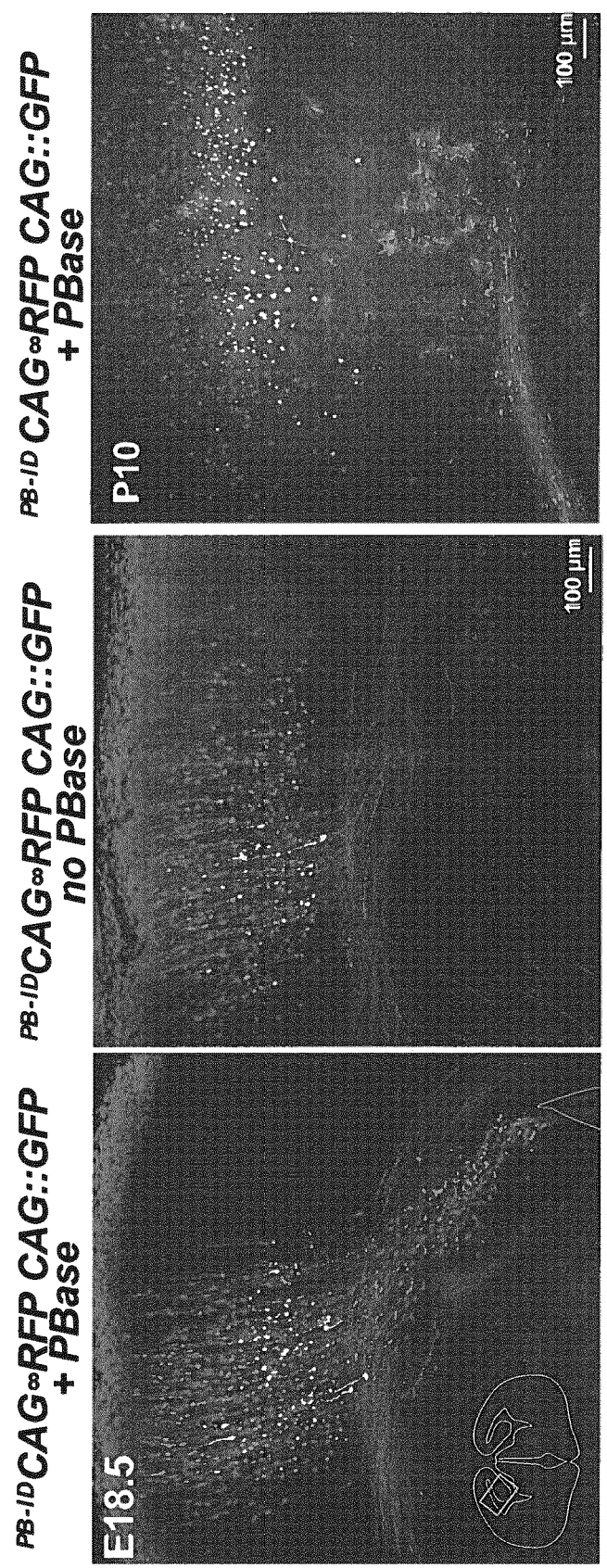
Figure 10B:
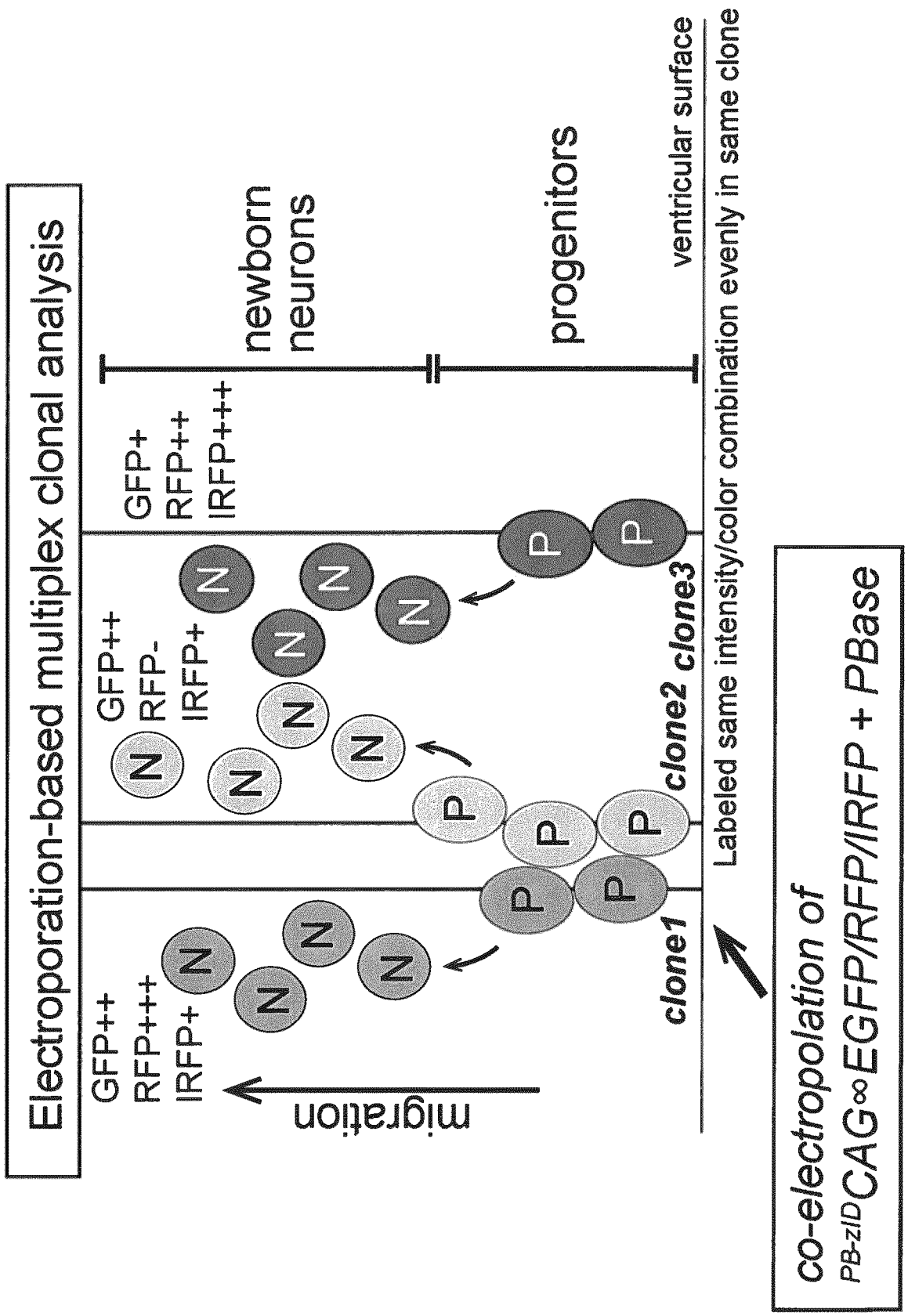
Figure 10C:
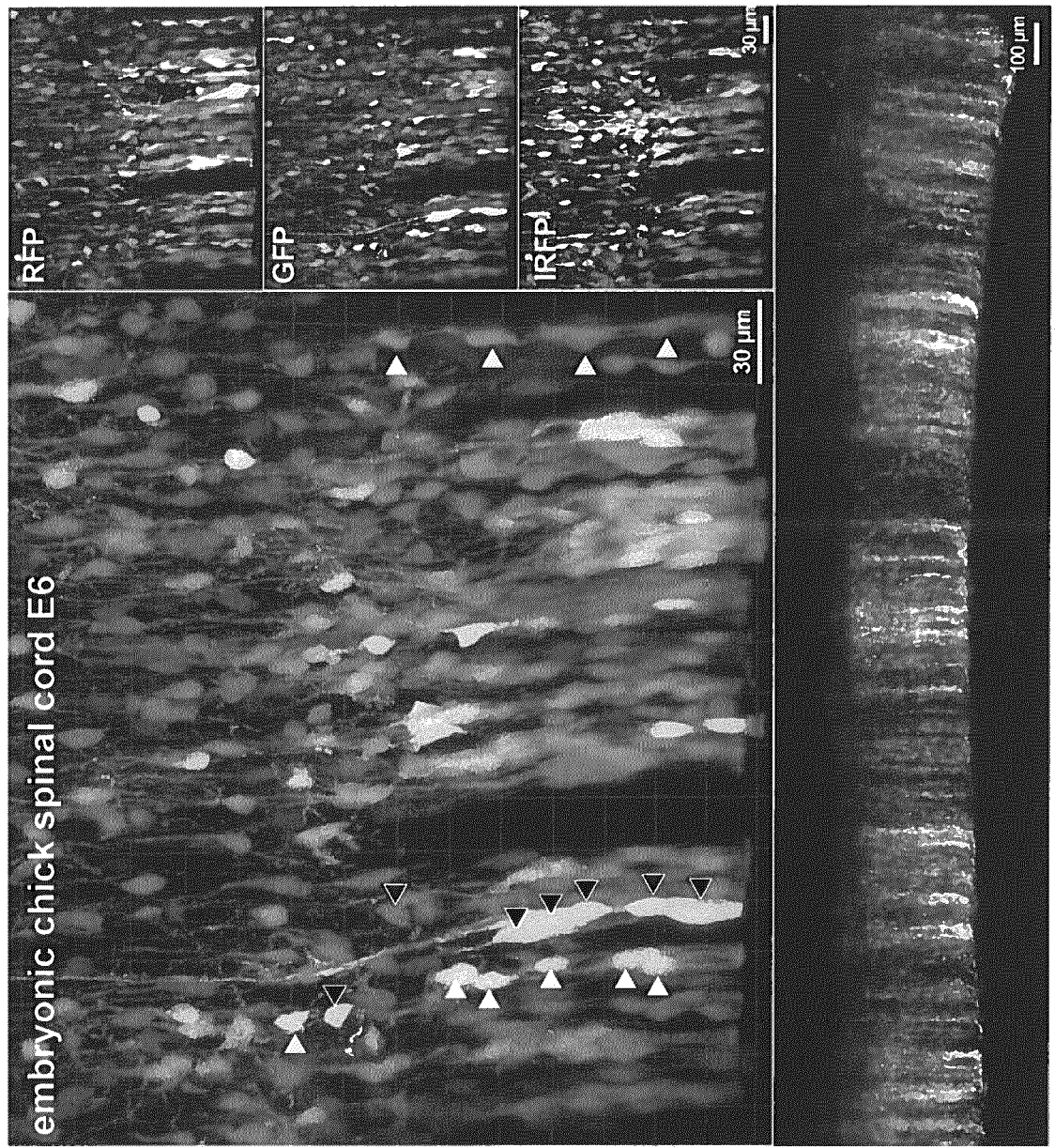

FIGS. 10A-10C: Cell lineage tracing and clonal analysis with PB-ID vectors

FIG. 10A: Embryonic electroporation of a PB-IDCAG∞RFP vector in the mouse cerebral cortex yields at E18.5 streams of neurons that migrate radially from the ventricular surface, while an episomal plasmid (CAG::GFP) labels only cells born shortly after the electroporation (left). At P10, astrocytes are also labeled with the PB-IDCAG∞RFP vector but not the CAG::GFP plasmid, demonstrating long term integration and expression of the PB-ID vector. FIG. 10B, FIG. 10C: Multicolor clonal analysis with PB-ID vectors. Combinations of fluorescent protein markers expressed at different levels identify clones of neural cells migrating radially from the ventricular surface.

Comparison of classic and PB-ID-based protocols to establish stably transfected cell lines in vitro (top). Sorting of cells expressing RFP from a PB-IDCAG∞RFP vector or a classic transposon vector (PBCAG::RFP) two days after transfection results in a higher yield of RFP+ clones in the first case (bottom)

FIGS. 11A-11D: PB-ZID vector expression in cultured cells.

Figure 11A:
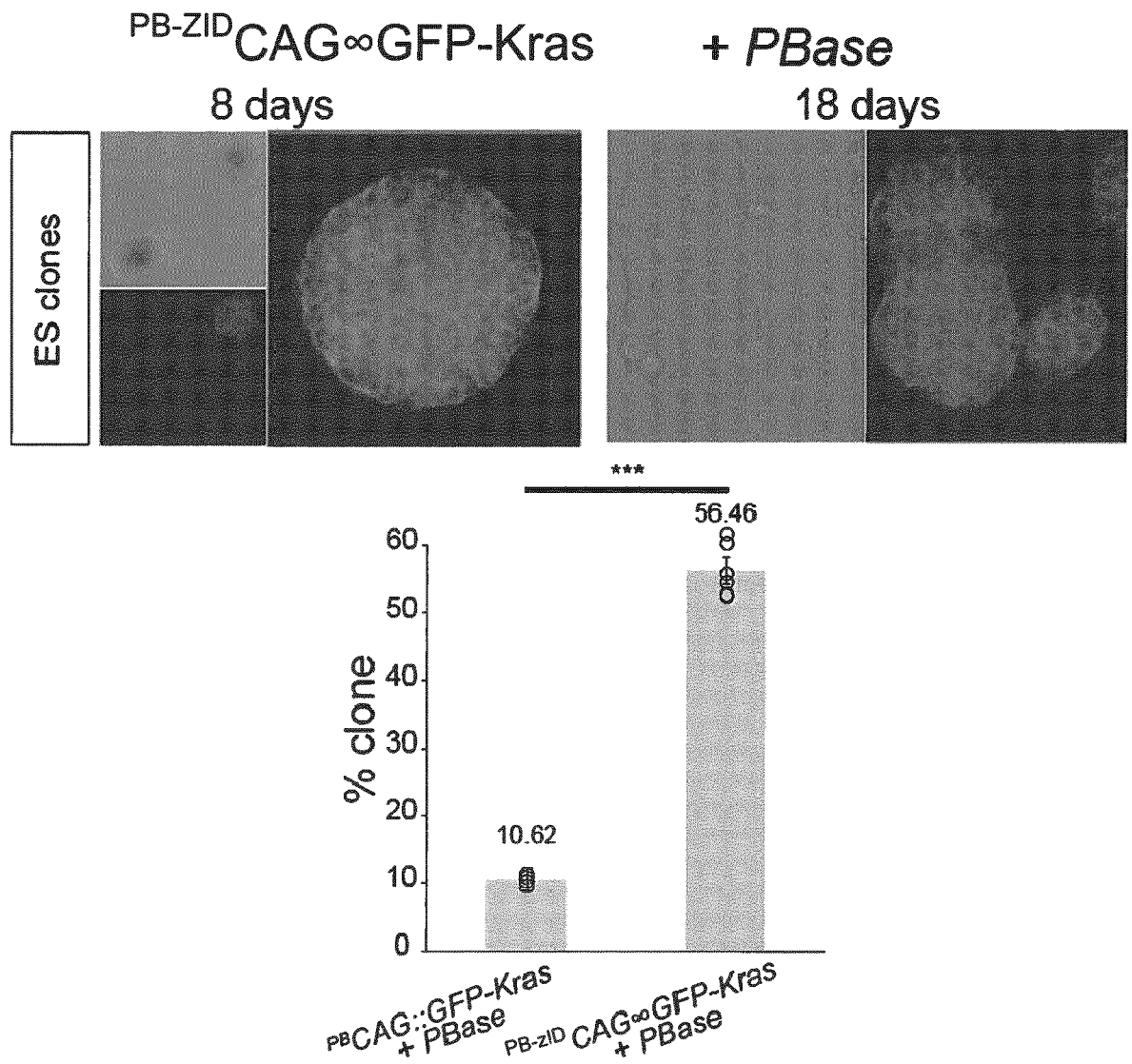
Figure 11D:
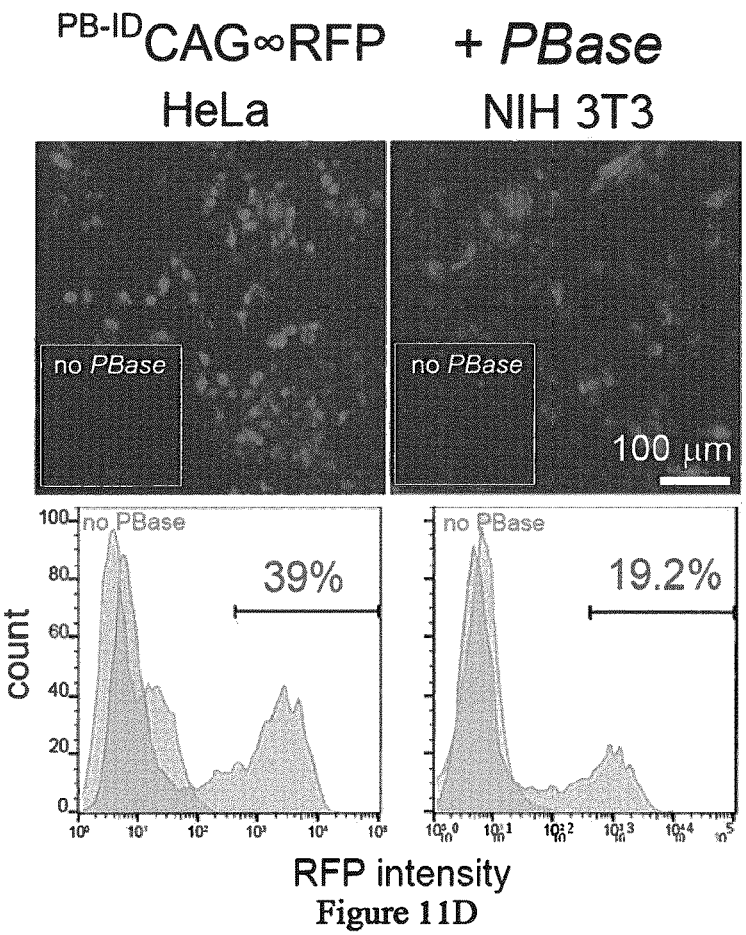

FIG. 11A, Top: mouse embryonic stem (ES) cell clones grown for 8 and 18 days after sorting of cells expressing a PB-zID vector encoding the GFP protein (PB-zIDCAG∞GFP-Kras), sorting being performed two days after transfection. Left: low magnification picture showing GFP-positive and negative ES cell clones. Right: higher magnification of a positive clone showing membrane localization of GFP in all cells of the clone. Bottom: Comparison of a classic transposon vector (PBCAG::GFP-Kras) and the PB-zIDCAG∞GFP-Kras vector. Sorting of cells from a PB-zIDCAG∞GFP-Kras vector results in a higher yield of GFP-positive clones compared to cells from a PBCAG::GFP-Kras vector. Values and error bars represent the mean and s.e.m or four distinct replicates (dots). A $\chi^2$ test indicated a significant difference between the two situations (p<0, 001). FIG. 11B: Assessment of cell viability by Trypan blue assay, 2 days after HEK293 cells transfection with PB-zID and control vectors. >95% survival is observed in all conditions. FIG. 11C: Survival of clones at 10 days, established from single RFP-positive cells sorted after transfection with PBCAG::RFP and PB-IDCAG∞RFP, in presence of PBase (measurements from the experiment presented in (FIG. 9A). FIG. 11D: PBase-dependent expression from an PB-IDCAG∞RFP vector in HeLa and NIH 3T3 cells, 3 days after transfection in presence and absence of PBase (top: epifluorescence imaging, bottom: FACS analysis).

Figure 12:
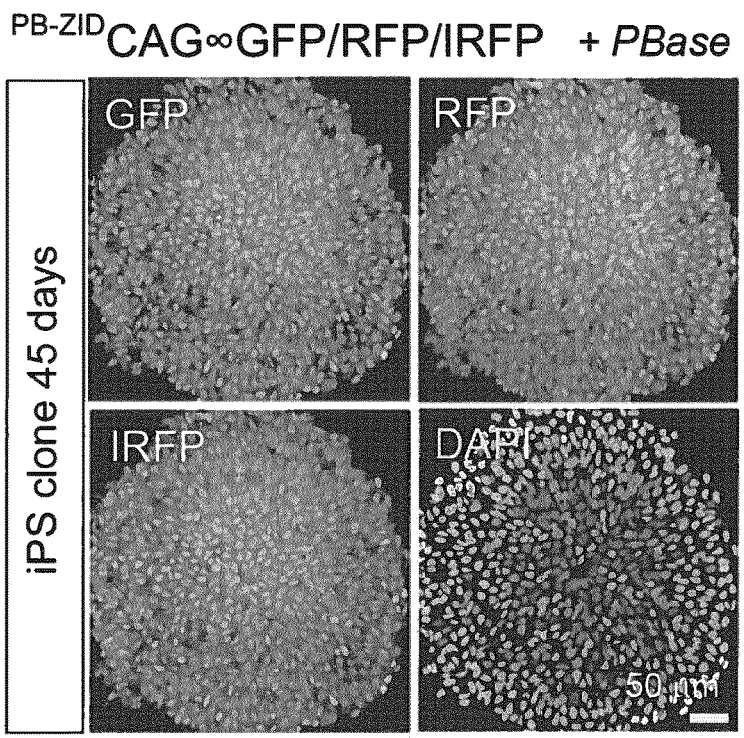

FIG. 12: Highly efficient multiplexed stable transfection with PB-ID vectors.

Example of human iPS cell clones derived from cells co-transfected with the three-color PB-zIDCAG∞FP vectors, grown 45 days. All cells co-express the three fluorescent proteins FPs (GFP, RFP and IRFP).

Figure 13A:
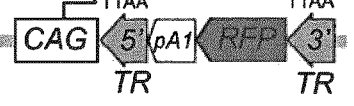
Figure 13B:
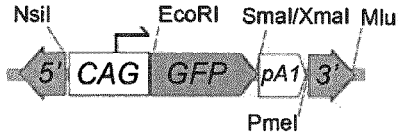

FIGS. 13A-13B: Schematic map of the transgenes. All constructs were assembled in a pUC57-mini plasmid backbone. Restriction sites available to exchange GOIs and promoters are indicated. A PB-ID vector equipped with a multi-cloning site was also designed to facilitate the cloning of varied GOIs. pA1, pA2, pA3: bGH, rabbit beta-globin and SV40 transcription terminators. P: PEST degradation signal.

Figure 14A:
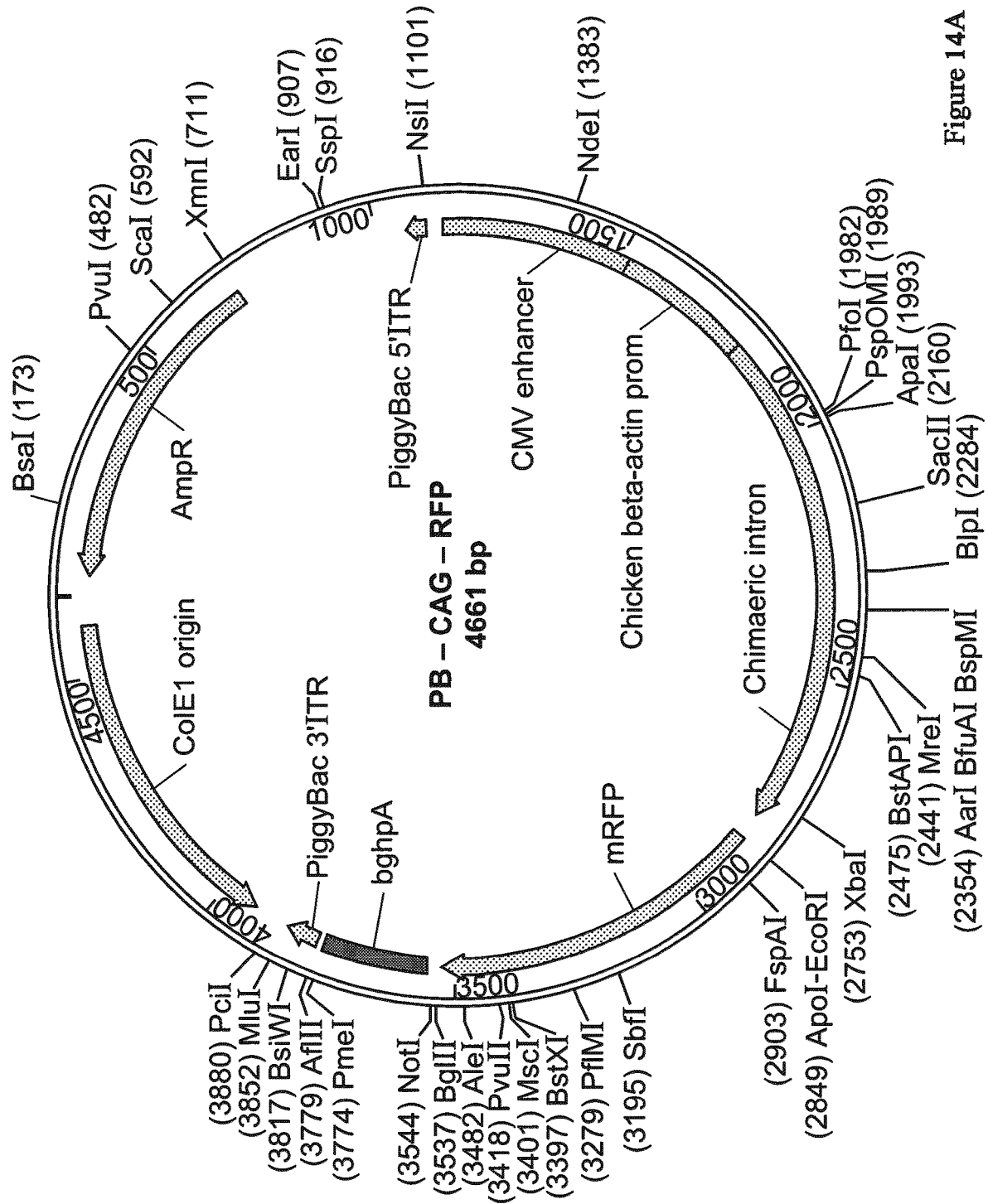

FIGS. 14A-14B2: FIG. 14A. Map of a classic transposon vector based on the piggyBac system, driving expression of mRFP under the control of a CAG promoter (CMV early enhancer+chicken beta-actin promoter+rabbit beta globin splice acceptor), and enabling transposition of the CAG::RFP cassette by the PBase transposase. FIG. 14B1 and FIG. 14B2: Sequence of the PB-CAG::RFP vector. The piggyBac 5' ITR and 3' ITR are underlined in the sequence. This sequence contains the following elements: the coding sequence of the gene RFP, from nucleotide 2858 to nucleotide 3529, the coding sequence of the gene AmpR, from nucleotide 42 to nucleotide 701, the CMV enhancer, from the nucleotide 1133 to nucleotide 1513, the piggyBac 3'ITR, from nucleotide 3785 to nucleotide 3851, the piggyBac 5'ITR, from nucleotide 1061 to nucleotide 1102 and the chicken β-actin promoter, from nucleotide 1516 to nucleotide 1791.

Figure 15A:
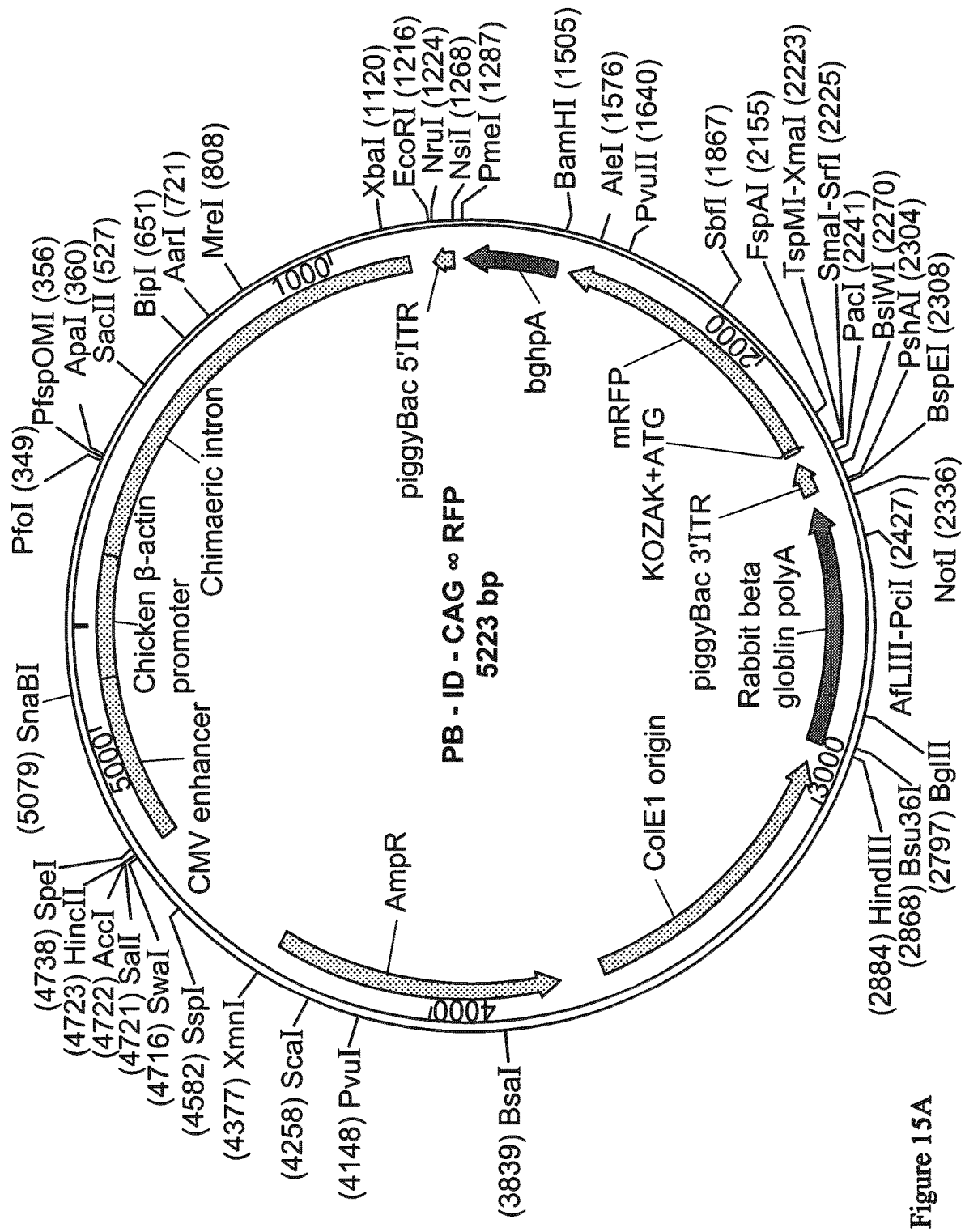

FIGS. 15A-15B2: FIG. 15A. Map of a plasmid vector based on the PB-ID switch, driving PBase-dependent expression of mRFP under the control of a CAG promoter (CMV early enhancer+chicken beta-actin promoter+rabbit beta globin splice acceptor).

FIG. 15B1 and FIG. 15B2: Sequence of the PB-IDCAG∞RFP vector. The piggyBac 5' ITR and 3' ITR are underlined in the sequence. This sequence contains the following elements: the piggyBac 3'ITR, from nucleotide 2241 to nucleotide 2307, the rabbit β-globin polyA, from the nucleotide 2343 to nucleotide 2881, the sequence KOZAK+ATG, from the nucleotide 2202 to nucleotide 2210, the CMV enhancer, from the nucleotide 1133 to nucleotide 1513, the coding sequence of the gene AmpR, from nucleotide 3708 to nucleotide 4367, the coding sequence of the gene RFP, from nucleotide 1530 to nucleotide 2020, the chicken β-actin promoter, from nucleotide 5106 to nucleotide 5223 and from nucleotide 1 to nucleotide 158, and the piggyBac 5'ITR, from nucleotide 1228 to nucleotide 1269.

Figure 16A:
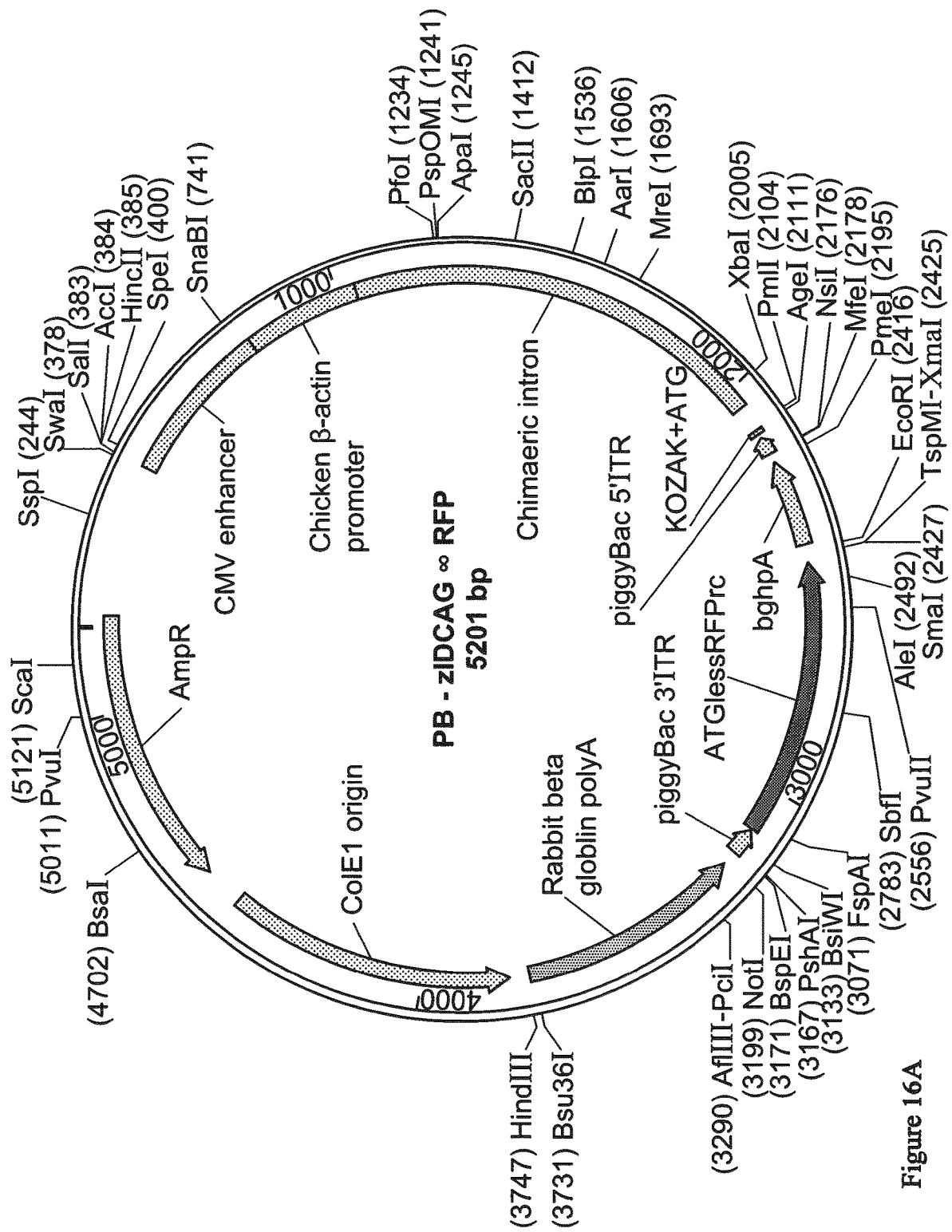

FIGS. 16A-16B2: FIG. 16A. Map of a plasmid vector based on the PB-zID switch, driving PBase-dependent expression of mRFP under the control of a CAG promoter (CMV early enhancer+chicken beta-actin promoter+rabbit beta globin splice acceptor). FIG. 16B1 and FIG. 16B2: Sequence of the PB-zIDCAG∞RFP vector. The piggyBac 5' ITR and 3' ITR are underlined in the sequence. This sequence contains the following elements: the chicken β-actin promoter, from nucleotide 768 to nucleotide 1043, the rabbit β-globin polyA, from the nucleotide 3206 to nucleotide 3744, the sequence "ATGlessRFPrc", from nucleotide 2446 to nucleotide 3102, the sequence KOZAK+ATG, from nucleotide 2117 to nucleotide 2125, the piggyBac 5'ITR, from nucleotide 2136 to nucleotide 2177, the CMV enhancer, from nucleotide 385 to nucleotide 765, the coding sequence of the gene AmpR, from nucleotide 4574 to nucleotide 5201 and from nucleotide 1 to nucleotide 29, and the piggyBac 3'ITR, from nucleotide 3104 to nucleotide 3170.

Unless it is otherwise specified, in the FIGURES illustrating a vector:
- the ITRs are illustrated by an arrow of which the head points the transposase cutting site,
- the promoter is illustrated by a rectangle surmounted by an arrow, the arrow being directed in the sense of the sequence of the promoter,
- the gene of interest (GOI) is illustrated by an arrow, the arrow being directed in the sense of the open reading frame.

EXAMPLE

A. Material and Methods

Cultured cells. Human embryonic kidney (HEK293T), HeLa and 3T3 cells were cultured in 10% fetal bovine serum in Dulbecco modified Eagle medium (DMEM, Life technologies). Human induced pluripotent stem cells (iPS line WTSIi008-A, EBiSC, UK) were cultured in E8 medium (Life technologies) on Geltrex coating (Life technologies) and passaged with EDTA. Mouse ES cells (C57BL/6×129/Sv, line KH2) (Beard et al., 2006) were cultured on primary embryonic fibroblasts feeder cells.

Mice. Swiss strain females (Janvier labs) were housed in a 12 hours light/12 hours dark cycle with free access to food, and animal procedures were carried out in accordance with institutional guidelines. Animal protocols were approved by the Charles Darwin animal experimentation ethical board (CEEACD/No 5). The date of the vaginal plug was recorded as embryonic day (E) 0.5 and the date of birth as postnatal day (P) 0.

Chicken embryos. JA57 chicken fertilized eggs were provided by EARL Morizeau (8 rue du Moulin, 28190 Dangers, France) and incubated at 38° C. for the appropriate time in a FIEM incubator (Italy).

DNA constructs. The plasmid vector based on the PB-ID switch is indifferently entitled PB-ID vector or ion vector. The plasmid vector based on the PB-zID switch is indifferently entitled PB-zID vector or zion vector.

A schematized map of the plasmids designed for this study can be found in FIGS. 13A to 16B2. Transgene assembly was based on a combination of DNA synthesis (Genscript Inc), Gibson assembly (NEB) and standard restriction and ligation-based cloning. PCR for Gibson assembly was performed using CloneAmp HiFi PCR Premix (Clontech) and Q5 high-fidelity DNA polymerase (NEB). All iOn and control piggyBac vectors were assembled in the 1835 bp-long pUC57-mini plasmid backbone (Genscript Inc) using minimal piggyBac 5' and 3' TRs (Meir et al. (2011), Li et al. (2005), with an additional 3 bp from the wild type transposon (ref) in the 3'TR. GOIs and promoters can be inserted with the restriction sites. The strong eukaryotic CAG (Niwa et al. (1991) and CMV promoters as well as a 2145 bp fragment regulating expression of the human Atoh7 gene (Chiodini et al. (2013) were used. GOIs were followed by a bovine growth hormone transcriptional terminator (Kakoki et al. (2004) (pA1). In the final iOn vector design, a Rabbit beta-globin terminator (pA2) terminator was added upstream of the PB 3'ITR to prevent cryptic episomal transcription. FPs used as GOI included RFP (mRFP1, Campbell et al. (2002), GFP (EGFP, Clontech) and IRFP (IRFP670, Shcherbakova et al. (2013). In ziOn vectors, the ORF of these FPs was split near the N terminus (Nt) in two opposite-oriented fragments that become reunited by transposition with incorporation of the TTAA footprint. In the PB-zIDCMV∞Cre vector, the Cre recombinase ORF was separated in Nt and Ct portions as in Jullien (2003), with incorporation of the TTAA footprint at a silent position (Leu104). To limit expression of the Cre Nt fragment prior to transposition, its coding sequence was positioned in frame (through the PB 5'TR) with a PEST degron (Li et al. (1998) followed by a translational stop. The membrane-restricted GFP was generated by adding a short Kras tethering sequence (Averaimo et al. (2016) at the Ct end of EGFP using annealed oligonucleotides. To assay Cre activity, we designed a floxed reporter (Tol2-CAG::loxP-mCherry-loxP-EYFP, abbreviated as Tol2-CAG::RY) in which expression switches from mCherry (Shaner et al. (2004) to EYFP (Zacharias (2002) upon recombination. This transgene was framed with Tol2 transposition endfeet (Sato et al. (2007) to enable genomic integration. The PB-zIDCAG∞RFP-2A-NICD vector was assembled by introducing a 2A cleavage sequence (Kim et al. (2011) between the RFP and NICD ORFs to enable their corexpression. As non-integrative control, we used a CAG::NICD-2A-GFP plasmid (Rios et al. (2011). Other plasmids used in this study included CMV-driven vectors expressing Cre, mTurquoise2 (Goedhart et al. (2012) and IRFP670 (Shcherbakova et al. (2013) as well as CAG-driven vectors producing EGFP, mCerulean (Rizzo et al. (2004), the Tol2 transposase (Kawakami, K. & Noda, T. (2004) and an optimized piggyBac transposase (hyPBase Loulier et al. (2014). The maps of the classic transposon, PB-CAG::RFP, of the vector based on the PB-ID switch, PB-IDCAG∞RFP and of the vector based on the PB-zID switch, PB-zIDCAG∞RFP are respectively presented in FIGS. 14A to 16B2. The sequences of these three vectors are respectively SEQ ID NO: 13, SEQ ID NO: 14 and SEQ ID NO: 16. Other detailed maps and sequences are available upon request.

Cell culture experiments. iOn and piggyBac plasmids were transfected in HEK293, HeLa or mouse NIH 3T3 cells using cationic lipids. All FIGURES show replicates of at least 3 experiments. Except when otherwise noted, $1×10^5$ cells/well were plated in a 24-well dish and transfected at 1 DIV with 100 ng iOn vector with or without 20 ng of PBase-expressing plasmid (CAG::hyPBase) using 0.7 µL of Lipofectamin 2000 (Invitrogen). For triple-color labeling experiments, we used 100 ng/well of each PB-zIDCAG∞FP plasmid and 60 ng of PBase vector. To validate the PB-zIDCMV∞Cre transgene, 50 ng of the corresponding plasmid was co-transfected with 10 ng of PBase vector in a HEK293 cell line stably expressing the Tol2-CAG::RY reporter construct. This line was established by successive use of Tol2 transposition, drug selection with G418 (300 µg/mL) and picking of RFP-positive clones. In some experiments, 50 ng of non-integrative plasmid expressing an FP marker distinct from the iOn vector (CMV::mTurquoise2, CMV::IRFP or CAG::GFP) were applied as transfection control. For FACS analysis, transfections were performed in 6 cm dishes with scaled up concentrations. HEK293 cell viability after iOn plasmids transfection was assessed by dye exclusion with 0.4% Trypan blue solution (Sigma). After 2-3 DIV, FP expression was either assayed by flow cytometry on live cells or by imaging of fixed cells with epifluorescence or confocal microscopy or an Arrayscan high-content system (Thermo Fisher Scientific) (see below). For fixed observations, cells grown on 13 mm coverslips were immersed in 4% Paraformaldehyde (PFA) in phosphate buffer saline (PBS) (Microm Microtech), rinsed in PBS and mounted in Vectashield mounting medium supplemented with DAPI (Vector labs).

FACS analysis and stable cell line establishment. For FACS analysis, HEK293 cells grown on 6-cm dishes were dissociated three days after transfection, stained with DAPI and analyzed on a MoFlo Astrios cell sorter (Beckman Coulter) using the following laser lines: 405 nm (DAPI), 488 nm (GFP), 561 nm (RFP), 640 nm (IRFP). 10000 cells were analyzed for each condition; non-fluorescent controls were prepared from mock-transfected cells stained with DAPI. For single-cell sorting, HEK293 cells were sorted as single cells two days after transfection. Selection windows were chosen to select most of the FP-positive population and exclude negative cells. For 3-color cell sorting, we first selected live dissociated cells and subsequently selected RFP+, IRFP+ cells within the GFP+ population. The cells were plated as single cells into 96 well plates and grown during 7-10 days in 10% FBS/DMEM medium. FP expression was assayed by epifluorescence microscopy or Arrayscan High-Content system (see below). Some positive clones were expanded in larger dishes for sequencing. To this aim, genomic DNA was isolated from a confluent 3.5 or 10 cm dish with the Nucleospin Tissue Kit (Macherey-nagel). The rearranged region between the promoter and GOIs (500-600 bp) was amplified using CloneAmp HiFi PCR premix (Clontech) and directly assessed by Sanger sequencing (Genewiz, UK).

Human iPS cell transfection and differentiation. For PB-ID labeling of differentiating iPS cells, colonies were dissociated with Accutase (Life Technologies) and replated in 96-well plates coated with poly-L-ornithine (20 µg/ml, Sigma P4957) and laminin (3 µg/ml, Sigma 23017-015). On day 2, cells were transfected with Dreamfect (OZBioscience) according to the manufacturer's instructions. Cells were then differentiated as spinal motor neurons, fixed on day 14 with 4% PFA and stained with Tuj1 antibody as previously done (Maury et al., 2015). For iPS line generation, WTSIi008-A iPS cells were plated and transfected with Lipofectamine Stem Cell reagent (Invitrogen) according to the manufacturer's protocol. Transfected cells were isolated by manual or EDTA passages, and homogeneous colonies were obtained 18 days after transfection (4 passages).

Mouse ES cell transfection and clone selection. KH2 ES cells were transfected with PB-zIDCAG∞GFP-Kras and CAG::hyPBase (a plasmid expressing an optimized piggyBac transposase (hyPBase, Yusa et al., 2011)) plasmids (4 to 1 weight ratio) using Lipofectamine 2000 reagent. 48 hours after transfection, GFP-positives cells (1.5%) were sorted using an Astrios MoFlo EQ cell sorter and plated at low density (103 cells/10-cm dish) on feeder cells. After eight days, GFP-positives clones were picked under a fluorescent stereomicroscope (Zeiss Discovery V20).

Embryonic electroporation. In utero and in ovo electroporation in mouse and chicken embryos were performed as previously described (Loulier et al. (2014). Mice were housed in a 14 hr light/10 hr dark cycle with free access to food, and animal procedures were carried out in accordance with institutional guidelines. A DNA mix containing 1 µg/µl of each iOn plasmid mixed 5:1 with the PBase vector was injected with a glass capillary pipette into the lateral ventricle of E12 mouse embryo, the central canal of E2 chick embryo spinal cord or the optic cup of E.15 chick embryos. Embryos were left to develop until sacrifice. Tissues were fixed in 4% PFA. 14 µm sections of E14 embryonic mouse brains were obtained with a cryostat. Postnatal mouse brain and E8 chick spinal cords were sectioned at 200-400 µm thickness with a vibrating-blade microtome (VT1000, Leica). Chick E6 spinal cords and E14 retina were flat-mounted on glass slides. All Samples were mounted in Vectashield mounting medium.

Immunostaining. For cell cultures: cells were plated on 13 mm glass coverslips coated with collagen (50 µg/mL, Sigma). Fixation with 4% Paraformaldehyde (PFA) in PBS (Microm Microtech) was followed by blocking in PBS containing 10% normal goat serum (Sigma) and 0.5% Triton X-100 (Sigma) for 1 hr at room temperature. Cells were then incubated with rabbit anti-FLAG primary antibody (1:250, Sigma) overnight at 4° C. in the blocking solution. After washing in PBS and incubation with secondary antibodies (1:500, Alexa 647 anti-goat IgG, Invitrogen) for 1 hr at room temperature, cells were washed again in PBS prior to mounting in Vectashield medium. For chicken spinal cords sections: chick embryos were fixed for 1 hr in ice-cold 4% PFA and rinsed 3 times in PBS. The embryos were then equilibrated in 30% sucrose and embedded in TissueTek (Sakura), frozen on dry ice and stored at −80° C. prior to cryostat sectioning (Microm HM560, 14 µm sections). After equilibration at room temperature, sections were washed in PBS before a blocking step in PBS-0.1% Triton-10% normal donkey serum (NDS) and overnight incubation with primary antibodies (anti-HuC/D, Molecular Probes), diluted 1:50 in PBS-0.1% Triton-1% NDS. The following day, slides were washed 3 times in PBS, incubated 1 hr with the secondary antibody (Alexa647 donkey anti-mouse, Invitrogen, 1:500) in the above buffer, washed again 3 times and mounted with Vectashield mounting medium.

Fluorescence imaging and image analysis. Epifluorescence images were collected with a 10×0.6 NA or 20×0.7 NA objective on a Leica DM6000 microscope equipped with a VT1000 camera and separate filter cubes for GFP, RFP and IRFP. Confocal image stacks were acquired with 20×0.8 NA Oil and 40×1.3 NA Silicone objectives on an Olympus FV1000 microscope, with 488, 560, and 633 nm laser lines to excite GFP, RFP and IRFP/Alexa647, respectively. Image analysis was performed with Fiji (Schindelin et al. (2012) and Imaris. Levels were uniformly adjusted across images with Adobe Photoshop. For analysis with Arrayscan (Thermo Fisher Scientific), cells grown in a 24 well plate were fixed 15 min with 4% PFA and stained with 300 nM DAPI prior imaging with the following laser lines: 386 nm (DAPI), 485 nm (GFP), 570 nm (RFP), and 650 nm (IRFP). For time-lapse imaging, we used an inverted wide field microscope (Nikon Ti Eclipse) operated by Micromanager software equipped with a sCMOS Camera (Orca Flash4LT, Hamamatsu) and a 10× objective (CFI Plan APO LBDA, NA 0.45, Nikon). The cells growing in glass-bottom 35 mm dish (Matek) were incubated in a microscope chamber at 37° C., under 5% CO2 in a humidified atmosphere. Image analysis was performed with Fiji.

Statistical Analysis

The number of samples analyzed is indicated in the figure legends. Statistical analyses were performed using R or GraphPad Prism software. Significance was assessed using Student t, $\chi^2$ and Kruskal-Wallis (one-way ANOVA on ranks) tests, and non-parametric Mann-Whitney U test. Data represent mean+SEM, ns, $p>0.05$; * $p<0.05$;  $p<0.01$, * $p<0.001$.

FACS analysis. 10 000 cells were analyzed for each condition; non-fluorescent controls were prepared from mock-transfected cells stained with DAPI.

B. Results and Discussion
Transposition-Dependent Expression Switch Based on the piggyBac Transposition System (PB-ID Switch)
1) The PB-ID Switch Core Features (FIGS. 1A-1D)

Figure 1A:
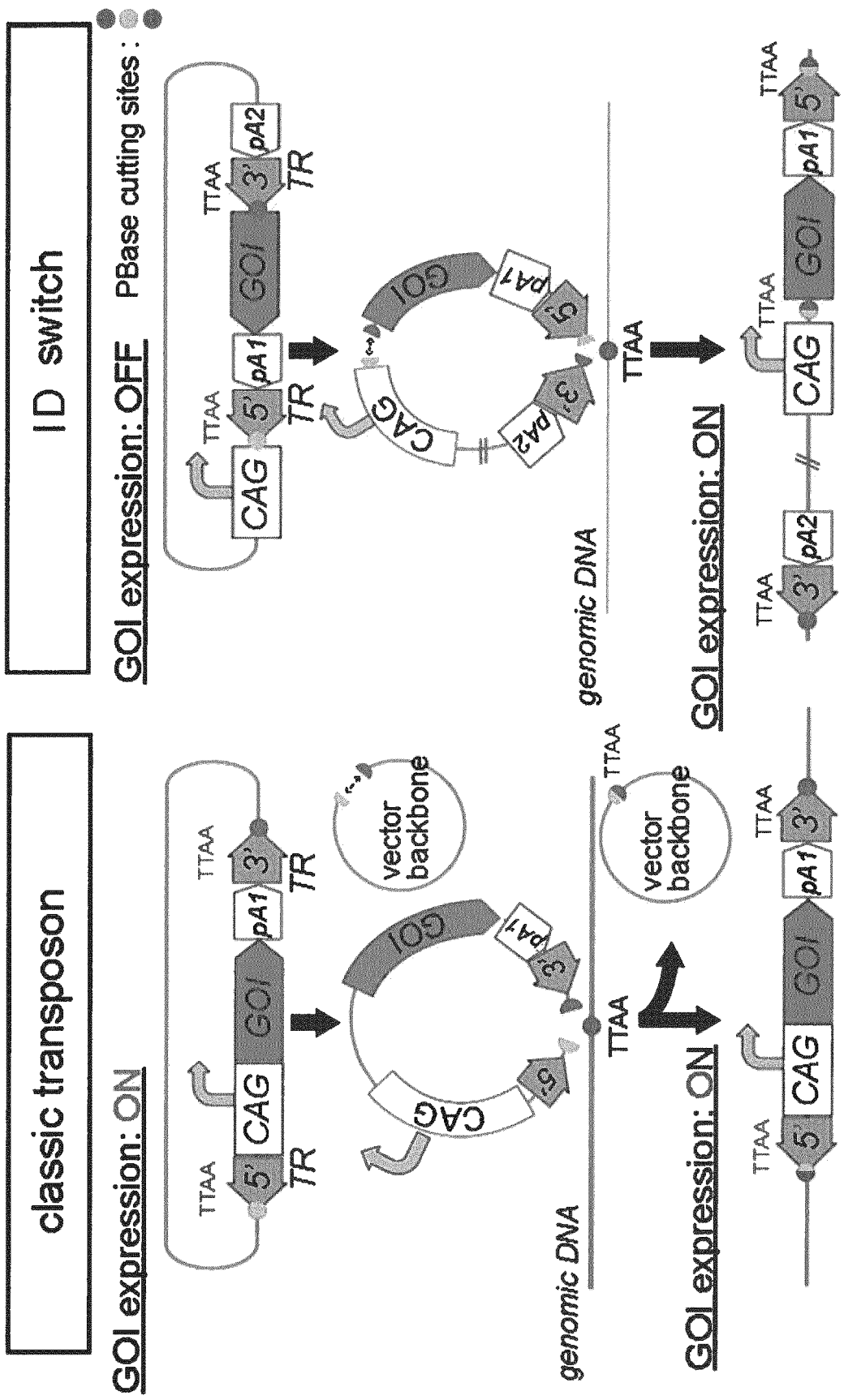
Figure 1B:
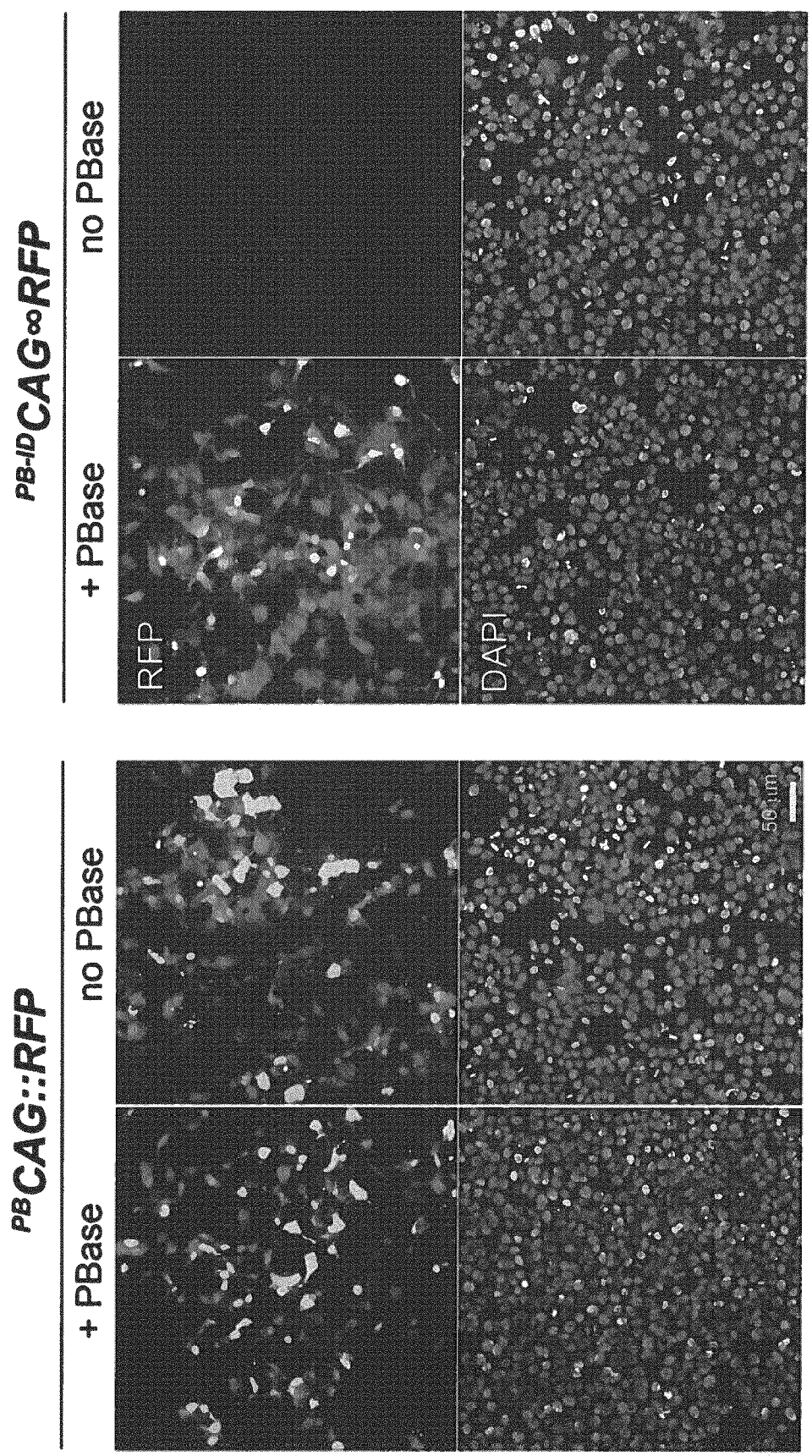

Transposon systems functioning according to a "cut-and-paste" mechanism (e.g. piggyBac, Tol2 and Sleeping Beauty; Wu et al., 2006) are widely used to achieve genome integration in random loci. To build an integration-driven (ID) genetic switch, the piggyBac transposition system was used, for its known efficiency, large cargo capacity and precise cut-and-paste mechanism (Lacoste et al., 2009; Woodard and Wilson, 2015; Wu et al., 2006). The piggyBac transposase (hereafter designed PBase) mobilizes elements flanked by two terminal repeats of the piggyBac transposon (Lacoste et al., 2009, hereafter designed 5'TR and 3'TR), and inserts these elements in the genome of targeted cells at TTAA sites. Upon transposon excision, these TTAA sites are precisely restored. In classic plasmid vectors based on the piggyBac system (FIG. 1A, left), a transgene composed of a promoter (i.e. sequence driving transcription initiation) and a gene of interest (GOI) usually followed by a transcription terminator is positioned between the two piggyBac TRs, such that the transposase first excises it from the backbone vector and subsequently inserts it in the genome of host cells. The transgene is thus expressed prior to PBase-mediated excision from the donor plasmid (FIG. 1B, left). By contrast, the PB-ID vectors harbors an arrangement of the promoter, GOI and TRs that maintain the transgene silent in the episomal form (FIGURE TA, right): first, one of the two piggyBac ITR is placed in reverse orientation (5'ITR in sense orientation and 3'ITR in anti-sense orientation) in the donor plasmid compared to the classic transposon configuration (5'ITR and 3'ITR both in sense orientation), such that the two ITRs are in parallel rather than antiparallel orientation. Second, the transgene is split in two elements unable to produce a fully functional product, which are separated by one of the TRs and are positioned in opposite orientation relative to each other. The GOI is therefore not expressed prior integration (FIG. 1B, right), or only its 5' portion. This configuration creates a situation in which both piggyBac-mediated insertion and excision concur to integrate the donor plasmid in the host genome, while at the same time causing a rearrangement that reunites the two parts of the transgene into a functional expression unit, thus triggering GOI expression. Unlike with classic piggyBac vectors, the whole vector integrates in the genome of host cells. This transgene configuration is hereafter termed PB-ID, and transgenes based on this principle that express a gene of interest (GOI) from a promoter (Prom) are denoted in the following way: PB-IDProm∞GOI, with the infinity symbol ∞ representing the rearrangement that takes place during transposition, by opposition to a classic transposon configuration where the GOI is constitutively under the control of the promoter (denoted hereafter: PBProm::GOI). Based on the PB-ID principle, several types of vectors were designed and validated, presented below.

Figure 2A:
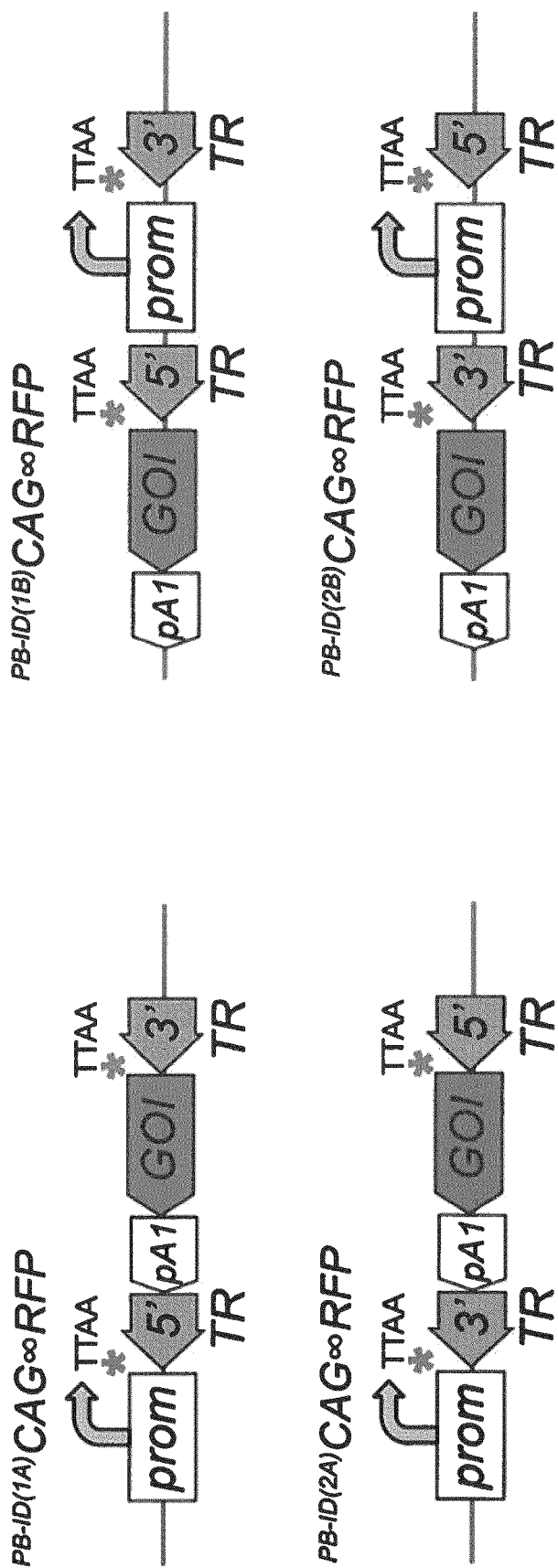

2) Validation and Iteration of the PB-ID Switch
2.1) PB-ID Vectors in which Transcription of a GOI, Initially Blocked, is Activated by Genome Integration Mediated by the piggyBac Transposase (PB-ID Transcriptional Switch, FIGS. 1A-1D and FIGS. 2A-2B2)
a) Principle:

In the PB-ID transcriptional switch, a promoter and a GOI are positioned in head-to-head (inverted) orientation in episomal vectors and separated by one of the piggyBac ITR, thus preventing transcription. Upon genomic integration by PBase action, as explained above, rearrangement of the PB-ID vector brings the GOI under the control of the promoter and in correct orientation, thus triggering its transcription (FIGURE TA right). This situation contrasts with the design of a classic piggyBac transposon vector in which the GOI is already under the control of the promoter before its integration (FIGURE TA, left).

b) Design of Different PB-ID Transcriptional Switch Configurations (FIGS. 2A-2B2):

Distinct configurations of PB-ID transcriptional switch may be used to trigger expression of a GOI by piggyBac transposition, depending on the relative arrangement of the promoter, GOI, terminal repeats and vector backbone (FIG. 2A). In particular we conceived different types of PB-ID configurations depending on the following two aspects:

i) Relative arrangement of the promoter, GOI, and vector backbone. Two PB-ID configurations which we respectively term type A and type B can be defined depending on the position of the vector backbone, adjacent to the 5' end of the promoter (such that the promoter and GOI are separated by the backbone sequence on their 5' end), or to the 3' end of the GOI (such that the promoter and GOI are separated by the backbone sequence on their 3' end);
  ii) Position of the 5' and 3' piggyBac ITRs relative to the other elements of the transgene. two PB-ID configurations can be defined, type 1 and type 2, depending on whether the 5' or 3' piggyBac ITR is positioned between the promoter and the GOI.

Combinations of these arrangements define four configurations of PB-ID switches which are denoted PB-ID(1A), PB-ID(1B), PB-ID(2A) and PB-ID(2B) (FIG. 2A).

c) Validation In Vitro:

To test whether the different types of PB-ID configurations defined above could drive transposition-dependent GOI expression, PB-ID vectors were assembled in a pUC57-mini plasmid backbone using minimal piggyBac 5' and 3' TRs (Lacoste et al., 2009), the broadly active synthetic CAG promoter (composed of a CMV enhancer, chicken beta-actin promoter and rabbit beta-globin splice acceptor, Niwa et al., 1991), and RFP as a GOI (mRFP1, Campbell et al., 2002), followed by a bovine growth hormone transcription terminator (bGH polyA, Kakoki et al., 2004). Three PB-IDCAG∞RFP vectors were constructed following the PB-ID(1A), PB-ID(1B) and PB-ID(2A) design, hereafter denoted PB-ID(1A)CAG∞RFP, PB-ID(1B)CAG∞RFP and PB-ID(2A)CAG∞RFP, which enabled us to test type A vs. type B as well as type1 vs. type 2 arrangements.

The three PB-IDCAG∞RFP plasmids were transfected in HEK-293 cells using cationic lipids (Lipofectamin 2000, Invitrogen), along with or without a second plasmid expressing an optimized piggyBac transposase (hyPBase, Yusa et al., 2011, abbreviated below as PBase) under a CAG promoter (Niwa et al., 1991). After 3 days in culture, strong expression of RFP in PBase-transfected cells, but not in absence of transposase, indicated that all three PB-IB transgene configurations drove PBase-dependent GOI expression (FIG. 2B). The type A configuration was found to have less background expression of the GOI in absence of PBase compared to the type B configuration. This may be due to reverse promoter activity of the CMV enhancer (Keil et al., 1987) in this second configuration. The PB-ID(1A) configuration which showed high signal with PBase and low background expression of the GOI in absence of PBase was chosen for subsequent experiments. To further suppress residual background transcriptional activity from the backbone vector, an additional transcription terminator (Rabbit beta-globin polyadenylation sequence) was positioned 5' of the GOI in the PB-ID(1A)CAG∞RFP vector, immediately after the 3'TR (FIG. 1A right). This PB-ID design denoted PB-IDCAG∞RFP for the sake of simplicity, was used in all ensuing experiment. Comparison of the PB-IDCAG∞RFP vector with a classic transposon (PBCAG::RFP) showed that it achieved efficient PBase-dependent RFP expression with low transcriptional leakiness in absence of transposase, while the classic transposon vector readily expressed RFP in episomal form (FIG. 1B).

Time-course experiments comparing the PB-IDCAG∞RFP vector with classic non-integrative episomal (CAG::RFP) and piggyBac-based (PBCAG::RFP) vectors showed that the PB-ID strategy suppresses the burst of expression associated with classic episomal plasmids prior to their dilution by cell division (FIG. 1C). Expression levels with PB-ID were also found to be less variable among individual cells and to stabilize more rapidly than with vectors active in the episomal form (FIG. 1C).

d) Validation In Vivo in Chicken:

The PB-IDCAG∞RFP plasmid was electroporated in ovo in the embryonic chicken spinal cord with or without a second plasmid expressing PBase (FIG. 1D). Four days after transfection, RFP expression was observed in a PBase-dependent manner in cells running from the VZ to the outer layers of the neural tube. This expression pattern is indicative of transgene integration in the genome of electroporated neural progenitors lining the ventricular surface, thus achieving long-term labeling of these cells and their neuronal progeny, known to form radial clonal patterns (Leber and Sanes, 1995; Loulier et al., 2014). By contrast, expression from a non-integrative vector (CAG::Cerulean) was mostly restricted to isolated neurons born shortly after the electroporation (FIG. 1D).

e) Validation In Vivo in Mice:

The classic episomal vector (CAG::GFP) was electroporated in utero at E12, in the mouse cerebral cortex and GFP expression was observed in neurons born shortly after the electroporation, then, in intermediate layers, due to its rapid dilution in dividing progenitors. In contrast, with a PB-IDCAG∞RFP which was electroporated in the same way, RFP expression was observed in progenitors and all their radially-migrating derivatives, including late born upper-layer neurons and astrocytes, and in a strict PBase-dependent manner. Similarly, in the mouse retina, the PB-ID vector was electroporated at the start of neurogenesis and RFP was observed in all retinal layers, while episomes only marked early born retinal ganglion cells. Importantly, it avoided the strong and irregular labeling of isolated neurons obtained with classic transposons and episomes, likely due to inheritance of multiple non-integrated copies.

Figure 3A:
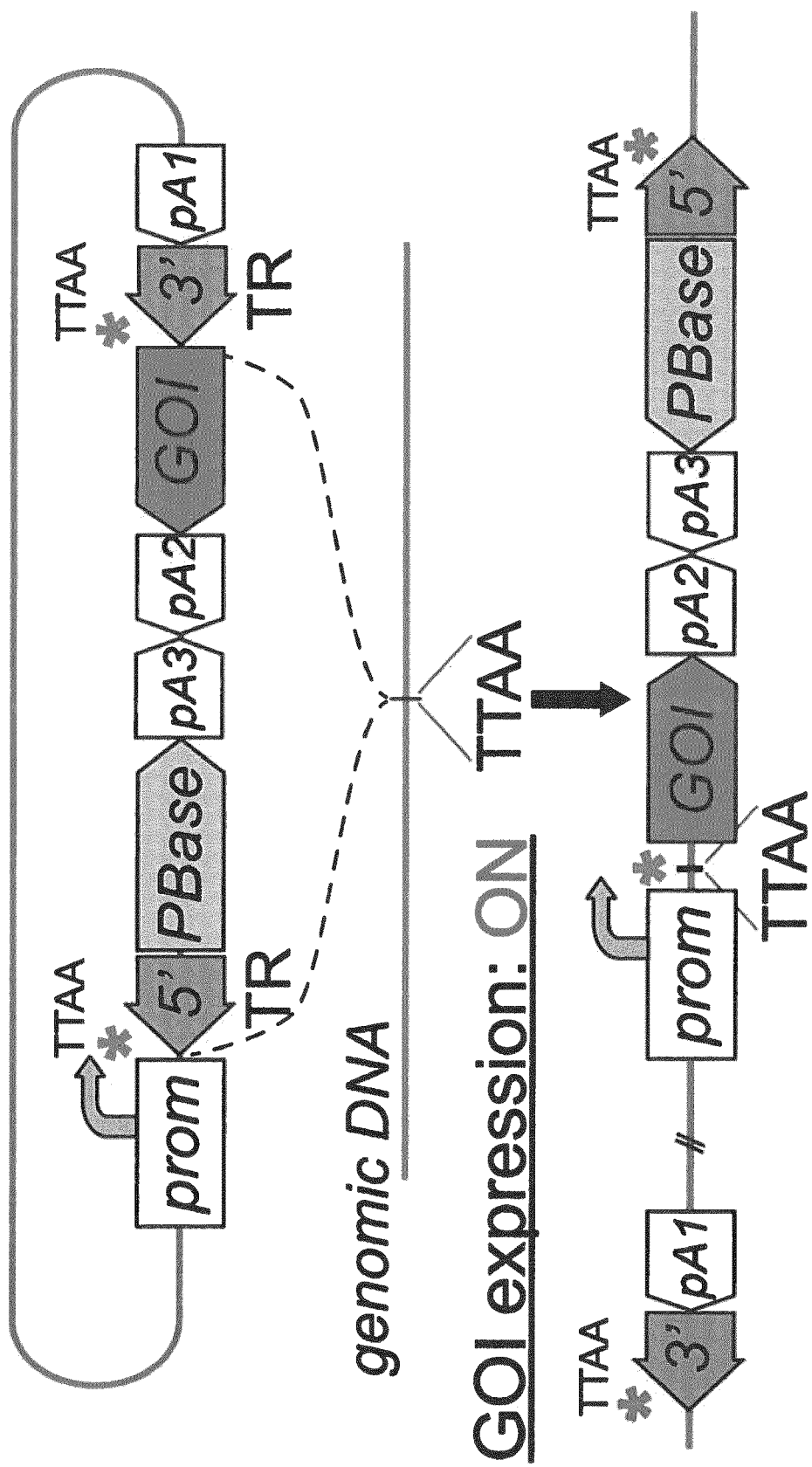
FIGS. 3A-3B: All-in-one PB-ID vector expressing PBase by default and switching to that of the GOI upon genome integration
Figure 3B:
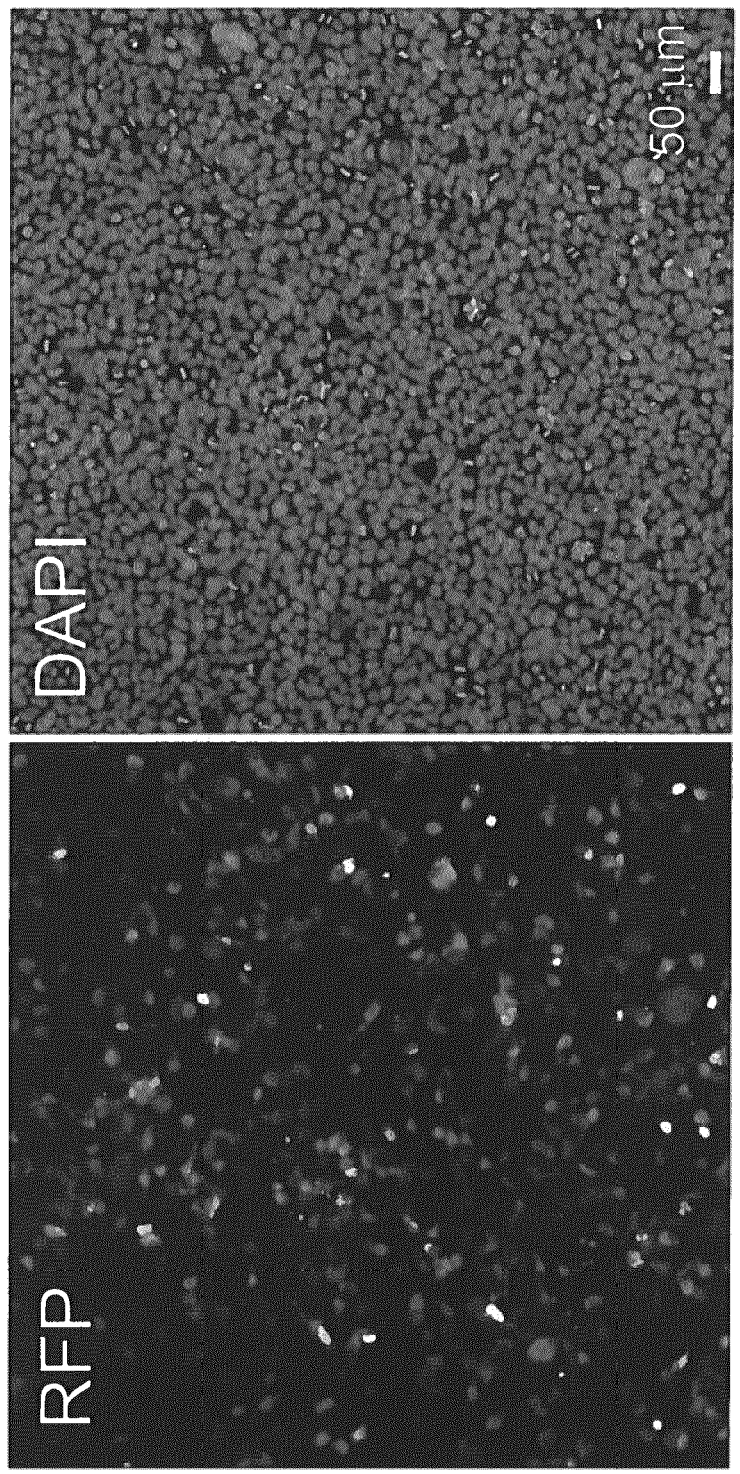

2.2) "All-In-One" PB-ID Vector in which the piggyBac Transposase is Initially Expressed by Episomal ID Vectors, and where Expression Switches to that of a GOI Upon Transposition (Auto-PB-ID Switch, FIGS. 3A-3B)

a) Principe:

In the auto-PB-ID switch all components of the ID switch are encoded by a single "All-in-one" vector (FIGS. 3A-3B). The design follows that of the transcriptional ID switch (I.2.1) with the following modification: a piggyBac transposase gene (Yusa et al., 2011) is placed under the control of the promoter such that it is expressed in the episomal form of the vector. Upon genomic integration and rearrangement triggered by PBase action, the GOI is repositioned downstream of the promoter, thus triggering its transcription, while the PBase gene ends in opposite orientation relative to the promoter and is therefore no more under its control. Expression thus switches from PBase to that of the GOI (FIG. 3A). This enables to achieve transposition-dependent GOI expression with a single vector. We hereafter denote this configuration: PB-IDProm::PBase∞GOI.

b) Validation:

An auto-PB-ID vector was assembled by placing a piggyBac transposase gene (hyPBase; Yusa et al., 2011) followed by a transcriptional terminator in the PB-ID vector described in 1.2.1 immediately after the 5' TR that follows the promoter. In this configuration termed PB-IDCAG::PBase∞RFP, expression switches from PBase to RFP expression upon transposase-mediated genome integration (FIG. 3A). Tests in transfected HEK-293 cells indicate that as expected, the PB-IDCAG::PBase∞RFP vector drives GOI expression in absence of other helper vectors (FIG. 3B).

Figure 4A:
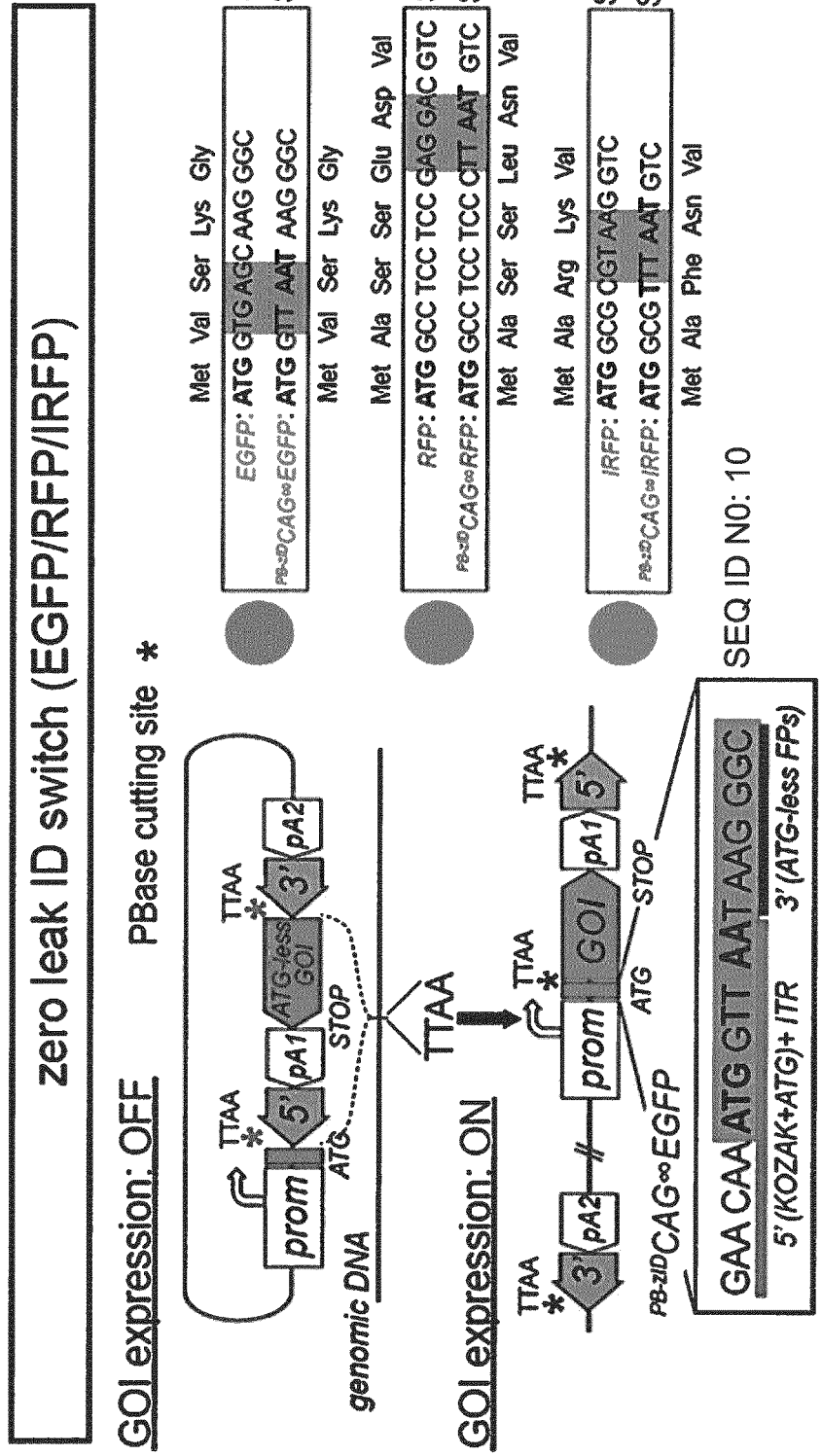
Figure 5A:
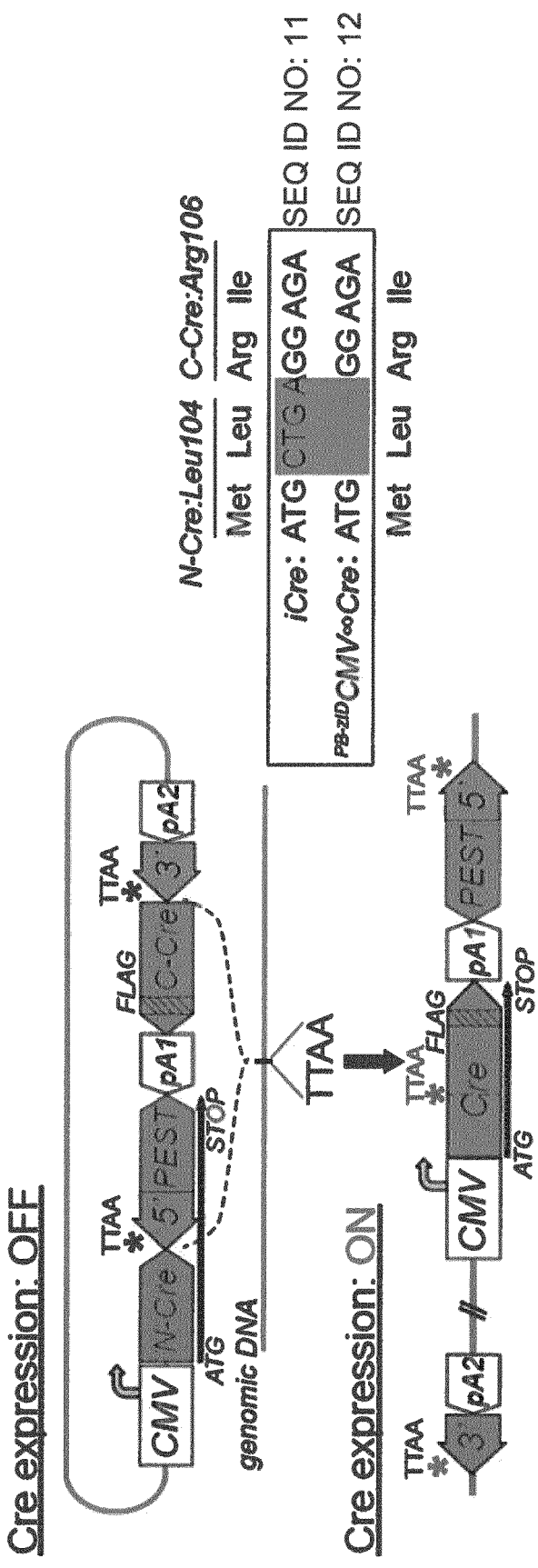

2.3) PB-ID Vectors in which Full Translation of a GOI, Initially Blocked, is Activated by Genome Integration Mediated by the piggyBac Transposase (PB-ID Translational Switch, FIGS. 4A-4B2 and FIGS. 5A-4B2)

a) Principe:

In the PB-ID transcriptional switch (I.2.1), any leaky transcription from the episomal vector, if it occurs, shall be followed by translation of the GOI and production of the corresponding protein. To avoid such possibility, we designed a PB-ID translational switch, in which both transcription and translation of the GOI are blocked in the episomal form of the vector (FIGS. 4A-4B2). In this switch, the GOI open reading frame (ORF) is split in two parts: a 5' part containing at least the translation initiation codon and a variable number of amino acids encoding a non-functional N-terminal portion of the protein, and a 3' part encoding the rest of the protein until the STOP codon (FIG. 4A). The promoter associated with the 5' part of a GOI is positioned in head-to-head (inverted) orientation relative to the 3' part of the GOI and these two elements of the transgene are separated by one of the piggyBac TR. Upon genomic integration driven by PBase action, rearrangement of the PB-ID vector reunites the two parts of the GOI into a functional ORF positioned under the control of the promoter, thus enabling completion of GOI transcription and translation. Minor modifications of the GOI sequence are made to incorporate the piggyBac footprint (TTAA sequence resulting from the reunion of the two parts of the GOI upon integration) in the ORF without altering the reading frame and with minimal changes of the sequence of the resulting protein. We denote such configuration PB-zIDProm∞GOI.

b) Validation:

Four different vectors were designed to express the following GOIs based on the PB-ID translational switch (FIGS. 4A-4B2 and 5A-4B2): EGFP (green fluorescent protein), mRFP1 (red fluorescent protein; Campbell et al., 2002), IRFP670 (near-infrared fluorescent protein; Shcherbakova and Verkhusha, 2013) and the site-specific recombinase Cre. The GOI ORF was split in 5' and 3' parts in the following way: in the first three vectors, PB-zIDCAG∞EGFP, PB-zIDCAG∞RFP, and PB-zIDCAG∞IRFP expressing fluorescent proteins from a CAG promoter, the 5' part of the GOI encodes the first 3-6 amino acids of the proteins (FIG. 4A). In the fourth vector encoding the site-specific Cre recombinase from a CMV promoter (PB-zIDCMV∞Cre), the Cre ORF is split in two 5' and 3' parts known to be separately inactive (Jullien, 2003) (FIG. 5A). Furthermore, the following modification is made to destabilize the Nt portion of Cre (NtCre) expressed prior integration by the episomal vector: the corresponding 5' portion of Cre coding sequence is followed by the downstream piggyBac 5'TR, a PEST sequence for rapid degradation (Rogers et al., 1986) and a transcription terminator arranged in such way that the resulting fusion product (NtCre-5'TR-PEST) can be transcribed and translated.

Tests in HEK-293 cells with the four vectors described above indicate that PB-ID translational switch enables PBase-dependent expression of GOIs (FIGS. 4B and 5B). The PB-zIDCAG∞RFP showed reduced leakiness in absence of piggyBac transposase, compared to the PB-IDCAG∞RFP vector based on the PB-ID transcriptional switch (FIG. 4C). The PB-zIDCMV∞Cre vector was transfected in HEK-293 cells stably expressing a "floxed" reporter transgene that switches color upon Cre recombination (CAG-loxP-RFP-loxP-YFP). Cre expression, revealed by color change of the floxed reporter transgene or by immunostaining against Cre, occurred only in cells co-transfected with PBase (FIG. 5B).

2.4) PB-ID Vectors Encoding Different Colors of Fluorescent Proteins Enabling to Identify Co-Transfected Cells
  a) Principe: Co-transfection of individual cells with different transgenes can be assessed using vectors expressing different reporter genes. To this aim, we designed the three vectors mentioned above based on the PB-ID translational switch (1.2.3) expressing the fluorescent proteins EGFP (green, PB-zIDCAG∞EGFP), mRFP1 (red, PB-zIDCAG∞RFP) and IRFP670 (near-infrared, PB-zIDCAG∞IRFP) from the broadly active CAG promoter (FIG. 4A).
  b) Validation: The three vectors were validated by transfection in HEK-293 cells (see 1.2.3, (FIG. 4B). Co-expression of distinct fluorescent proteins was frequently observed, indicating integration of multiple distinct transgene copies in individual cells. See below application of these transgenes for rapid cell-line establishment (1.3.2) and cell lineage tracing (1.3.4).

Figure 6:
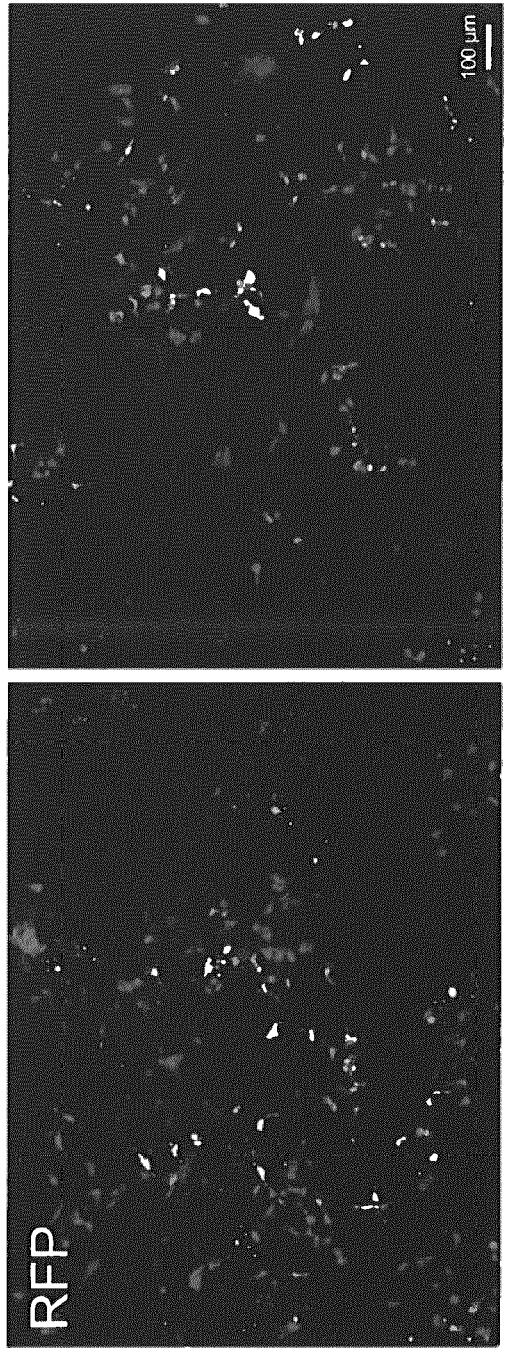
FIG. 6: PB-ID vector modified to prevent suicidal auto-integration

2.5) Vectors in which Sequence Modifications Prevent PBase-Mediated Integration of One
Copy of the Vector into Another Copy (Auto- and Inter Episomal Integration)(FIG. 6)
a) Principe:
  In vectors based on the piggyBac system, such as classic piggyBac transposons and PB-ID vectors, action of the transposase may lead to unwanted auto- or inter-integration in the episomal form of the piggyBac-based vector itself (Wang et al., 2014), or in the vector encoding the piggyBac transposase. To reduce as much as possible the possibility of such inter-episomal (also called "suicidal") integration and favor genomic integration, we designed and assembled a vector backbone based on the pUC57-mini plasmid and containing a CAG promoter and RFP reporter transgene in which we eliminated all TTAA sites by single-base pair substitutions. Substitutions were done in ways that do not affect the replication of the vector in bacteria, nor its function in eukaryotic cells. Based on this design, we assembled two vectors:
  An ID vector based on the PB-ID translational switch that contains no TTAA sequences except for the two sites at the extremities of the PB 5' and 3'TRs that are required for transposon excision. These TTAA sequences have been shown to only rarely lead to auto-integration (Wang et al., 2014). This mutated vector expressing RFP from a CAG promoter upon genomic integration is hereafter termed PB*-zIDCAG∞RFP, using an asterisk to denote the mutation of TTAA sites.
  A vector expressing the hyperactive transposase hyPBase from a CAG promoter which is entirely devoid of TTAA sequences, hereafter termed *CAG::PBase.

b) Validation In Vitro and In Vivo:
  The TTAA-less PB*-zIDCAG∞RFP and *CAG::PBase vectors were transformed in E. coli competent cells were they replicated normally. They were then tested in vitro in HEK-293 cells, and in vivo by in ovo electroporation in the embryonic chicken spinal cord (FIG. 6). In both cases, expression of the GOI (RFP) in a PBase-dependent manner was observed.

2.6) A PB-ID Vectors in which Expression of a GOI is Co-Expressed Along with a Marker Gene for the Purpose of Identifying Genetically Modified Cells (FIGS. 7A1-7B)
  a) Principe: Expression of a marker gene along with a GOI with the PB-ID system is useful to identify cells that express the GOI for varied purposes, such as selecting stably transfected cell lines or assaying the effects of GOI expression in vitro or in vivo.
  b) Validation: We designed and assembled a vector based on the PB-ID translational switch enabling PBase-dependent co-expression of a fluorescent marker (RFP) along with a gene of interest (NICD, the Notch receptor intracellular domain; Pierfelice et al., 2011) using a 2A peptide (enabling translation of two successive ORFs from a single mRNA). This vector (PB-zIDCAG∞RFP-2A-NICD) was tested in vivo by electroporation in the embryonic chicken spinal cord along with PBase (FIGS. 7A1-7B). After 3 or 6 days of incubation, analysis of labeled cells shows the effects expected for long-term expression of NICD: marked reduction of neurogenesis from perturbed neural progenitors expressing RFP, and expansion of these progenitor cells at the ventricular surface compared with a control condition (corresponding to electroporation of zPB-IDCAG∞EGFP).

2.7) A PB-ID Vectors in which Expression of a GOI is Controlled by Regulatory Sequences of Interest (FIGS. 8A-8B)
  a) Principe: Achieving expression of GOIs from regulatory sequences of interest (e.g. promoter or enhancers) in genome-integrated configuration is useful for varied purposes such as assaying different regulatory sequences, testing their resilience to epigenetic effects, or controlling GOI expression in a cell type or stage-specific manner.
  b) Validation: We designed and assembled vectors based on the PB-ID translational switch enabling transposition-dependent expression of a fluorescent marker (RFP) or Cre recombinase from regulatory sequences of the human Atoh7 gene (Skowronska-Krawczyk et al., 2009). In vertebrates, Atoh7 is expressed in subsets of retinal neurons: retinal ganglion cells but not bipolar and amacrine cells (Chiodini et al., 2013). The two vectors (PB-zIDAtoh7∞RFP and PB-zIDAtoh7∞Cre) were tested in vivo by electroporation in the embryonic chicken retina along with PBase (FIGS. 8A-8B). To report Cre expression, the PB-zIDAtoh7∞Cre transgene was co-transfected with a genome-integrative "floxed" Brainbow reporter transgene that switches fluorescent protein expression in a Cre-dependent manner (Loulier et al., 2014). After 5 days of incubation, analysis of labeling patterns showed that expression from the PB-zIDAtoh7-driven transgenes was restricted to the expected retinal subtypes.

3) Demonstration of Usages of the PB-ID Switch 3.1) Rapid Drug-Free Stable Cell Line Establishment with PB-ID Vectors (FIGS. 9A-9B)

a) Rationale:

When establishing stable cell lines with classic genome-integrative vectors, expression of the GOI (or a selection marker) from transgenes that have integrated in the genome of host cells cannot be reliably assessed prior elimination of episomal vectors. This typically requires multiple rounds of cell division and results in weeks-long delays to select and analyze transgenic cells. In addition, transient episomal expression of GOI at abnormally high levels may perturb metabolism and gene expression, with potential harmful effects on the behavior, identity and viability of target cells. The PB-ID switch enables to bypass these issues by restricting GOI and/or marker expression to genome-integrated transgenes. Cells in which the transgene is integrated can therefore be identified by GOI and/or marker expression shortly (48 hrs) after transfection, and the burst of expression associated with transient episomes is avoided.

b) Implementation (FIG. 9A):

High-efficiency drug-free stable cell line establishment with the PB-ID switch was validated with a vector expressing RFP based on the PB-ID transcriptional switch (PB-IDCAG∞RFP). To this aim, HEK-293 cells were transfected along with PBase either with the PB-IDCAG∞RFP vector or with a classic piggyBac transposon vector (PBCAG::RFP). After 2 days in culture, RFP-positive cells were sorted and plated as single cells in 96-well dishes by FACS. After 10 days of expansion (in absence of any drug selection), 95.78%±0.73 SEM of clones derived from cells transfected with the PB-ID vector expressed RFP, while in the same conditions only 55.18%±5.07 SEM of clones derived from the classic piggyBac vector were RFP-positive (FIG. 9A). These results validate the PB-ID switch as a tool to generate transgenic cell lines with high efficiency by sorting positive cells based on GOI or marker expression without the need to await episome dilution.

c) Validation In Vitro in Embryonic Stem (ES) Cells (FIGS. 11A-11D) ES cells from mice were transfected with PB-zIDCAG∞GFP-Kras and CAG::hyPBase vectors. In mouse ES cells, fluorescence-based clonal selection with the PB-zIDCAG∞GFP-Kras vector demonstrated a high enrichment in integrative events compared to a classic transposon (FIG. 11A). Thus, the dependence of the PB-ID switch on transposition enables an efficient transgene activation and an efficient genomic integration. Importantly, short and long-term viability with PB-ID vectors were comparable to that of classic transposons (FIGS. 11B and 11C), and the switch was active in all cells tested, including HeLa and 3T3 (FIG. 11D). These results establish PB-ID as a tool for highly efficient drug-free transgenesis through which genomic expression of GOIs can be assessed directly after transfection without interfering episomal expression.

3.2) Generation of Cell Lines Co-Expressing Multiple Transgenes (Multiplex Transgenesis) with PB-ID (FIG. 9B)

a) Rationale:

Selecting and establishing cell lines that stably co-express multiple transgenes is difficult with classic protocols. For instance, multiplexing selection based on drug resistance requires simultaneous or consecutive application of several distinct drugs, a delicate and complex procedure that may potentially have detrimental effects on transfected cells. Furthermore, due to the limited yield of classic approaches for stable transgenesis, cells that co-integrate multiple transgenes typically represent only a minority of transfected cells. Co-transfecting cells with PB-ID vectors bearing distinct fluorescent protein markers offers the possibility to select cell lines that co-express multiple transgenes both rapidly and with high yield.

b) Implementation (FIG. 9B):

High-efficiency drug-free multiplex stable cell line establishment with PB-ID was validated using three vector expressing mRFP1, EGFP and IRFP670 based on the PB-ID translational switch (PB-zIDCAG∞RFP, PB-zIDCAG∞EGFP and PB-zIDCAG∞IRFP). To this aim, HEK-293 cells were co-transfected in presence of PBase either with a mixture of the three PB-ID vectors, or with classic piggyBac transposon vectors (PBCAG::RFP, PBCAG::EGFP and PBCAG::IRFP). After 2 days in culture, cells co-expressing the three fluorescent proteins were sorted and plated as single cells in 96-well dishes by FACS. After 10 days of expansion (in absence of any drug selection), a majority (79.64%±3.76 SEM) of clones derived from cells coexpressing the three markers had maintained their expression, while transfection with the three piggyBac vectors yielded only 22.43%±2.22 SEM of triple transgenic clones. These results validate the PB-ID switch as a tool to generate cell lines that stably express multiple transgenes with high efficiency, by sorting positive cells based on marker co-expression without the need to await episome dilution.

c) Validation In Vitro in Human Induced Pluripotent Stem (iPS Cells) (FIG. 12)

The iPS cells were co-transfected with a mixture of the three PB-ID vectors (PB-zIDCAG∞RFP, PB-zIDCAG∞GFP and PB-zIDCAG∞IRFP). Clones which co-expressing the three fluorescent proteins similarly maintained their expression at near homogenous levels over multiple passages (FIG. 12). The three-color PB-zID transgenes also allowed a long-term expression during iPS cells differentiation towards the neural lineage. Thus, PB-ID provides an efficient tool for multiplex transgenesis in cell culture models.

3.3) Genomic Expression of a Functionally Active GOI and Readout of its Effects with PB-ID Vectors (FIGS. 7A1-7B)

a) Rationale:

Monitoring the effects of transgenes integrated in the genome of transfected cells (as opposed to that of episomal transgenes) is desirable for a variety of purposes, for instance to experimentally assess the function of certain gene products in gain- and loss-of-function experiments, when expressed over the long term, at constant physiological levels and/or under the regulation of epigenetic factors. With classic vectors that are active in episomal form, transient transgene expression from episomes masks that of integrated transgenes, causing a burst of expression at non-physiological level and rapid changes in expression. While inducible strategies may in certain cases enable to bypass this problem, they still require episome dilution which significantly delays analysis. The PB-ID switch restricts expression to genome-integrated transgenes, thus enabling to specifically monitor the effects of GOIs produced by these transgenes. Co-expression of a marker such as a fluorescent protein can then be used to identify cells producing the GOI in functional experiments.

b) Implementation:

To validate the possibility to perform genetic mosaic analysis with PB-ID vectors, we used as GOI the Notch receptor intracellular domain, known for its inhibitory effects on neural progenitor cell differentiation (Pierfelice et al., 2011). We used the PB-zIDCAG∞RFP-2A-NICD vector presented in (I.2.6) enabling PBase-dependent co-expression of RFP and NICD (FIGS. 7A1-7B). This vector was co-transfected with PBase as well as a control vector (PBzIDCAG∞EGFP) in the embryonic chicken spinal cord. After 3 or 6 days of incubation, analysis of labeled cells showed the effect expected for long-term expression of NICD: strong reduction of neurogenesis affecting RFP+ cells while GFP+ cells were less affected, and expansion of RFP+ progenitor cells located at the ventricular surface compared with a control condition (corresponding to electroporation of zPB-IDCAG∞EGFP). Thus the PB-ID switch can be used to induce specific genetic perturbations and track affected and non-affected cells with distinct color labels.

3.4) Cell Lineage Tracing and Clonal Analysis with PB-ID Vectors (FIGS. 10A-10C)

a) Rationale:

Cell lineage tracing and clonal analysis approaches are widely used in studies of tissue development and homeostasis to analyze the fate of stem/progenitor cells in vitro or in vivo, either at the level of cell population or individual cells. This requires marking cells of interest with permanent labels that are transmitted through their divisions. Among tools available for this purpose, genome-integrative transposon-based vectors are attractive because of their simplicity and straightforward applicability to a wide range of models. Furthermore, multicolor labeling approaches based on transposons have been developed to facilitate the identification of clones and/or clonal borders by marking the progeny or different individual progenitors with distinct color markers (Figueres-Oñate et al., 2016; Garcia-Moreno et al., 2014; Loulier et al., 2014; Siddiqi et al., 2014). However, a general problem with transposon-based clonal labeling schemes is that markers expressed from non-integrated transposon vectors initially superimpose with integrated transgenes prior to episome dilution by cell divisions, thus impeding clonal identification. By restricting marker expression to genome-integrated labels, the PB-ID switch makes it possible to bypass this problem. The effectiveness of PB-ID vectors for long term cell lineage tracing and for multicolor clonal analysis in vivo in the developing vertebrate nervous system was therefore demonstrated.

b) Implementation:

Long-Term Cell Lineage Tracing (FIG. 10A):

The applicability of PB-ID vectors to trace progenitor cell lineage using as a model the mouse cerebral cortex was verified. The PB-IDCAG∞RFP vector was electroporated in utero at E12 in embryonic cortical progenitors lining the cerebral ventricle along with PBase and a control CAG:: GFP plasmid. At E18 (6 days after electroporation), as expected, GFP expression was restricted to neurons occupying intermediate layers of the cerebral cortex, born at the time of electroporation or shortly after (cells born subsequently were not labeled, as anticipated from the dilution of the CAG::GFP plasmid through progenitor cell division). In contrast, RFP expression was found in a stream of cells migrating radially from the ventricular surface towards intermediate and upper cortical layers, as anticipated in the case of permanent labeling of their parent progenitor. At P10 (15 days after electroporation), RFP labeling was observed in differentiated neurons of intermediate and upper cortical layers as well as astrocytes located throughout the cortical wall, while GFP expression was again restricted to intermediate layers neurons. This pattern of expression is compatible only with permanent labeling of cortical progenitors with the PB-ID vector. Thus, the PB-ID switch can be used to trace the lineage of progenitor/stem cells in vivo over extended periods of development.

Clonal Analysis (FIG. 10B):

We developed a multicolor cell lineage tracing scheme based on the PB-ID switch, using mixtures of vectors expressing distinct color of fluorescent protein makers. To this aim we employed the three vectors mentioned in (I.2.3) (PB-zIDCAG∞RFP, PB-zIDCAG∞EGFP and PB-zIDCAG∞IRFP vectors) which we co-electroporated in ovo in a semi-sparse manner in the spinal cord of E2 chickens embryos along with PBase. Analysis at E6 revealed parallel streams of cells migrating radially from the ventricular surface, homogeneously labeled with a variety of different colors. Such distribution corresponded to clonal patterns observed in the spinal cord with other approaches (Leber and Sanes, 1995; Loulier et al., 2014). The cells expressed rich combinations of the three fluorescent markers that enabled to identify clones at global labeling densities higher than that necessary with monochrome clonal labels. The color palette observed with PB-ID vectors was as much or more extended than that obtained with previous transposon-based multicolor lineage tracing methodologies. The PB-ID switch is thus an efficient tool to label and map groups of clonally-related cells and/or their limits relative to other clones.

REFERENCES

Anastassiadis, K., Fu, J., Patsch, C., Hu, S., Weidlich, S., Duerschke, K., Buchholz, F., Edenhofer, F., and Stewart, A. F. (2009). Dre recombinase, like Cre, is a highly efficient site-specific recombinase in *E. coli*, mammalian cells and mice. Dis Model Mech 2, 508-515.

Beard, C., Hochedlinger, K., Plath, K., Wutz, A., and Jaenisch, R. (2006). Efficient method to generate single-copy transgenic mice by site-specific integration in embryonic stem cells. Genesis 44, 23-28.

Branda, C. S., and Dymecki, S. M. (2004). Talking about a revolution: The impact of site-specific recombinases on genetic analyses in mice. Dev Cell 6, 7-28.

Campbell, R. E., Tour, O., Palmer, A. E., Steinbach, P. A., Baird, G. S., Zacharias, D. A., and Tsien, R. Y. (2002). A monomeric red fluorescent protein. Proc Natl Acad Sci USA 99, 7877-7882.

Cary, L. C., Goebel, M., Corsaro, B. G., Wang, H. G., Rosen, E., and Fraser, M. J. (1989) Transposon mutagenesis of baculoviruses: Analysis of *Trichoplusia ni* transposon IFP2 insertions within the FP-locus of nuclear polyhedrosis viruses. Virology; 172: 156-169

Chiodini, F., Matter-Sadzinski, L., Rodrigues, T., Skowronska-Krawczyk, D., Brodier, L., Schaad, O., Bauer, C., Ballivet, M., and Matter, J.-M. (2013). A positive feedback loop between ATOH7 and a Notch effector regulates cell-cycle progression and neurogenesis in the retina. Cell Rep. 3, 796-807.

Figueres-Oñate, M., Garcfa-Marqués, J., and López-Mascaraque, L. (2016). UbC-StarTrack, a clonal method to target the entire progeny of individual progenitors. Sci. Rep. 6, 33896.

Fraser, M. J., Cary, L., Boonvisudhi, K., and Wang, H. G. (1995) Assay for movement of Lepidopteran transposon IFP2 in insect cells using a baculovirus genome as a target DNA. Virology.; 211: 397-407

Fraser, M. J., Ciszczon, T., Elick, T., and Bauser, C. (1996) Precise excision of TTAA-specific lepidopteran transposons piggyBac (IFP2) and tagalong (TFP3) from the baculovirus genome in cell lines from two species of Lepidoptera. Insect Mol. Biol.; 5: 141-151

Gaj, T., Gersbach, C. A., and Barbas, C. F. 3rd (2013). ZFN, TALEN, and CRISPR/Cas-based methods for genome engineering. Trends Biotechnol. 31, 397-405.

Garcia-Moreno, F., Vasistha, N. A., Begbie, J., and Molnar, Z. (2014). CLoNe is a new method to target single progenitors and study their progeny in mouse and chick. Development 141, 1589-1598.

Gibson DG1, Young L, Chuang RY, Venter JC, Hutchison CA 3rd, Smith HO. Enzymatic assembly of DNA molecules up to several hundred kilobases. Nat Methods. 2009 May; 6(5):343-5.

Hustedt, N., and Durocher, D. (2017). The control of DNA repair by the cell cycle. Nat. Cell Biol. 19, 1-9.

Jullien, N. (2003). Regulation of Cre recombinase by ligand-induced complementation of inactive fragments. Nucleic Acids Res. 31, 131e-131.

Kakoki, M., Tsai, Y. S., Kim, H. S., Hatada, S., Ciavatta, D. J., Takahashi, N., Arnold, L. W., Maeda, N., and Smithies, O. (2004). Altering the expression in mice of genes by modifying their 3' regions. Dev. Cell 6, 597-606.

Keil, G. M., Ebeling-Keil, A., and Koszinowski, U. H. (1987). Sequence and structural organization of murine cytomegalovirus immediate-early gene 1. J. Virol. 61, 1901-1908.

Lacoste, A., Berenshteyn, F., and Brivanlou, A. H. (2009). An efficient and reversible transposable system for gene delivery and lineage-specific differentiation in human embryonic stem cells. Cell Stem Cell 5, 332-342.

Leber, S. M., and Sanes, J. R. (1995). Migratory paths of neurons and glia in the embryonic chick spinal cord. J Neurosci 15, 1236-1248.

Li, M. A., Turner, D. J., Ning, Z., Yusa, K., Liang, Q., Eckert, S., Rad, L., Fitzgerald, T. W., Craig, N. L., and Bradley, A. (2011). Mobilization of giant piggyBac transposons in the mouse genome. Nucleic Acids Res. 39, e148.

Loulier, K., Barry, R., Mahou, P., Franc, Y. L., Supatto, W., Matho, K. S., Ieng, S., Fouquet, S., Dupin, E., Benosman, R., et al. (2014). Multiplex Cell and Lineage Tracking with Combinatorial Labels. Neuron 81.

Maury, Y., C8me, J., Piskorowski, R. A., Salah-Mohellibi, N., Chevaleyre, V., Peschanski, M., Martinat, C., and Nedelec, S. (2015). Combinatorial analysis of developmental cues efficiently converts human pluripotent stem cells into multiple neuronal subtypes. Nat. Biotechnol. 33, 89-96.

Niwa, H., Yamamura, K., and Miyazaki, J. (1991). Efficient selection for high-expression transfectants with a novel eukaryotic vector. Gene 108, 193-199.

Pierfelice, T., Alberi, L., and Gaiano, N. (2011). Notch in the vertebrate nervous system: an old dog with new tricks. Neuron 69, 840-855.

Rogers, S., Wells, R., and Rechsteiner, M. (1986). Amino acid sequences common to rapidly degraded proteins: the PEST hypothesis. Science 234, 364-368.

Shcherbakova, D. M., and Verkhusha, V. V. (2013). Near-infrared fluorescent proteins for multicolor in vivo imaging. Nat. Methods 10, 751-754.

Siddiqi, F., Chen, F., Aron, A. W., Fiondella, C. G., Patel, K., and LoTurco, J. J. (2014). Fate mapping by piggybac transposase reveals that neocortical glast+ progenitors generate more astrocytes than nestin+ progenitors in rat neocortex. Cereb. Cortex 24, 508-520.

Skowronska-Krawczyk, D., Chiodini, F., Ebeling, M., Alliod, C., Kundzewicz, A., Castro, D., Ballivet, M., Guillemot, F., Matter-Sadzinski, L., and Matter, J.-M. (2009). Conserved regulatory sequences in Atoh7 mediate non-conserved regulatory responses in retina ontogenesis. Development 136, 3767-3777.

Smith, M. C. M., Brown, W. R. A., McEwan, A. R., and Rowley, P. A. (2010). Site-specific recombination by phiC31 integrase and other large serine recombinases. Biochem. Soc. Trans. 38, 388-394.

Turan, S., and Bode, J. (2011). Site-specific recombinases: from tag-and-target- to tag-and-exchange-based genomic modifications. FASEB J. 25, 4088-4107.

Wang, Y., Wang, J., Devaraj, A., Singh, M., Jimenez Orgaz, A., Chen, J. X., Selbach, M., Ivics, Z., and Izsvik, Z. (2014). Suicidal Autointegration of Sleeping Beauty and piggyBac Transposons in Eukaryotic Cells. PLoS Genet. 10.

Woodard, L. E., and Wilson, M. H. (2015). piggyBac-ing models and new therapeutic strategies. Trends Biotechnol. 33, 525-533.

Wu, S. C.-Y., Meir, Y.-J. J., Coates, C. J., Handler, A. M., Pelczar, P., Moisyadi, S., and Kaminski, J. M. (2006). piggyBac is a flexible and highly active transposon as compared to sleeping beauty, Tol2, and Mos1 in mammalian cells. Proc. Natl. Acad. Sci. U.S.A 103, 15008-15013.

Xu, Z., Thomas, L., Davies, B., Chalmers, R., Smith, M., and Brown, W. (2013). Accuracy and efficiency define Bxb1 integrase as the best of fifteen candidate serine recombinases for the integration of DNA into the human genome. BMC Biotechnol. 13, 1-17.

Yusa, K., Zhou, L., Li, M. A., Bradley, A., and Craig, N. L. (2011). A hyperactive piggyBac transposase for mammalian applications. Proc. Natl. Acad. Sci. 108, 1531-1536.

Zahn-Zabal M, Kobr M, Girod PA, Imhof M, Chatellard P, de Jesus M, Wurm F, Mermod N. (2001) Development of stable cell lines for production or regulated expression using matrix attachment regions. J Biotechnol.; 87(1):29-42.

Zhu, F., Gamboa, M., Farruggio, A. P., Hippenmeyer, S., Tasic, B., Schule, B., Chen-Tsai, Y., and Calos, M. P. (2014). DICE, an efficient system for iterative genomic editing in human pluripotent stem cells. Nucleic Acids Res. 42, e34.

The invention claimed is:

1. A recombinant vector, comprising:
a promoter;
a gene of interest; and
a set of two sequences consisting of:
a first sequence comprising or consisting of a 5' ITR of a DNA transposon which is in the sense orientation with respect to the orientation of the promoter, and
a second sequence comprising or consisting of a 3' ITR of a DNA transposon which is in the antisense orientation with respect to the orientation of the promoter,
wherein one of the first sequence or of the second sequence of said set of two sequences is located between the promoter and at least part of the gene of interest, and wherein said at least part of the sequence of the gene of interest is in an anti-sense orientation with respect to the orientation of the promoter.

2. The recombinant vector according to claim 1, wherein the first sequence and the second sequence of the set of two sequences respectively comprise or consist of a 5' ITR and a 3' ITR of a cut and paste DNA transposon.

3. The recombinant vector according to claim 1, wherein the first sequence and the second sequence of the set of two sequences respectively comprise or consist of, 5' ITR and 3' ITR from a DNA transposon chosen in the list consisting of piggyBac, Tol2 and Sleeping Beauty transposons.

4. The recombinant vector according to claim 1,
wherein the set of two sequences consists of a first sequence and a second sequence respectively comprising or consisting of 5' and 3' ITR of piggyBac transposon, and
wherein the sequence of said set comprising or consisting of the 5' ITR of piggyBac transposon is localized downstream of the promoter sequence and separates the promoter from the at least part of the sequence of the gene of interest which is in an anti-sense orientation with respect to the sequence of the promoter.

5. The recombinant vector according to claim 1 wherein the set of two sequences consists of a first sequence and a second sequence respectively comprising or consisting of 5' and 3' ITR of piggyBac transposon, and
wherein the sequence of the gene of interest is present in the recombinant vector in the form of two fragments consisting of the 5' terminal part of the gene of interest and the 3' terminal part of the gene of interest,
wherein the 3' terminal part of the sequence of the gene of interest is in an anti-sense orientation with respect to the sequence of the promoter,
wherein the 5' terminal part of the sequence of the gene of interest is localized downstream of the promoter sequence and is in the sense orientation with respect to the orientation of the promoter; and
wherein one of the two sequences of said set is located between the promoter and the 3' end of the sequence of the gene of interest.

6. The recombinant vector according to claim 1, further comprising a sequence encoding a transposase.

7. A recombinant vector according to claim 1, wherein the said at least part of the gene of interest is flanked by one of the two sequences of said set which is located between the promoter and at least part of the gene of interest and by the other one of the two sequences of said set.

8. A kit comprising a recombinant vector according to claim 1, and a transposase enzyme or a transposase expression vector comprising a sequence encoding the transposase enzyme.

* * * * *